US008580525B2

(12) United States Patent
Penner et al.

(10) Patent No.: US 8,580,525 B2
(45) Date of Patent: Nov. 12, 2013

(54) METHODS OF SCREENING FOR LTRPC7 MODULATORS

(75) Inventors: Reinhold Penner, Honolulu, HI (US); Andrea Fleig, Honolulu, HI (US)

(73) Assignee: The Queen's Medical Center, Honolulu, HI (US)

( * ) Notice: Subject to any disclaimer, the term of this patent is extended or adjusted under 35 U.S.C. 154(b) by 409 days.

(21) Appl. No.: 12/128,471

(22) Filed: May 28, 2008

(65) Prior Publication Data

US 2009/0098546 A1  Apr. 16, 2009

Related U.S. Application Data

(63) Continuation of application No. 10/008,539, filed on Nov. 13, 2001, now abandoned.

(60) Provisional application No. 60/248,235, filed on Nov. 13, 2000, provisional application No. 60/254,468, filed on Dec. 8, 2000.

(51) Int. Cl.
*G01N 33/567* (2006.01)
*C12N 5/22* (2006.01)

(52) U.S. Cl.
USPC ............ 435/7.2; 435/369; 435/375; 514/17.4

(58) Field of Classification Search
None
See application file for complete search history.

(56) References Cited

FOREIGN PATENT DOCUMENTS

| EP | 1048727 A1 | 11/2000 |
|----|------------|---------|
| WO | WO 00/40614 A2 | 7/2000 |
| WO | WO 0040614 A2 | 7/2000 |
| WO | WO 00/65056 A2 | 11/2000 |
| WO | WO 02/10391 A2 | 2/2002 |
| WO | WO 02/14368 A2 | 2/2002 |
| WO | WO 02059307 A2 * | 8/2002 |

OTHER PUBLICATIONS

Aarts et al. 2003, "A Key Role for TRPM7 Channels in Anoxic Neuronal Death" *Cell*, 115:863-877.
Atchison, 2003, "Effects of Toxic Environmental Contaminants on Voltage-Gated Calcium Channel Function: From Past to Present" *Journal of Bioenergetics and Biomembranes*, 35(6): 507-532.
Bork 2000, "Powers and Pitfalls in Sequence Analysis: the 70% Hurdle" *Genome Research* 10: 398.
Bork and Bairoch 1996 "Go hunting in sequence databases but watch out for traps" *Trends in Genetics* 12(10):425.
Brenner 1999, "Errors in genome annotation" *Trends in Genetics* 15(4):132.
Camello et al. 1999 "Sequential activiation of different Ca2+ entry pathways upon cholinergic stimulation in mouse pancreatic acinar cells" *Journal of Physiology* 516(2):399-408.
Doereks et al. 1998, "Protein annotatino: detective work for function prediction" *Trends in Genetics*, 14(6): 248.
Gossen et al. 1992 "Tight control of gene epxression in mammalian cells by tetracycline-responsive promoters" *PNAS* 89:5547-5551.
Harteneck et al. 2000, "From worm to man: three subfamilies of TRP channels" *Trends Neuroscience* 23(4): 159-166.
Karp 1996 "Cell and Molecular Biology" *John Wiley & Sons* p. 644.
Lehmann-Horn and Jurakat-Rott, 1999, "Voltage-Gated Ion Channels and Hereditary Disease" *Physiological Reviews* 79(4): 1317-1372.
Lehninger et al. 1993 "Principles of Biochemistry" *John Wiley & Sons, Inc.* p. 187.
Levitan et al., 2001 "TRP Ion Channels—Two Proteins in One" *Science* 293:1270-1271.
Liuzzi, et al. 2004, Responsive Transporter Genes Within the murine-intestinal axis form a basis of zinc homeostasis *Annu Rev Nutr.*, 24: 151-172.
Logan et al. 1994, "Cystic Fibrosis Transmembrane Conductance Regulator Mutations That Disrupt Nucleotide Binding" *J. Clinical Invest.*, 94:228-236.
Monteilh-Zoller et al., 2003, "TRPM7 Provides an Ion Channel Mechanism for Cellular Entry of Trace Metal Ions" *Journal of General Physiology*, 121:49-60.
Nadler et al. 2000, "LTRPC7 is a Mg-ATP-regulated divalent cation channel required for cell visability" *Nature* 411:590-595.
Nagamine et al. 1998, "Molecular cloning of a novel putative Ca2+ channel protein (TRPC7) highly expressed in Brain" *Genomics* 54(1): 124-131.
Ngo, et al. 1995, "The Protein Folding Problem and Tertiary Structure Prediction, Chapter 14: Computational Complexity Protein Structure Prediction, and the Levrinthal Paradox", p. 492-495.
Perraud et al., 2001, ADP-ribose gating of the calcium-permeable LTRPC2 channel revealed by Nudix motif homology *Nature* 411:595-599.
Runnels et al. 2001 "TRP-PLIK, a bifunctional protein with kinase and ion channel activities" *Science* 291(15506): 1043-1047.
Ryazanov et al. 1999, "Alpha-kinases: a new class of protein kinases with a novel catalytic domain" *Curr. Biol.* 9(2): R43-5.

(Continued)

*Primary Examiner* — Zachary Howard
(74) *Attorney, Agent, or Firm* — Morgan Lewis & Bockius LLP

(57) ABSTRACT

The present invention relates to the identification and isolation of a novel family of ATP regulated calcium transmembrane channel polypeptides designated herein as "LTRPC7" (Long Transient Receptor Potential Channel). Channels comprising these polypeptides close in response to concentrations of cytoplasmic ATP in the millimolar range, are subject to inhibition by high intracellular levels of calcium and/or magnesium, and do not respond to depletion or reduction in intracellular calcium stores. The invention further relates to the methods of utilizing LTRPC7 for binding, and the methods for modulating LTRPC7 activity and for measuring LTRPC2 permeability. The invention further relates to the methods of modulating expression of LTRPC7.

28 Claims, 22 Drawing Sheets

(56) References Cited

OTHER PUBLICATIONS

Sano et al. 2001, "Immunocyte Ca2+ influx system mediated by LTRPC2" *Science* 1327-1330.

Skolnick and Fetrow 2000 "From genes to protein structure and function: novel applications of computational approaches in the genomic era" *Trends in Biotech* 18(1):34.

Smith and Zhang 1997,"The challenges of genome sequence annotation or 'The devil is in the details'" *Nature Biotechnology* 15:1222.

Voets et al., 2003 "The pore of TRP channels: trivial or neglected?" *Cell Calcium* 33: 299-302.

Wells, 1980, "Activity of Mutational Effects in Proteins" *Biochemistry* 29:8509-8517.

Yamaguchi et al. 2001, "Crystal structure of the atypical protein kinase domain of a TRP channel with phosphotransferase activity" *Moll Cel.* 7(5): 1047-1057.

Yan et al. 2000 "Two amino-acid molecular switch in an epithelial morphogen that regulates binding to two distinct receptors." *Science* 290:523-527.

Zhu et al. 1998 "Receptor-activated Ca2+ Influx via Human Trp3 Stably Expressed in Human Embroyonic Kidney (HEK) 293 Cells" *Journal of Biological Chemistry* 273(1): 133-142.

\* cited by examiner

| Library (human) | LTRPC7 |
|---|---|
| 1. bone marrow | + |
| 2. spleen | + |
| 3. brain | + |
| 4. heart | ++ |
| 5. kidney | + |
| 6. testis | ++ |
| 7. prostate | ++ |
| 8. leukocyte | + |
| 9. liver | + |
| 10. lung | + |
| 11. skeletal muscle | + |
| 12. fetal brain | + |
| 13. fetal heart | ++ |
| 14. fetal kidney | ++ |
| 15. prostate adenocarcinoma | + |
| 16. prostate leiomyosarcoma | ++ |

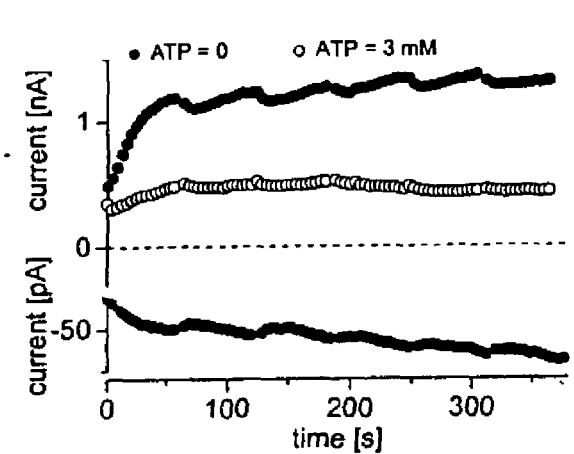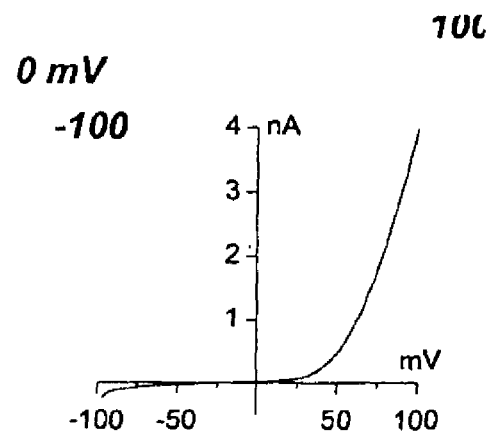
Fig. 11(A)         Fig. 11(B)
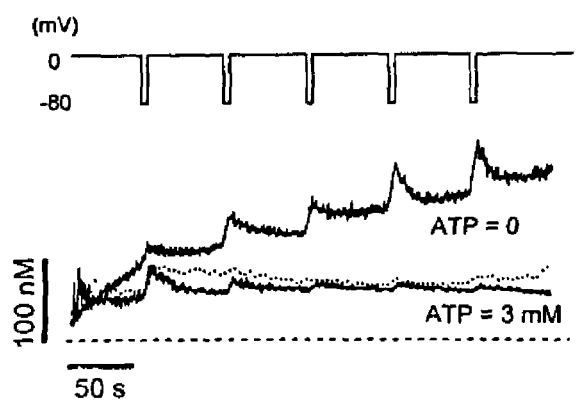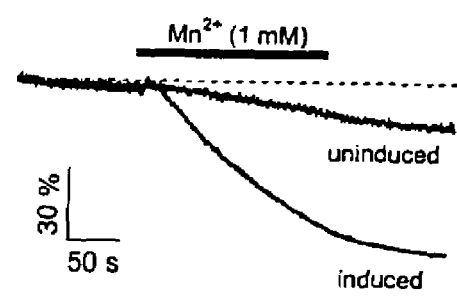
Fig. 11(C)         Fig. 11(D)

```
   1 msqkswiest ltkrecvyii psskdphrcl pgcqicqqlv rcfcgrlvkq hacftaslam
  61 kysdvklgdh fnqaieewsv ekhteqsptd aygvinfqgg shsyrakyvr lsydtkpavi
 121 lqlllkewqm elpklvisvh ggmqkfelhp rikqllgkgl ikaavttgaw iltggvntgv
 181 akhvgdalke hasrssrkic tigiapwgvi enrndlvgrd vvapyqtlln plsklnvlnn
 241 lhshfilvdd gtvgkygaev rlrrelekti nqqriharig qgvpvvalif eggpnviltv
 301 leylqesppv pvvvcegtgr aadllayihk qteeggnlpd aaepdiisti kktfnfgqne
 361 alhlfqtlme cmkrkelitv fhigsdehqd idvailtall kgtnasafdq liltlawdrv
 421 diaknhvfvy gqqwlvgsle qamldalvmd rvafvkllie ngvsmhkflt iprleelynt
 481 kqgptnpmlf hlvrdvkqgn lppgykitli diglvieylm ggtyrctytr krfrliynsl
 541 ggnnrrsgrn tssstpqlrk shesfgnrad kkekmrhnhf iktaqpyrpk idtvmeegkk
 601 krtkdeivdi ddpetkrfpy plnelliwac lmkrqvmarf lwqhgeesma kalvackiyr
 661 smayeakqsd lvddtseelk qysndfgqla velleqsfrq detmamkllt yelknwsnst
 721 clklavssrl rpfvahtctq mlsdmwmgr lnmrknswyk vilsilvppa illleyktka
 781 emshipqsqd ahqmtmddse nnfqniteei pmevfkevri ldsnegknem eiqmkskklp
 841 itrkfyafyh apivkfwfnt laylgflmly tfvvlvqmeq lpsvqewivi ayiftyaiek
 901 vreifmseag kvnqkikvwf sdyfnisdti aiisffigfg lrfgakwnfa naydnhvfva
 961 grliyclnii fwyvrlldfl avnqqagpyv mmigkmvanm fyivvimalv llsfgvprka
1021 ilypheapsw tlakdivfhp ywmifgevya yeidvcands vipqicgpgt wltpflqavy
1081 lfvqyiimvn lliaffnnvy lqvkaisniv wkyqryhfim ayhekpvlpp pliilshivs
1141 lfccickrrk kdktsdgpkl flteedqkkl hdfeeqcvem yfnekddkfh sgseerirvt
1201 ferveqmciq ikevgdrvny ikrslqslds qighlqdlsa ltvdtlktlt aqkaseaskv
1261 hneitrelsi skhlaqnlid dgpvrpsvwk khgvvntlss slpqgdlesn npfhcnilmk
1321 ddkdpqcnif gqdlpavpqr kefnfpeags ssgalfpsav sppelrqrlh gvellkifnk
1381 nqklgsssts iphlsspptk ffvstpsqps ckshletgtk dqetvcskat egdntefgaf
1441 vghrdsmdlq rfketsnkik ilsnnntsen tlkrvsslag ftdchrtsip vhskqaekis
1501 rrpstedthe vdskaalipd wlqdrpsnre mpseegtlng ltspfkpamd tnyyysaver
1561 nnlmrlsqsi pftpvpprge pvtvyrlees spnilnnsms swsqlglcak ieflskeemg
1621 gglrravkvq ctwsehdilk sghlyiiksf lpevvntwss iykedtvlhl clreiqqqra
1681 aqkltfafnq mkpksipysp rflevfllyc hsagqwfave ecmtgefrky nnnngdeiip
1741 tntleeimla fshwtyeytr gellvldlqg vgenltdpsv ikaeekrscd mvfgpanlge
1801 daiknfrakh hcnsccrklk lpdlkrndyt pdkiifpqde psdlnlqpgn stkesestns
1861 vrlml
```

Fig. 12

```
   1 atgtcccaga aatcctggat agaaagcact ttgaccaaga gggaatgtgt atatattata
  61 ccaagttcca aggaccctca cagatgcctt ccaggatgtc aaatttgtca gcaactcgtc
 121 aggtgttttt gtggtcgctt ggtcaagcaa catgcttgtt ttactgcaag tcttgccatg
 181 aaatactcag atgtgaaatt gggtgaccat tttaatcagg caatagaaga atggtctgtg
 241 gaaaagcata cagaacagag cccaacggat gcttatggag tcataaattt tcaaggggt
 301 tctcattcct acagagctaa gtatgtgagg ctatcatatg acaccaaacc tgaagtcatt
 361 ctgcaacttc tgcttaaaga atggcaaatg gagttaccca aacttgttat ctctgtacat
 421 gggggcatgc agaaatttga gcttcaccca cgaatcaagc agttgcttgg aaaaggtctt
 481 attaaagctg cagttacaac tggagcctgg attttaactg gaggagtaaa cacaggtgtg
 541 gcaaaacatg ttggagatgc cctcaaagaa catgcttcca gatcatctcg aaagatttgc
 601 actatcggaa tagctccatg gggagtgatt gaaaacagaa atgatcttgt gggagagat
 661 gtggttgctc cttatcaaac cttattgaac ccctgagca aattgaatgt tttgaataat
 721 ctgcattccc atttcatatt ggtggatgat ggcactgttg aaagtatgg ggcggaagtc
 781 agactgagaa gagaacttga aaaaactatt aatcagcaaa gaattcatgc taggattggc
 841 cagggtgtcc ctgtggtggc acttatattt gagggtgggc caaatgttat cctcacagtt
 901 cttgaatacc ttcaggaaag cccccctgtt ccagtagttg tgtgaagg aacaggcaga
 961 gctgcagatc tgctagcgta tattcataaa caaacagaag aaggagggaa tcttcctgat
1021 gcagcagagc ccgatattat ttccactatc aaaaaaacat ttaactttgg ccagaatgaa
1081 gcacttcatt tatttcaaac actgatggag tgcatgaaaa gaaaggagct tatcactgtt
1141 ttccatattg ggtcagatga acatcaagat atagatgtag caatacttac tgcactgcta
1201 aaaggtacta atgcatctgc atttgaccag cttatcctta cattggcatg ggatagagtt
1261 gacattgcca aaaatcatgt atttgtttat ggacagcagt ggctggttgg atccttggaa
1321 caagctatgc ttgatgctct tgtaatggat agagttgcat ttgtaaaact tcttattgaa
1381 aatggagtaa gcatgcataa attccttacc attccgagac tggaagaact ttacaacact
1441 aaacaaggtc caactaatcc aatgctgttt catcttgttc gagacgtcaa acaggaaat
1501 cttcctccag gatataagat cactctgatt gatataggac ttgttattga atatctcatg
1561 ggaggaacct acagatgcac ctatactagg aaacgttttc gattaatata taatagtctt
1621 ggtggaaaata atcggaggtc tggccgaaat acctccagca gcactcctca gttgcgaaag
1681 agtcatgaat cttttggcaa tagggcagat aaaaaggaaa aaatgaggca taaccatttc
1741 attaagacag cacagcccta ccgaccaaag attgatacag ttatggaaga aggaaagaag
1801 aaaagaacca aagatgaaat tgtagacatt gatgatccag aaaccaagcg ctttccttat
1861 ccacttaatg aactttaat ttgggcttgc cttatgaaga ggcaggtcat ggcccgtttt
1921 ttatggcaac atggtgaaga atcaatggct aaagcattag ttgcctgtaa gatctatcgt
1981 tcaatggcat atgaagcaaa gcagagtgac ctggtagatg atacttcaga agaactaaaa
2041 cagtattcca atgattttgg tcagttggcc gttgaattat tagaacagtc cttcagacaa
2101 gatgaaacca tggctatgaa attgctcact tatgaactga agaactggag taattcaacc
2161 tgccttaagt tagcagtttc ttcaagactt agacctttg tagctcacac ctgtacacaa
2221 atgttgttat ctgatatgtg gatgggaagg ctgaatatga ggaaaaattc ctggtacaag
2281 gtcatactaa gcatttagt tccacctgcc atattgctgt tagagtataa aactaaggct
2341 gaaatgtccc atatcccaca atctcaagat gctcatcaga tgacaatgga tgacagcgaa
2401 aacaactttc agaacataac agaagagatc cccatggaag tgtttaaaga agtacggatt
2461 ttggatagta atgaaggaaa gaatgagatg gagatacaaa tgaaatcaaa aaagcttcca
2521 attacgcgaa agttttatgc cttttatcat gcaccaattg taaaattctg gtttaacacg
2581 ttggcatatt taggatttct gatgctttat acatttgtgg ttcttgtaca aatggaacag
```

Fig. 13(A)

```
2641 ttaccttcag ttcaagaatg gattgttatt gcttatattt ttacttatgc cattgagaaa
2701 gtccgtgaga tctttatgtc tgaagctggg aaagtaaacc agaagattaa agtatggttt
2761 agtgattact tcaacatcag tgatacaatt gccataattt ctttcttcat tggatttgga
2821 ctaagatttg gagcaaaatg gaacttgca aatgcatatg ataatcatgt ttttgtggct
2881 ggaagattaa tttactgtct taacataata ttttggtatg tgcgtttgct agatttttcta
2941 gctgtaaatc aacaggcagg acctatgta atgatgattg gaaaatggt ggccaatatg
3001 ttctacattg tagtgattat ggctcttgta ttacttagtt ttggtgttcc cagaaaggca
3061 ataactttatc ctcatgaagc accatcttgg actcttgcta aagatatagt ttttcaccca
3121 tactggatga tttttggtga agtttatgca tacgaaattg atgtgtgtgc aaatgattct
3181 gttatccctc aaatctgtgg tcctgggacg tggttgactc catttcttca agcagtctac
3241 ctctttgtac agtatatcat tatggttaat ctccttattg cattttcaa caatgtgtat
3301 ttacaagtga aggcaatttc caatattgta tggaagtacc agcgttatca ttttattatg
3361 gcttatcatg agaaaccagt tctgcctcct ccacttatca ttcttagcca tatagtttct
3421 ctgtttttgct gcatatgtaa gagaagaaag aaagataaga cttccgatgg accaaaactt
3481 ttcttaacag aagaagatca aaagaaactt catgattttg aagagcagtg tgttgaaatg
3541 tatttcaatg aaaaagatga caaatttcat tctgggagtg aagagagaat tcgtgtcact
3601 tttgaaagag tggaacagat gtgcattcag attaaagaag ttggagatcg tgtcaactac
3661 ataaaaagat cattacaatc attagattct caaattggcc atttgcaaga tctttcagcc
3721 ctgacggtag atacattaaa aacactcact gcccagaaag cgtcggaagc tagcaaagtt
3781 cataatgaaa tcacacgaga actgagcatt tccaaacact tggctcaaaa ccttattgat
3841 gatggtcctg taagaccttc tgtatggaaa aagcatggtg ttgtaaatac acttagctcc
3901 tctcttcctc aaggtgatct tgaaagtaat aatcctttc attgtaatat tttaatgaaa
3961 gatgacaaag atccccagtg taatatattt ggtcaagact tacctgcagt accccagaga
4021 aaagaattta attttccaga ggctggttcc tcttctggtg ccttattccc aagtgctgtt
4081 tcccctccag aactgcgaca gagactacat ggggtagaac tcttaaaaat atttaataaa
4141 aatcaaaaat taggcagttc atctactagc ataccacatc tgtcatcccc accaaccaaa
4201 tttttttgtta gtacaccatc tcagccaagt tgcaaaagcc acttggaaac tggaaccaaa
4261 gatcaagaaa ctgtttgctc taaagctaca gaaggagata atacagaatt tggagcattt
4321 gtaggacaca gagatagcat ggatttacag aggtttaaag aaacatcaaa caagataaaa
4381 atactatcca ataacaatac ttctgaaaac actttgaaac gagtgagttc tcttgctgga
4441 tttactgact gtcacagaac ttccattcct gttcattcaa aacaagcaga aaaaatcagt
4501 agaaggccaa ctaccgaaga cactcatgaa gtagattcca aagcagcttt aataccggat
4561 tggttacaag atagaccatc aaacagagaa atgccatctg aagaaggaac attaaatggt
4621 ctcacttctc catttaagcc agctatggat acaaattact attattcagc tgtggaaaga
4681 aataacttga tgaggttatc acagagcatt ccatttacac ctgtgcctcc aagaggggag
4741 cctgcctaac tgtatcgttt ggaagagagt tcacccaaca tactaaataa cagcatgtct
4801 tcttggtcac aactaggcct ctgtgccaaa atagagtttt taagcaaaga ggagatggga
4861 ggaggtttac gaagagctgt caaagtacag tgtacctggt cagaacatga tatcctcaaa
4921 tcaggcatc tttatattat caaatctttt cttccagagg tggttaatac atggtcaagt
4981 atttataaag aagatacagt tctgcatctc tgtctgagag aaattcaaca acagagagca
5041 gcacaaaagc ttacgtttgc ctttaatcaa aatccatacc atattctcca
5101 aggttccttg aagttttcct gctgtattgc cattcagcag gacagtggtt tgctgtggaa
5161 gaatgtatga ctggagaatt tagaaaatac aacaataata atggagatga gattattcca
5221 actaatactc tggaagagat catgctagcc tttagccact ggacttacga atatacaaga
5281 ggggagttac tggtacttga tttgcaaggt gttggtgaaa atttgactga cccatctgtg
5341 ataaaagcag aagaaaagag atcctgtgat atggtttttg gcccagcaga tctaggagaa
5401 gatgcaatta aaaacttcag agcaaaacat cactgtaatt cttgctgtag aaagcttaaa
5461 cttccagatc tgaagaggaa tgattatacg cctgataaaa ttatattcc tcaggatgag
5521 ccttcagatt tgaatcttca gcctggaaat tccaccaaag aatcagaatc aactaattct
5581 gttcgtctga tgttataa
```

Fig. 13(B)

```
   1 ccacgcgtcc gcagcccgt cgccggcgga ggcgggcgcg ggcgcgtncc ctgtggccag
  61 tcacccggag gagttggtcg cacaattatg aaagactcgg cttctgctgc tagcgccgga
 121 gctgagttag ttctgagaag gtttccctgg gcgttccttg tccggcggcc tctgctgccg
 181 cctccggaga cgcttcccga tagatggcta caggccgcgg aggaggagga ggtggagttg
 241 ctgcccttcc ggagtccgcc ccgtgaggag aatgtcccag aaatcctgga tagaaagcac
 301 tttgaccaag agggaatgtg tatatattat accaagttcc aaggaccctc acagatgcct
 361 tccaggatgt caaatttgtc agcaactcgt caggtgtttt tgtggtcgct tggtcaagca
 421 acatgcttgt tttactgcaa gtcttgccat gaaatactca gatgtgaaat tgggtgacca
 481 ttttaatcag gcaatagaag aatggtctgt ggaaaagcat acagaacaga gcccaacgga
 541 tgcttatgga gtcataaatt ttcaaggggg ttctcattcc tacagagcta agtatgtgag
 601 gctatcatat gacaccaaac ctgaagtcat tctgcaactt ctgcttaaag aatggcaaat
 661 ggagttaccc aaacttgtta tctctgtaca tggggcatg cagaaatttg agcttcaccc
 721 acgaatcaag cagttgcttg gaaaaggtct tattaaagct gcagttacaa ctggagcctg
 781 gattttaact ggaggagtaa acacaggtgt ggcaaaacat gttggagatg ccctcaaaga
 841 acatgcttcc agatcatctc gaaagatttg cactatcgga atagctccat ggggagtgat
 901 tgaaaacaga aatgatcttg ttgggagaga tgtggttgct cctatcaaa ccttattgaa
 961 cccctgagc aaattgaatg ttttgaataa tctgcattcc catttcatat tggtggatga
1021 tggcactgtt ggaaagtatg gggcggaagt cagactgaga agagaacttg aaaaactat
1081 taatcagcaa agaattcatg ctaggattgg ccagggtgtc cctgtggtgg cacttatatt
1141 tgagggtggg ccaaatgtta tcctcacagt tcttgaatac cttcaggaaa gccccctgt
1201 tccagtagtt gtgtgtgaag gaacaggcag agctgacagt ctgctagcgt atattcataa
1261 acaaacagaa gaaggaggga atcttcctga tgcagcagag cccgatatta tttccactat
1321 caaaaaaaca tttaactttg gccagaatga agcacttcat ttatttcaaa cactgatgga
1381 gtgcatgaaa agaaaggagc ttatcactgt tttccatatt gggtcagatg aacatcaaga
1441 tatagatgta gcaatactta ctgcactgct aaaaggtact aatgcatctg catttgacca
1501 gcttatcctt acattggcat gggatagagt tgacattgcc aaaaatcatg tatttgttta
1561 tggacagcag tggctggttg gatccttgga acaagctatg cttgatgctc ttgtaatgga
1621 tagagttgca tttgtaaaac ttcttattga aaatggagta agcatgcata aattccttac
1681 cattccgaga ctggaagaac tttacaacac taaacaaggt ccaactaatc caatgctgtt
1741 tcatcttgtt cgagacgtca aacagggtaa tcttcctcca ggatataaga tcactctgat
1801 tgatatagga cttgttattg aatatctcat gggaggaacc tacagatgca cctatactag
1861 gaaacgtttt cgattaatat ataatagtct tggtggaaat aatcggaggt ctggccgaaa
1921 tacctccagc agcactcctc agttgcgaaa gagtcatgaa tctttggca atagggcaga
1981 taaaaggaa aaaatgaggc ataaccattt cattaagaca gcacagccct accgaccaaa
2041 gattgataca gttatgaag aaggaaagaa gaaaagaacc aaagatgaaa ttgtagacat
2101 tgatgatcca gaaaccaagc gcttccctta tccacttaat gaactttaa tttgggcttg
2161 ccttatgaag aggcaggtca tggcccgtt tttatggcaa catggtgaag aatcaatggc
2221 taaagcatta gttgcctgta agatctatcg ttcaatggca tatgaagcaa agcagagtga
2281 cctggtagat gatacttcag aagaactaaa acagtattcc aatgattttg gtcagttggc
2341 cgttgaatta ttagaacagt ccttcagaca agatgaaacc atggctatga aattgctcac
2401 ttatgaactg aagaactgga gtaattcaac ctgccttaag ttagcagttt cttcaagact
2461 tagacctttt gtagctcaca cctgtacaca aatgttgtta tctgatatgt ggatgggaag
2521 gctgaatatg aggaaaaatt cctggtacaa ggtcatacta agcatttag ttccacctgc
2581 catattgtcc ttagagtata aaactaaggc tgaaatccac catatcccac aatctcaaga
2641 tgctcatcag atgacaatgg atgacagcga aaacaacttt cagaacataa cagaagagat
2701 ccccatggaa gtgtttaaag aagtacggat tttggatagt aatgaaggaa agaatgagat
2761 ggagatacaa atgaaatcaa aaaagcttcc aattacgcga aagtttatg cctttatca
2821 tgcaccaatt gtaaaattct ggtttaacac gttggcatat ttaggatttc tgatgcttta
2881 tacatttgtg gtccttgtac aaatgaaaca gttaccttca gtccaagaat ggattgttat
2941 tgcttatatt tttacttatg ccattgagaa agtccgtgag atctttatgt ctgaagctgg
3001 gaaagtaaac cagaagatta agtatggtt tagtgattac ttcaacatca gtgatacaat
3061 tgccataatt tctttcttca ttggatttgg actaagattt ggagcaaaat ggaactttgc
3121 aaatgcatat gataatcatg tttttgtggc tggaagatta atttactgtc ttaacataat
3181 attttggtat gtgcgtttgc tagattttct agctgtaaat caacaggcag gaccttatgt
3241 aatgatgatt ggaaaaatgg tggccaatat gttctacatt gtagtgatta tggctcttgt
3301 attacttagt tttggtgttc ccagaaaggc aatactttat cctcatgaag caccatcttg
3361 gactcttgct aaagatatag ttttcacccc atactgatg attttggtg aagtttatgc
3421 atacgaaatt gatgtgtgtg caaatgattc tgttatccct caaatctgtg gtcctgggac
3481 gtggttgact ccattcttc aagcagtcta cctctttgta cagtatatca ttatggttaa
3541 tcttcttatt gcatttttca acaatgtgta tttacaagtg aaggcaattt ccaatattgt
3601 atggaagtac cagcgttatc attttattat ggcttatcat gagaaaccag ttctgcctcc
3661 tccacttatc attcttagcc atatagtttc tctgttttgc tgcatatgta agagaagaaa
```

Fig. 14(A)

```
3721 gaaagataag acttccgatg gaccaaaact tttcttaaca gaagaagatc aaaagaaact
3781 tcatgatttt gaagagcagt gtgttgaaat gtatttcaat gaaaaagatg acaaatttca
3841 ttctgggagt gaagagagaa ttcgtgtcac ttttgaaaga gtggaacaga tgtgcattca
3901 gattaaagaa gttggagatc gtgtcaacta cataaaaaga tcattacaat cattagattc
3961 tcaaattggc catttgcaag atctttcagc cctgacggta gatacattaa aaacactcac
4021 tgcccagaaa gcgtcggaag ctagcaaagt tcataatgaa atcacacgag aactgagcat
4081 ttccagacac ttggctcaaa accttattga tgatggtcct gtaagacctt ctgtatggaa
4141 aaagcatggt gttgtaaata cacttagctc ctctcttcct caaggtgatc ttgaaagtaa
4201 taatcctttt cattgtaata ttttaatgaa agatgacaaa gatcccagt gtaatatatt
4261 tggtcaagac ttacctgcag tacccagag aaaagaattt aattttccag aggctggttc
4321 ctcttctggt gccttattcc caagtgctgt ttcccctcca gaactgcgac agagactaca
4381 tggggtagaa ctcttaaaaa tatttaataa aaatcaaaaa ttaggcagtt catctactag
4441 cataccacat ctgtcatccc caccaaccaa attttttgtt agtacaccat ctcagccaag
4501 ttgcaaaagc cacttggaaa ctggaaccaa agatcaagaa actgtttgct ctaaagctac
4561 agaaggagat aatacagaat tggagcatt tgtaggacac agagatagca tggatttaca
4621 gaggtttaaa gaaacatcaa acaagataa aatactatcc aataacaata cttctgaaaa
4681 cactttgaaa cgagtgagtt ctcttgctgg atttactgac tgtcacagaa cttccattcc
4741 tgttcattca aaacaagcag aaaaaatcag tagaaggcca tctaccgaag acactcatga
4801 agtagattcc aaagcagctt taataccgga ttggttacaa gatagaccat caaacagaga
4861 aatgccatct gaagaaggaa cattaaatgg tctcacttct ccatttaagc cagctatgga
4921 tacaaattac tattattcag ctgtggaaag aaataacttg atgaggttat cacagagcat
4981 tccatttaca cctgtgcctc caagagggga gcctgtcaca gtgtatcgtt tggaagagag
5041 ttcacccaac atactaaata acagcatgtc ttcttggtca caactaggcc tctgtgccaa
5101 aatagagttt ttaagcaaag aggagatggg aggaggttta cgaagagctg tcaaagtaca
5161 gtgtacctgg tcagaacatg atatcctcaa atcagggcat ctttatatta tcaaatcttt
5221 tcttccagag gtggttaata catgtcaag tatttataaa gaagatacag ttctgcatct
5281 ctgtctgaga gaaattcaac aacagagagc agcacaaaag cttacgtttg cctttaatca
5341 aatgaaaccc aaatccatac catattctcc aaggttcctt gaagttttcc tgctgtattg
5401 ccattcagca ggacagtggt ttgctgtgga agaatgtatg actggagaat ttagaaaata
5461 caacaataat aatggagatg agattattcc aactaatact ctggaagaga tcatgctagc
5521 ctttagccac tggacttacg aatatacaag aggggagtta ctggtacttg atttgcaagg
5581 tgttggtgaa aatttgactg acccatctgt gataaaagca gaagaaaaga gatcctgtga
5641 tatggttttt ggcccagcaa atctaggaga agatgcaatt aaaacttca gagcaaaaca
5701 tcactgtaat tcttgctgta gaaagcttaa acttccagat ctgaagagga atgattatac
5761 gcctgataaa attatatttc ctcaggatga gccttcagat ttgaatcttc agcctggaaa
5821 ttccaccaaa gaatcagaat caactcattc tgttcgtctg atgttataat attaatatta
5881 ctgaatcatt ggttttgcct gcacctcaca gaaatgttac tgtgtcactt ttccctcggg
5941 aggaaattgt ttggtaatat agaaaggtgt atgcaagttg aatttgctga ctccagcaca
6001 gttaaaaggt caatattctt ttgacctgat taatcagtca gaaagtccct ataggataga
6061 gctggcagct gagaaatttt aaaggtaatt gataattagt atttgtaact ttttaaaggg
6121 ctctttgtat agcagaggat ctcatttgac tttgttttga tgaggtgat gccctctctt
6181 atgtggtaca ataccattaa ccaaaggtag gtgtccatgc agatttattt ggcagctgtt
6241 ttattgccat tcaactaggg aaatgaagaa atcacgcagc cttttggtta aatggcagtc
6301 aaaatttcc tcagtgtatt tagtgtgttc agtgatgata tcactggttc ccaactagat
6361 gcttgttggc cacgggaagg gaaatgactt gttctaattc taggttcaca gaggtatgag
6421 aagcctgaac tgaagaccat tttcaagagg gacggtattt atgaatcagg gttaggctcc
6481 atatttaaag atagagccag tttttttttt aaatagaacc caaattgtgt aaaaatgtta
6541 attgggtttt ttaaacattg ttttatcaag tcactgttaa gtagaagaaa gccatggtaa
6601 actgatacat aacctaaatt ataaaagcag aaacctaact cactcgtcaa gggaagttac
6661 cttttgagga aagttaaagt acttttttcc ctatctgtat ctatagcaac aacccagaac
6721 ttacaaactt ctccaaagat tttattgatt gttatatcaa atcagaatgt aaacatgaac
6781 tcttgcatat atttaaaatt gtgttggaac atttgaacat gaatgctgtt tgggtactta
6841 agaaattrat tcagtnggat tatcattatg tganactggc agattgcagt gcanccttat
6901 gccaataaaa tgtaatttaa cagcccaga tattgttgaa tattcaacaa taacaagaaa
6961 agcttttcat ctaagtttta tgctttaatt ttttttcttt tttttctttt ttcttttgtt
7021 tccttggtac taattttaat ttttatttgg aagggagcag tataaagctt atttgtattt
7081 agtagtgtat ctcatagata cagacaaggc aagagatgat aagctgttta aatagtgttt
7141 aatattgatt gggggtgggg agaaagaaaa agtgtattac ttaaagatac tatatacgtt
7201 ttgtatatca ttaaatcttt aaaagaaatn naataaattc attgtttnca aaaaaaaaa
```

Fig. 14(B)

```
   1 msqkswiest ltkrecvyii psskdphrcl pgcqicqqlv rcfcgrlvkq hacftaslam
  61 kysdvklgeh fnqaieewsv ekhteqsptd aygvinfqgg shsyrakyvr lsydtkpeii
 121 lqlllkewqm elpklvisvh ggmqkfelhp rikqllgkgl ikaavttgaw iltggvntgv
 181 akhvgdalke hasrssrkic tigiapwgvi enrndlvgrd vvapyqtlln plsklnvlnn
 241 lhshfilvdd gtvgkygaev rlrrelekti nqqriharig qgvpvvalif eggpnviltv
 301 leylqesppv pvvvcegtgr aadllayihk qteeggnlpd aaepdiisti kktfnfgqse
 361 avhlfqtmme cmkkkelitv fhigsedhqd idvailtall kgtnasafdq liltlawdrv
 421 diaknhvfvy gqqwlvgsle qamldalvmd rvsfvkllie ngvsmhkflt iprleelynt
 481 kqgptnpmlf hlirdvkqgn lppgykitli diglvieylm ggtyrctytr krfrliynsl
 541 ggnnrrsgrn tssstpqlrk shetfgnrad kkekmrhnhf iktaqpyrpk mdasmeegkk
 601 krtkdeivdi ddpetkrfpy plnelliwac lmkrqvmarf lwqhgeesma kalvackiyr
 661 smayeakqsd lvddtseelk qysndfgqla velleqsfrq detmamkllt yelknwsnst
 721 clklavssrl rpfvahtctq mllsdmwmgr lnmrknswyk vilsilvppa ilmleyktka
 781 emshipqsqd ahqmtmedse nnfhniteei pmevfkevki ldssdgknem eihikskklp
 841 itrkfyafyh apivkfwfnt laylgflmly tfvvlvkmeq lpsvqewivi ayiftyaiek
 901 vrevfmseag kisqkikvwf sdyfnvsdti aiisffvgfg lrfgakwnyi naydnhvfva
 961 grliyclnii fwyvrlldfl avnqqagpyv mmigkmvanm fyivvimalv llsfgvprka
1021 ilypheepsw slakdivfhp ywmifgevya yeidvcands tlpticgpgt wltpflqavy
1081 lfvqyiimvn lliaffnnvy lqvkaisniv wkyqryhfim ayhekpvlpp pliilshivs
1141 lfccvckrrk kdktsdgpkl flteedqkkl hdfeeqcvem yfdekddkfn sgseerirvt
1201 ferveqmsiq ikevgdrvny ikrslqslds qighlqdlsa ltvdtlktlt aqkaseaskv
1261 hneitrelsi skhlaqnlid dvpvrplwkk psavntlsss lpqgdresnn pflcnifmkd
1321 ekdpqynlfg qdlpvipqrk efnipeagss cgalfpsavs ppelrqrrhg vemlkifnkn
1381 qklgsspnss phmssppthf svstpsqpsc kshlesttkd qepifykaae gdniefgafv
1441 ghrdsmdlqr fketsnkire llsndtpent lkhvgaagys eccktstslh svqaescsrr
1501 astedapevd skaallpdwl rdrpsnremp seggtlngla spfkpvldtn yyysavernn
1561 lmrlsqsipf vpvpprgepv tvyrleessp silnnsmssw sqlglcakie flskeemggg
1621 lrravkvlct wsehdilksg hlyiiksflp evintwssiy kedtvlhlcl reiqqqraaq
1681 kltfafnqmk pksipysprf levfllychs agqwfaveec mtgefrkynn nngdeiiptn
1741 tleeimlafs hwtyeytrge llvldlqgvg enltdpsvik aeekrscdmv fgpanlgeda
1801 iknfrakhhc nsccrklklp dlkrndytpd kiifpqdess dlnlqsgnst keseatnsvr
1861 lml
```

Fig. 15

```
   1 atgtcccaga aatcctggat agagagcact ttgaccaaga gggagtgtgt atatattata
  61 ccaagctcca aagaccctca cagatgtctt ccaggatgtc agatttgtca gcaacttgtc
 121 agatgtttct gtggtcgttt ggtcaagcaa catgcatgct ttactgcaag tcttgccatg
 181 aaatactcag atgtgaaatt gggtgaacac tttaaccagg caatagaaga atggtctgtg
 241 gaaaagcaca cggagcagag cccaacagat gcttatggag tcatcaattt tcaaggggt
 301 tctcattcct acagagctaa gtatgtgaga ctatcatatg ataccaaacc tgaaatcatt
 361 ctgcaacttc tgcttaaaga atggcaaatg gagttaccca aacttgttat ttctgtacat
 421 ggaggcatgc agaagtttga acttcatcca agaatcaagc agttgcttgg aaagggtctt
 481 attaaagctg cagttacaac cggagcttgg attttaactg gaggagtcaa tacaggtgtg
 541 gcaaaacatg ttggtgatgc cctcaaagaa catgcttcca gatcatctcg aaaaatttgc
 601 actattggaa tagctccatg gggagtgata gaaaacagaa atgatcttgt tgggagagat
 661 gtggttgctc cttatcaaac cctattgaat cccttgagca aattgaatgt tctgaataat
 721 ctacactccc atttcatctt ggtggatgat ggcactgttg gaaagtatgg ggcagaagtc
 781 agactgagaa gagaacttga aaaaccatt aatcagcaaa gaattcatgc tagaattggg
 841 caaggagttc ctgtggtggc tttgatattt gaaggcgggc aaatgtcat ccttacagta
 901 ctggagtacc tcaggaaaag ccccccagtt ccagttgttg tgtgtgaagg gacaggcaga
 961 gctgcagatt tactagccta tatccacaaa cagacagagg aaggaggaaa tcttcctgat
1021 gcagcagagc ctgatattat atcaactatc aagaaaacat ttaacttttgg ccagagtgaa
1081 gcagttcatt tatttcaaac aatgatggag tgtatgaaaa aaaagagct tatcactgtt
1141 tttcacattg gatcagagga tcatcaagat atagatgtgg ccatactcac tgcactgctg
1201 aaagtactaa atgcatctgc atttgaccag cttatcctta cactggcatg ggacagagtt
1261 gatattgcca aaaatcatgt atttgtttat ggacaacagt ggctggttgg atccttggaa
1321 caggctatgc ttgatgctct tgtaatggac agagtttcat ttgtaaaact tcttattgaa
1381 aacggagtaa gcatgcataa attccttacc attcccagac tggaagaact ttataacact
1441 aaacaaggtc caaccaatcc aatgttgttc catctcattc gggatgtcaa gcagggtaat
1501 ctccccccgg ggtacaagat cacttaatt gatataggac ttgtgattga gtatctcatg
1561 ggaggaacct acagatgcac atacacacga aaacgttttc gattgatata taatagtctt
1621 ggtggaaata accggaggtc aggtcgaaat acctccagca gcacccctca gttgcgaaag
1681 agtcatgaaa cttttggcaa tagagctgat aaaaaggaaa aaatgagaca caatcatttc
1741 attaaaacag cccaaccctta cagaccaaag atggatgcat ctatggaaga aggaaagaag
1801 aaaagaacca aagatgaaat tgtagatata gatgatccag agaccaagcg cttccttat
1861 cctcttaatg aattattaat ttgggcttgc cttatgaaga ggcaggtcat ggcccgcttt
1921 ttatggcagc atggtgaaga atcaatggct aaagcattag ttgcctgtaa aatctatcgt
1981 tcaatggctt atgaggcaaa gcagagtgac ctggtagatg atacttcaga ggaactgaag
2041 cagtattcca atgattttgg ccaactggca gttgaattac tggaacagtc cttcagacag
2101 gatgaaacga tggctatgaa attactcact tatgaactca aaaactggag taattcaacc
2161 tgcctcaagt tagcagtttc ttcaagactt agacctttg tagctcacac ttgtacacag
2221 atgttgttat ctgatatgtg gatgggacgg ctgaatatga gaaaaaattc ctggtataag
2281 gtcatattaa gcattttagt tccacctgcc atattaatgc tagagtataa aaccaaggct
2341 gaaatgtccc atatcccaca atctcaagat gctcatcaaa tgcctgatgga ggatagtgaa
2401 aacaatttc acaacataac agaagataga cccatggaag tatttaaaga agtaaagatt
2461 ttggacagca gtgatggaaa gaatgaaatg gagatacata ttaaatcaaa aaagcttcca
2521 atcacacgaa aatttatgc cttttatcat gcaccaattg taaagtctg gtttaacaca
2581 ttggcatatt taggatttct gatgctttat acatttgtag ttcttgtaaa aatggaacag
2641 ttaccttcag ttcaagaatg gattgttatc gcttatattt ttacctatgc tattgaaaaa
```

Fig. 16(A)

```
2701 gtccgtgagg tcttcatgtc tgaagctggg aaaatcagcc agaagattaa agtatggttt
2761 agtgactact tcaatgtcag tgacacaatt gccatcattt ctttctttgt tggatttgga
2821 ctaagatttg gagcaaaatg gaactatatt aatgcatatg ataatcatgt ttttgtggct
2881 ggaagattaa tttactgtct taatataata ttttggtatg tgcgtttgct agactttcta
2941 gccgtaaatc aacaggcagg accttatgta atgatgattg gaaaaatggt ggccaatatg
3001 ttctacattg tagtgataat ggctcttgta ttgcttagtt ttggtgttcc cagaaaagca
3061 atactttatc cacatgaaga accatcttgg tctcttgcta aagatatagt ttttcatcca
3121 tactggatga ttttggtga agtttatgca tatgaaattg atgtgtgtgc aaatgactcc
3181 actctcccga caatctgtgg tcctggaact tggttgactc catttcttca agcagtctac
3241 ctctttgtac agtatatcat tatggttaat ctccttatcg cattttcaa taatgtatat
3301 ttacaagtga aggcaatttc caatattgta tggaagtatc agcggtatca ttttattatg
3361 gcttatcatg aaaaaccagt cctgcctcct cctcttatca tcctcagcca tatagtttca
3421 ctgttttgct gtgtatgcaa aagaagaaag aaagataaga cttccgatgg gccaaaactt
3481 ttcttaacag aagaagatca aagaaactc catgattttg aagagcagtg tgttgagatg
3541 tactttgatg agaaagatga caaattcaat tctgggagtg aagagagaat ccgggtcact
3601 tttgaaagag tggagcagat gagcattcag attaagaag ttggagatcg tgtcaactac
3661 ataaaaagat cattacagtc tttagattct caaattggtc atctgcaaga tctctcagcc
3721 ctaacagtag atacattgaa aacacttaca gcccagaaag cttcagaagc tagtaaagtg
3781 cacaatgaga tcacacgaga attgagtatt tccaaacact tggctcagaa tcttattgat
3841 gatgttcctg taagaccttt gtggaagaaa cctagtgctg taaacacact gagttcctct
3901 cttcctcaag gtgatcggga aagtaataat cctttctttt gtaatatttt tatgaaagat
3961 gaaaaagacc cccaatataa tctgtttgga caagatttgc ccgtgatacc ccagagaaaa
4021 gaattcaaca ttccagaggc tggttcctcc tgtggtgcct tattcccaag tgctgtttct
4081 ccccagaat tacgacagag acgacatggg gtagaaatgt taaaatatt taataaaaat
4141 caaaattag gcagttcacc taatagttca ccacatatgt cctccccacc aaccaaattt
4201 tctgtgagta ccccatccca gccaagttgc aaaagtcact tggaatccac aaccaaagat
4261 caagaaccca ttttctataa agctgcagaa ggggataaca tagaatttgg agcatttgtg
4321 ggacacagag atagtatgga cttacagagg tttaaagaaa catcaaacaa aataagagaa
4381 ctgttatcta atgatactcc tgaaaacact ctgaaacatg tgggtgctgc tggatatagt
4441 gaatgttgta agacttctac ttctcttcac tcggtgcaag cagaaagctg tagtagaaga
4501 gcgtcgacgg aagactctcc agaagtcgat tctaaagcag ctttgttacc ggattggtta
4561 cgagatagac catcaaacag aaaatgcca tctgaaggag gaacattaaa tggtcttgct
4621 tctccattta agccgtttt ggatacaaat tactattatt cagctgtgga aagaaataac
4681 ctgatgaggt tgtcacagag tattcccttc gttcctgtac ctccacgagg cgagcctgtc
4741 acagtgtacc gtctggagga gagttctccc agtatactga ataacagcat gtcttcatgg
4801 tctcagctag gcctctgtgc caaattgag tttttaagta aagaggaaat gggaggtggt
4861 ttacgaagag cagtcaaagt gctgtgtacc tggtcagagc acgatatcct gaagtcaggg
4921 catctctata tcattaagtc atttcttcct gaggtgataa acacatggtc aagcatttat
4981 aaagaagata cggttctaca tctctgtctc agagaaaatac aacaacagag agcagcacaa
5041 aagctcacat ttgcctttaa tcagatgaaa cccaaatcca taccatattc tccaaggttc
5101 cttgaagttt tcctgttgta ctgccattca gcagggcagt ggtttgctgt agaagagtgc
5161 atgactggtg aatttagaaa atacaacaac aataatggtg atgaaatcat tcctacaaat
5221 actctagaag agatcatgct agcctttagc cactggacct atgaatatac cagaggggag
5281 ttactggtac ttgacttaca aggagtggga gaaaacttga ctgacccatc tgtaataaaa
5341 gctgaagaaa aaagatcctg tgacatggtt tttggccctg ccaatctagg agaagatgca
5401 ataaaaaact tcagagccaa acatcactgt aattcttgct gtcgaaagct taaacttcca
5461 gatttgaaga ggaatgacta cacgcctgat aaaattat ttcctcagga tgagtcatca
5521 gatttgaatc ttcaatctgg aaattccacc aaagaatcag aagcaacaaa ttctgttcgt
5581 ctgatgttat ag
```

Fig. 16(B)

```
   1 gccccgtctc cggcggaggc gggcgcgggc gcgtccctgt ggccagtcac ccggcggagc
  61 tggtcgcaca attatgaaag actcgacttc tgctgctagc gctggagctg agttagttct
 121 gagaaggttt cccggggctg tccttgttcg gtggcccgtg ccaccgcctc cggagacgct
 181 ttccgataga tggctgcagg ccgcggaggt ggaggaggag ccgctgccct tccggagtcc
 241 gccccgtgag gagaatgtcc cagaaatcct ggatagagag cactttgacc aagagggagt
 301 gtgtatatat tataccaagc tccaaagacc ctcacagatg tcttccagga tgtcagattt
 361 gtcagcaact tgtcagatgt ttctgtggtc gtttggtcaa gcaacatgca tgctttactg
 421 caagtcttgc catgaaatac tcagatgtga aattgggtga acactttaac caggcaatag
 481 aagaatggtc tgtggaaaag cacacggagc agagcccaac agatgcttat ggagtcatca
 541 attttcaagg gggttctcat tcctacagag ctaagtatgt gagactatca tatgatacca
 601 aacctgaaat cattctgcaa cttctgctta aagaatggca aatggagtta cccaaacttg
 661 ttatttctgt acatggaggc atgcagaagt ttgaacttca tccaagaatc aagcagttgc
 721 ttggaaaggg tcttattaaa gctgcagtta caaccggagc ttggattta actggaggag
 781 tcaatacagg tgtggcaaaa catgttggtg atgccctcaa agaacatgct tccagatcat
 841 ctcgaaaaat ttgcactatt ggaatagctc catggggagt gatagaaaac agaaatgatc
 901 ttgttgggag agatgtggtt gctccttatc aaaccctatt gaatcccttg agcaaattga
 961 atgttctgaa taatctacac tcccatttca tcttggtgga tgatggcact gttggaaagt
1021 atggggcaga agtcagactg agaagagaac ttgaaaaaac cattaatcag caaagaattc
1081 atgctagaat tgggcaagga gttcctgtgg tggctttgat atttgaaggc gggccaaatg
1141 tcatccttac agtactggag taccttcagg aaagcccccc agttccagtt gttgtgtgtg
1201 aagggacagg cagagctgca gatttactag cctatatcca caaacagaca gaggaaggag
1261 gaaatcttcc tgatcagca gagcctgata ttatatcaa tatcaagaaa acatttaact
1321 ttggccagag tgaagcagtt catttatttc aaacaatgat ggagtgtatg aaaaaaaaag
1381 agcttatcac tgtttttcac attggatcag aggatcatca agatatagat gtggccatac
1441 tcactgcact gctgaaaggt actaatgcat ctgcatttga ccagcttatc cttacactgg
1501 catgggacag agttgatatt gccaaaaatc atgtatttgt ttatgacaa cagtggctgg
1561 ttggatcctt ggaacaggct atgcttgatg ctcttgtaat ggacagagtt tcatttgtaa
1621 aacttcttat tgaaaacgga gtaagcatgc ataaattcct taccattccc agactggaag
1681 aactttataa cactaaacaa ggtccaacca atccaatgtt gttccatctc attcgggatg
1741 tcaagcaggg taatctcccc cggggtaca agatcacttt aattgatata ggacttgtga
1801 ttgagtatct catgggagga acctaacgat gcacatacac acgaaaacgt tttcgattga
1861 tatataatag tcttggtgga aataaccgga ggtcaggtcg aaatacctcc agcagcaccc
1921 ctcagttgcg aaagagtcat gaaacttttg gcaatagagc tgataaaaag gaaaaaatga
1981 gacacaatca tttcattaaa acagcccaac cctacagacc aaagatggat gcatctatgg
2041 aagaaggaaa gaagaaaaga accaaagatg aaattgtaga tatagatgat ccagagacca
2101 agcgctttcc ttatcctctt aatgaattat taatttgggc ttgccttatg aagaggcagg
2161 tcatggcccg cttttttatg cagcatggtt aagaatcaat ggctaaagca ttagttgcct
2221 gtaaaatcta tcgttcaatg gcttatgagg caaagcagag tgacctggta gatgatactt
2281 cagaggaact gaagcagtat tccaatgatt ttggccaact ggcagttgaa ttactggaac
2341 agtccttcag acaggatgaa acgatggcta tgaaattact cacttatgaa ctcaaaaact
2401 ggagtaattc aacctgcctc aagttagcag tttcttcaag acttagacct tttgtagctc
2461 acacttgtac acagatgttg ttatctgata tgtggatggg acggctgaat atgagaaaaa
2521 attcctggta taaggtcata ttaagcattt tagttccacc tgccatatta atgctagagt
2581 ataaaaccaa ggctgaaatg tccatatcc cacaatctca agatgctcat caaatgacga
2641 tggaggatag tgaaacaat tttcacaaca taacagaaga gatacccatg gaagtattta
2701 aagaagtaaa gattttggac agcagtgatg gaaagaatga aatggagata catattaaat
2761 caaaaaagct tccaatcaca cgaaaatttt atgccttta tcatgcacca attgtaaagt
2821 tctggtttaa cacattgca tatttaggat ttctgatgct ttatacattt gtagttcttg
2881 taaaaatgga acagttacct tcagttcaag aatggattgt tatcgcttat atttttacct
2941 atgctattga aaaagtccgt gaggtcttca tgtctgaagc tgggaaaatc agccagaaga
3001 ttaaagtatg gtttagtgac tacttcaatg tcagtgacac aattgccatc atttcttttct
3061 ttgttggatt tggactaaga tttggagcaa aatggaacta tattaatgca tatgataatc
3121 atgtttttgt ggctgaagaa ttaatttact gtcttaatat aatattttgg tatgtgcgtt
3181 tgctagactt tctagccgta aatcaacagg caggaccta tgtaatgatg attggaaaaa
3241 tggtggccaa tatgttctac attgtagtga taatgctct tgtattgctt agttttggtg
3301 ttcccagaaa agcaatactt tatccacatg aagaaccatc ttggtctctt gctaaagata
3361 tagttttctca tccatactgg atgattttg gtgaagttta tgcatatgaa attgatgtgt
3421 gtgcaaatga ctccactctc ccgacaatct gtggtcctgg aacttggttg actccatttc
3481 ttcaagcagt ctacctcttt gtacagtata tcattatggt taatctcctc atccattttt
3541 tcaataatgt atatttacaa gtgaaggcaa tttccaatat tgtatggaag tatcagcggt
```

Fig. 17(A)

```
3601 atcattttat tatggcttat catgaaaaac cagtcctgcc tcctcctctt atcatcctca
3661 gccatatagt ttcactgttt tgctgtgtat gcaaaagaag aaagaaagat aagacttccg
3721 atgggccaaa acttttctta acagaagaag atcaaaagaa actccatgat tttgaagagc
3781 agtgtgttga gatgtacttt gatgagaaag atgacaaatt caattctggg agtgaagaga
3841 gaatccgggt cacttttgaa agagtggagc agatgagcat tcagattaaa gaagttggag
3901 atcgtgtcaa ctacataaaa agatcattac agtctttaga ttctcaaatt ggtcatctgc
3961 aagatctctc agccctaaca gtagatacat tgaaaacact tacagcccag aaagcttcag
4021 aagctagtaa agtgcacaat gagatcacac gagaattgag tatttccaaa cacttggctc
4081 agaatcttat tgatgatgtt cctgtaagac ctttgtggaa gaaacctagt gctgtaaaca
4141 cactgagttc ctctcttcct caaggtgatc gggaaagtaa taatcctttt ctttgtaata
4201 ttttatgaa agatgaaaaa gaccccccaat ataatctgtt tggacaagat ttgcccgtga
4261 taccccagag aaaagaattc aacattccag aggctggttc ctcctgtggt gccttattcc
4321 caagtgctgt ttctccccca gaattacgac agagacgaca tggggtagaa atgttaaaaa
4381 tatttaataa aaatcaaaaa ttaggcagtt cacctaatag ttcaccacat atgtcctccc
4441 caccaaccaa attttctgtg agtaccccat cccagccaag ttgcaaaagt cacttggaat
4501 ccacaaccaa agatcaagaa cccatttct ataaagctgc agaaggggat aacatagaat
4561 ttggagcatt tgtgggacac agagatagta tggacttaca gaggtttaaa gaaacatcaa
4621 acaaaataag agaactgtta tctaatgata ctcctgaaaa cactctgaaa catgtgggtg
4681 ctgctggata tagtgaatgt tgtaagactt ctacttctct tcactcggtg caagcagaaa
4741 gctgtagtga aagagcgtcg acggaagact ctccagaagt cgattctaaa gcagctttgt
4801 taccggattg gttacgagat agaccatcaa acagagaaat gccatctgaa ggaggaacat
4861 taaatggtct tgcttctcca tttaagcccg ttttggatac aaattactat tattcagctg
4921 tggaaagaaa taacctgatg aggttgtcac agagtattcc cttcgttcct gtacctccac
4981 gaggcgagcc tgtcacagtg tacgtctgg aggagagttc tcccagtata ctgaataaca
5041 gcatgtcttc atggtctcag ctaggcctct gtgccaaaat tgagttttta agtaaagagg
5101 aaatgggagg tggtttacga agagcagtca aagtgctgtg tacctggtca gagcacgata
5161 tcctgaagtc agggcatctc tatatcatta agtcatttct tcctgaggtg ataaacacat
5221 ggtcaagcat ttataaagaa gatacggttc tacatctctg tctcagagaa atacaacaac
5281 agagagcagc acaaaagctc acatttgcct ttaatcagat gaaacccaaa tccataccat
5341 attctccaag gttccttgaa gttttcctgt tgtactgcca ttcagcaggg cagtggtttg
5401 ctgtagaaga gtgcatgact ggtgaattta gaaaatacaa caacaataat ggtgatgaaa
5461 tcattcctac aaatactcta gaagagatca tgctagcctt tagccactgg acctatgaat
5521 ataccagagg ggagttactg gtacttgacc tacaaggagt gggagaaaac ttgactgacc
5581 catctgtaat aaaagctgaa gaaaaaagat cctgtgacat ggttttttggc cctgccaatc
5641 taggagaaga tgcaataaaa aacttcagag ccaaacatca ctgtaaattct tgctgtcgaa
5701 agcttaaact tccagatttg aagaggaatg actacacgcc tgataaaatt atatttcctc
5761 aggatgagtc atcagatttg aatcttcaat ctggaaattc caccaaagaa tcagaagcaa
5821 caaattctgt tcgtctgatg ttatagtgct gagtcattgg ttttgccta cacttcacaa
5881 aagtgtaact gtcagttttc ctttcgggg aattgatgat ataggaagat gtgtgcaaaa
5941 tgagctgct ggccccacac atagtctgga ggtaatgttc tcattgaaaa acgcctggag
6001 gctgcagatg acagctggaa agtgctagct ggcagagagt cagtgctctc ggctggtgaa
6061 gggcgggaac cttgctgctg agagtggtgg ttctctcacc tggtgcagga ccattaacca
6121 aagtcaagtc ttcagatttg attggctgct cagtcacagc cattcagcta aggaaactaa
6181 attgcgcagc ttttaaatg gctgaagtct tcctcagttt gtgctctatg ataatgatgt
6241 tagctctcaa ctaggtgttt gtggccacgg gaaactact cctttacaatt ttgcttcaca
6301 ggcatgttac aaagcctgca ctgaaaaccg tttgtcttcc ctctctccct ccctcttttc
6361 cctgtagtat tgaggatcaa acccagggcc tcatgaagac catttttctaa gagacatttt
6421 atttaagaat caactataga gtctatgttt atggatacag ccagttttttg ttaaacaaaa
6481 cctgaattgt gcaaaagggt tttttaacat ttatcaatgt taagtaaaag aaagccatga
6541 taaataagaa ttaactcact gttcaatggt tgtttcctgt gaggaaggtt acagttgtaa
6601 cagcctgcag ttgcatacat ctccaaagat ttacagactt agtgtatcaa atcagagtgt
6661 catgtgagct ctcacattga aaattctata ggaatgtgtc aatgtgaatt ctatttctgg
6721 tacttaagaa atcagttgtt ggattatcct tatacagtat agggagatca caatacaact
6781 ttatgccaat aaaatctaac ttaattgccc agatattttt gcatatttag caacaagaaa
6841 agctatcat ttgactcaag tttatgctt tctctttctt ttcatttcct aggtactaat
6901 tttaatttt atttggaagg agcagtgtaa agcttacttg tattcaatag tgtatctcat
6961 agatacagac aaggccgcag agataagctg ttaaatagtg tttaatgttg atgtggagag
7021 aaaggtgtat tacttaaaaa tactatacca tatacgtttt gtatatcatt aaatctttaa
7081 aagaaattaa atttattctt gtttamaraa aaaaaaaaaa aaa
```

Fig. 17(B)

METHODS OF SCREENING FOR LTRPC7 MODULATORS

CROSS REFERENCE TO RELATED APPLICATIONS

This application is a continuation of U.S. application Ser. No. 10/008,539, filed Nov. 13, 2001, which claims the benefit under 35 U.S.C. §119(e) of U.S. Provisional Application No. 60/248,235, filed Nov. 13, 2000 and U.S. Provisional Application No. 60/254,468, filed Dec. 8, 2000, each of which is hereby incorporated by reference in its entirety.

FIELD OF THE INVENTION

The present invention relates to the identification and isolation of a novel family of ATP regulated calcium transmembrane channel polypeptides designated herein as "LTRPC7" (Long Transient Receptor Potential Channel). Channels comprising these polypeptides close in response to concentrations of cytoplasmic ATP in the millimolar range, are subject to inhibition by high intracellular levels of calcium and/or magnesium, and do not respond to depletion or reduction in intracellular calcium stores. The invention further relates to the recombinant nucleic acids that encode LTRPC7 and the methods of utilizing LTRPC7 to bind candidate bioactive agents for modulating LTRPC7 activity and for measuring LTRPC7 permeability to multivalent cations. The invention further relates to methods of modulating the cellular expression of the recombinant nucleic acids that encode LTRPC7.

BACKGROUND OF THE INVENTION

Ion channels are transmembrane multi-subunit proteins embedded in the cellular plasma membranes of living cells which permit the passage of specific ions from the extracelluar side of the plasma membrane to the intracellular region of the cell. Specific ion transport is facilitated by a central aqueous pore which is capable of opening and closing due to changes in pore conformation. When the ion gate is open, ions flow freely through the channel. When the ion gate is closed, ions are prevented from permeating the channel. Ion channels are found in a multitude of multicellular eukaryotic species and in a myriad of different cell types. Ion channels may be either voltage-gated or ligand-gated. Channel gating is the process by which a particular channel is either open or closed. An ion channel may be capable of occupying a range of different "open" or "closed" states. The gating process may therefore require a particular sequence of transition states or inclusion of alternative transition states before a channel attains a particular level of gating. The gating process is modulated by a substance or agent, which in some way alters or affects the manner in which the channel opens or closes. A channel may be gated by a ligand such as a neurotransmitter, an internal primary or secondary messenger, or other bioactive agent. The ligand either attaches to one or more binding sites on the channel protein or attaches to a receptor that is associated with the channel. If the channel is voltage-gated, changes in the membrane potential trigger channel gating by conformational changes of charged elements within the channel protein. Whether a channel is ligand-gated or voltage-gated, a change in one part of the channel produces an effect in a different part of the channel which results in the opening or closing of a permeant pathway.

SUMMARY OF THE INVENTION

The invention relates to the identification, isolation and use of a novel family of ATP regulated calcium transmembrane channel polypeptides designated herein as "LTRPC7" (Long Transient Receptor Potential Channel) which close in response to increasing concentrations of cytoplasmic ATP in the millimolar range, are subject to inhibition by high intracellular levels of calcium and/or magnesium, and do not respond to depletion or reduction in intracellular calcium stores. The invention further relates to the recombinant nucleic acids that encode LTRPC7 and the methods of utilizing LTRPC7 to bind candidate bioactive agents for modulating LTRPC7 activity and for measuring LTRPC7 permeability to multivalent cations. The invention further relates to methods of modulating the cellular expression of the recombinant nucleic acids that encode LTRPC7.

One embodiment of the invention provides methods for screening for candidate bioactive agents that bind to LTRPC7. In this method, LTRPC7, or a fragment thereof, is contacted with a candidate agent, and it is determined whether the candidate agent binds to LTRPC7. An embodiment of the invention provides for contacting LTRPC7 with a library of two or more candidate agents and then determining the binding of one or more of the candidate agents to LTRPC7.

In a further embodiment, LTRPC7 comprises an ion channel and the candidate agent(s) that bind the LTRPC7 channel modulate the multivalent cationic permeability of the LTRPC7 channel. In some embodiments, the candidate agent(s) that bind LTRPC7, open the LTRPC7 channel. In still another embodiment, the candidate agents that bind LTRPC7, close the LTRPC7 channel. In still another embodiment of the invention, the multivalent cations which permeate LTRPC7 include $Ca^{2+}$, $Mn^{2+}$, $Zn^{2+}$, $Ni^{2+}$, $Ba^{2+}$, $Sr^{2+}$, $Co^{2+}$, $Cd^{2+}$, and $Mg^{2+}$.

In some embodiments the LTRPC7 channel is in a recombinant cell which comprises a recombinant nucleic acid encoding LTRPC7, an inducible promoter which is operably linked to the recombinant nucleic acid, and a multivalent cation indicator, such as fura-2. The recombinant cell is induced to express LTRPC7 and it is then contacted with a solution comprising a multivalent cation together with a candidate agent. In another embodiment, the recombinant cell is contacted with a candidate agent prior to being contacted with a multivalent cation. Intracellular levels of the multivalent cation are detected using the multivalent cation indicator. An embodiment of the invention provides for contacting the recombinant cell with a multivalent cation solution comprising $Ca^{2+}$, $Mn^{2+}$, $Zn^{2+}$, $Ni^{2+}$, $Ba^{2+}$, $Sr^{2+}$, $Co^{2+}$, $Cd^{2+}$, and $Mg^{2+}$. In some embodiments, the candidate agent increases the multivalent cation permeability of the LTRPC7 channel. In other embodiments, the candidate agent decreases the multivalent cation permeability of the LTRPC7 channel. In a preferred embodiment, the multivalent cation indicator comprises a fluorescent molecule. In a more preferable embodiment of the invention, the multivalent cation indicator comprises fura-2. In an alternate embodiment, the production of LTRPC7 channel is induced and the multivalent cation intracellular levels are detected in the presence of a candidate agent. That level is compared to the multivalent cation intracellular level detected in an uninduced recombinant cell either in the presence or absence of a candidate agent.

It is another object of the invention to provide methods for measuring the multivalent ion permeability of an LTRPC7 channel. In this method, a recombinant cell is provided, which comprises a recombinant nucleic acid encoding LTRPC7, a promoter, either constitutive or inducible, preferably inducible, which is operably linked to the recombinant nucleic acid, and an intracellular cation indicator. The recombinant cell is contacted with a solution comprising a multivalent cation that selectively interacts with the indicator to generate a signal. Intracellular levels of the multivalent cation are then measured when LTRPC7 is expressed by detecting the indicator signal. This measurement is compared to endogenous levels in which recombinant LTRPC7 is not expressed.

In a broader embodiment, the cell is not limited to a recombinant LTRPC7 expressing cell, but can comprise any cell capable of being used with any recombinantly expressed channel protein for determining agents which modulate the activity of the channel. The expression of the recombinant channel is preferably under the control of an inducible promoter.

In a preferred embodiment the multivalent cation indicator comprises a fluorescent molecule such as fura-2. In yet a further embodiment of the invention the multivalent cation which selectively interacts with the cation indicator is $Ca^{2+}$, $Mn^{2+}$, $Zn^{2+}$, $Ni^{2+}$, $Ba^{2+}$, $Sr^{2+}$, $Co^{2+}$, $Cd^{2+}$, and $Mg^{2+}$. In some embodiments the modulating activity of a candidate bioactive agent which contacts the recombinant cell together with the multivalent cation agent increases the multivalent cation permeability of the LTRPC7 channel, in others it decreases it. In further embodiments the modulating activity of a candidate bioactive agent which contacts the recombinant cell prior to contact with the multivalent cation agent increases the multivalent cation permeability of the LTRPC2 channel, in others it decreases it.

It is further an object of the invention to provide methods for screening for candidate bioactive agents that are capable of modulating expression of LTRPC7. In this method, a recombinant cell is provided which is capable of expressing a recombinant nucleic acid encoding LTRPC7, a fragment thereof, including in some embodiments the 5' and/or 3' expression regulation sequences normally associated with the LTRPC7 gene. The recombinant cell is contacted with a candidate agent, and the effect of the candidate agent on LTRPC7 expression is determined. In some embodiments, the candidate agent may comprise a small molecule, protein, polypeptide, or nucleic acid (e.g., antisense nucleic acid). In another embodiment of the invention, LTRPC7 expression levels are determined in the presence of a candidate bioactive agent and these levels are compared to endogenous LTRPC7 expression levels.

Another aspect of the invention is a recombinant LTRPC7 protein or fragment thereof having the sequence of amino acids from 1 through about 1865 of SEQ ID NO:1 (FIG. 12) or having the sequence of amino acids from 1 through about 1863 of SEQ ID NO:4 (FIG. 15), where LTRPC7 is a transmembrane channel polypeptide which closes in response to concentrations of cytoplasmic ATP in the millimolar range, is subject to inhibition by high intracellular levels of calcium, and does not respond to depletion or reduction in intracellular calcium stores.

Another aspect of the invention is an isolated recombinant nucleic acid molecule having at least 80% sequence identity to a DNA molecule encoding a recombinant LTRPC7 protein or fragment thereof having the sequence of amino acids from 1 through about 1865 of SEQ ID NO:1 (FIG. 12) [GenBank Accession No. AAK44211] or having the sequence of amino acids from 1 through about 1863 of SEQ ID NO:4 (FIG. 15) [GenBank Accession No. AAK50377]. An embodiment of the invention is a recombinant nucleic acid molecule comprising sequences from about 272 through about 5869 of SEQ. ID NO:3 (FIG. 14) [GenBank Accession No. AY032950] or a recombinant nucleic acid molecule comprising sequences from about 255 through about 5846 of SEQ. ID NO:6 (FIG. 17) [GenBank Accession No. AY032951].

Another aspect of the invention is an isolated recombinant nucleic acid molecule comprising an LTRPC7 gene comprising the sequence from 1 through about 7259 (SEQ ID NO:3) [GenBank Accession No. AY032950], wherein said recombinant nucleic acid molecule encodes a recombinant LTRPC7 protein or any preferred fragments thereof having the sequence of amino acids from 1 through about 1865 of FIG. 12 (SEQ ID NO:1) or a sequence which is at least 80% identical to said protein sequence.

Another aspect of the invention is an isolated recombinant nucleic acid molecule comprising an LTRPC7 gene comprising the sequence from 1 through about 7123 (SEQ ID NO:6) [GenBank Accession No. AY032951], wherein said recombinant nucleic acid molecule encodes a recombinant LTRPC7 protein or any preferred fragments thereof having the sequence of amino acids from 1 through about 1863 of FIG. 15 (SEQ ID NO:4) or a sequence which is at least 80% identical to said protein sequence.

In a further embodiment of the invention, LTRPC7 comprises polypeptides having an amino acid sequence comprising from 1 through about 1865 amino acids having SEQ ID NO:1 (FIG. 12). In a further embodiment, LTRPC7 is encoded by nucleic acid sequences of nucleotides comprising nucleotides from about 272 through about 5869 of SEQ ID NO:3 (FIG. 14).

In a further embodiment of the invention, LTRPC7 comprises polypeptides having an amino acid sequence comprising from 1 through about 1863 amino acids having SEQ ID NO:4 (FIG. 15). In a further embodiment, LTRPC7 is encoded by nucleic acid sequences of nucleotides comprising nucleotides from about 255 through about 5846 of SEQ ID NO:6 (FIG. 17).

BRIEF DESCRIPTION OF THE DRAWINGS

FIG. 1 depicts that LTRPC7 is a novel ubiquitously expressed member of the LTRPC7 family of putative ion channels.

FIG. 2 demonstrates that LTRPC7 is fundamental to cellular function. Inducible LTRPC7 expression in HEK-293 cells and Cre/loxP-mediated inducible disruption of LTRPC7 are in the chicken B cell line DT-40.

FIG. 3 demonstrates that LTRPC7 is a cation channel. HEK-293 cells were induced to express a FLAG-LTRPC7 construct by tetracycline for 24 h before patch-clamp experiments.

FIG. 4 depicts the permeation and block of LTRPC7 by divalent ions. HEK-293 cells were induced to express a FLAG-LTRPC7 construct by tetracycline for 24 h before patch-clamp experiments.

FIG. 5 demonstrates that LTRPC7 is activated by ATP depletion. HEK-293 cells were induced to express a FLAG-LTRPC7 construct by tetracycline for 24 h before patch-clamp experiments. FIG. 5(B) shows the average changes of maximum outward current measured at +80 mV as a function of intra-pipette ATP levels. The change in current size was analyzed by subtracting the first data trace acquired after whole-cell establishment from the one elicited at 300 s. Note that with 6 mM ATP, the currents are actually decreasing after break-in.

FIG. 7 depicts the equimolar substitution of 10 mM $Ca^{2+}$ by transition metals. Whole-cell currents were recorded in HEK-293 cells over-expressing LTRPC7 kept in a bath containing 10 Mm $Ca^{2+}$, without $Mg^{2+}$, and exposed for 60 s to an otherwise identical external solutions where 10 mM $Ca^{2+}$ was equimolarly replaced by the test cation. Average inward and outward currents at −80 and +80 mV were scaled so that the inward and outward current amplitudes immediately preceding the solution change were set to 1. In FIG. 7(C), 10 mM $Ba^{2+}$ (n=6), 10 mM $Sr2+$(n=3) and 10 mM $Cd\ 2+$(n=3) caused a slight to moderate increase of the inward current, and increase of the outward current.

FIG. 8 depicts the permeation of divalent trace metals in isotonic solutions. Whole-cell currents were recorded in HEK-293 cells over-expressing LTRPC7 in standard external solution containing 1 mM $Ca^{2+}$ and 2 mM $Mg^{2+}$, and subsequently exposed to an isotonic solution of the test cation for 60 s. Average inward and outward currents at −80 and +80 mV were scaled so that the inward and outward current amplitudes immediately preceding the solution change were set to 1.

FIG. 9 depicts the permeation of toxic divalent metals in isotonic solutions. Whole-cell currents were recorded in HEK-293 cells over-expressing LTRPC7 in standard external solution containing 1 mM $C^{2+}$ and 2 mM $Mg^{2+}$, and subsequently exposed to an isotonic solution of the test cation for 60 s. Average inward and outward currents at −80 and +80 mV were scaled so that the inward and outward current amplitudes immediately preceding the solution change were set to 1.

FIG. 10 depicts the permeation and block by trivalent metal ions. Average inward and outward currents at −80 and +80 mV, respectively, recorded in HEK-293 cells over-expressing LTRPC7 in standard external solution containing 10 mM $Ca^{2+}$, without $Mg^{2+}$ (FIGS. 10(A) and 10(B)).

FIG. 11 demonstrates that LTRPC7 is an influx pathway for $Ca^{2+}$ and $Mn^{2+}$. Simultaneous whole-cell patch-clamp recordings of MagNuM and fura-2 measurements of $[Ca^{2+}]i$ in HEK-293 cells over-expressing LTRPC7. FIG. 11(A) shows that average inward and outward MagNuM currents at −80 and +80 mV, respectively, in cells perfused with Cs-glutamate-based internal solution in the absence of Mg.ATP (filled circles, n=6) and with 3 mM Mg.ATP (open circles, n=6). Note the different Y-axis scaling. FIG. 11(B) shows a representative high-resolution current record obtained in response to a 50-ms voltage ramp from −100 to +100 mV, showing the characteristic signature of MagNuM (strong outward rectification at potentials above +50 mV) in a cell dialysed with 0 Mg.ATP. FIG. 11(C) shows the average intracellular $Ca^{2+}$ signals recorded from cells patched in (A) showing a steady rise in $[Ca^{2+}]i$ in the absence of Mg.ATP. In contrast, $[Ca^{2+}]i$ remains at steady basal levels when LTRPC7 is blocked by 3 mM Mg.ATP or in control HEK cells not over-expressing the channel (dotted line, n=5). FIG. 11(D) shows the average fura-2 fluorescence at 360 nm excitation in HEK-293 cells induced to over-express LTRPC7 (n=5) and transfected cells that remained uninduced (n=5).

FIG. 12 shows the amino acid sequence of a recombinant LTRPC7 protein comprised of sequences from 1 through about 1865 (SEQ ID NO:1).

FIGS. 13(A) and (B) shows the recombinant nucleic acid molecule of an LTRPC7 cDNA encoding sequence (SEQ ID NO:2).

FIGS. 14(A) and (B) shows the recombinant nucleic acid molecule of an LTRPC7 gene comprised of nucleic acid sequences from 1 through about 7,259 (SEQ ID NO:3).

FIG. 15 shows the amino acid sequence of a recombinant LTRPC7 protein comprised of sequences from 1 through about 1863 (SEQ ID NO:4).

FIGS. 16(A) and (B) shows the recombinant nucleic acid molecule of an LTRPC7 cDNA encoding sequence (SEQ ID NO:5).

FIGS. 17(A) and (B) shows the recombinant nucleic acid molecule of an LTRPC7 gene comprised of nucleic acid sequences from 1 through about 7,123 (SEQ ID NO:6).

DETAILED DESCRIPTION OF THE PREFERRED EMBODIMENTS

Figure 1A:
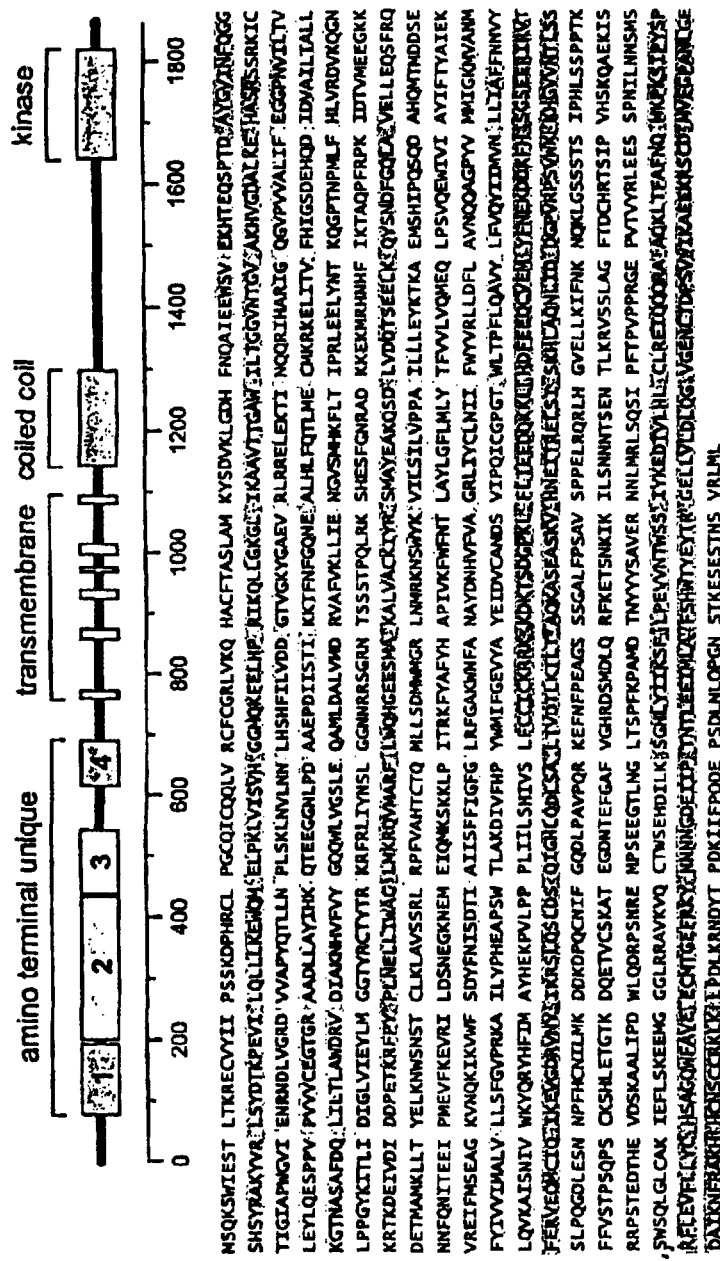
FIG. 1(A) is a schematic of LTRPC7 with amino terminal unique regions 1-4 (these regions are defined by their particularly high homology throughout the LTRPC family, and because the sequences between them are of variable length and level of homology in different LTRPC members), transmembrane domain regions (spans are based on Tmpred and hydophobicity analyses), coiled coil region (approximate region based on COILS output graph), and the MHCK/EEF2α kinase homology domain (from BLAST alignments). The predicted protein sequences of human LTRPC7 is also presented [SEQ ID NO. 1]
Figures 1B, 1C:
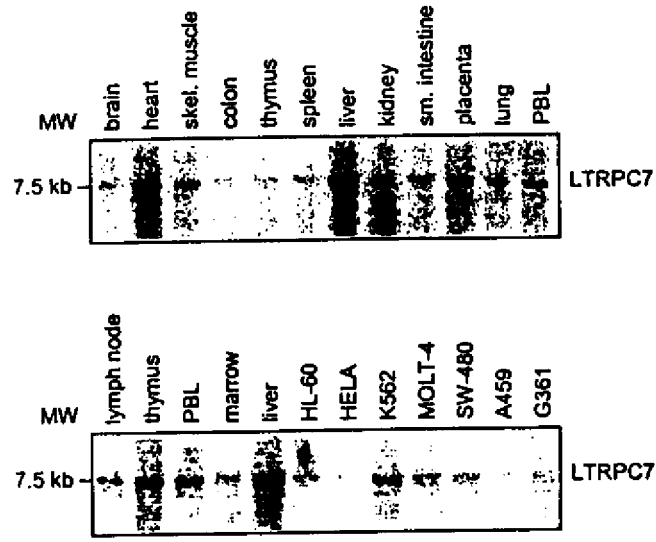
FIG. 1(B) is a Northern blot analysis of LTRPC7 transcript expression in various human tissues and cell lines.
FIG. 1(C) is an RT-PCR analysis of LTRPC7 transcript expression in various human tissues and cell lines. + indicates a band of the correct size was present, ++ indicates an intense band of the predicted size was present. Specificity of the PCR assay was confirmed by the cloning of partial LTRPC7 cDNA's from the kidney, spleen, and leukocyte libraries.
Figure 2A:
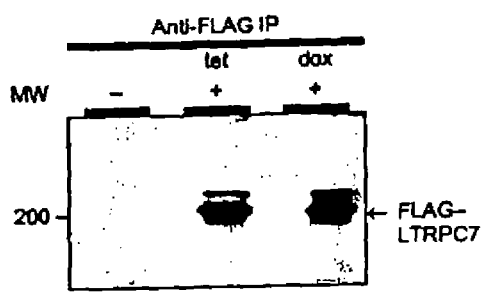
In FIG. 2(A) HEK-293 cells expressing the tet repressor protein were transfected with a plasmid containing a FLAG-LTRPC7 construct under control of a tet-inducible full CMV promoter. SDS-PAGE analysis of anti-FLAG immunoreactive proteins before (left lane) or after 24 hours of either tetracycline or doxycycline treatment (middle and right lanes, respectively).
Figure 2B:
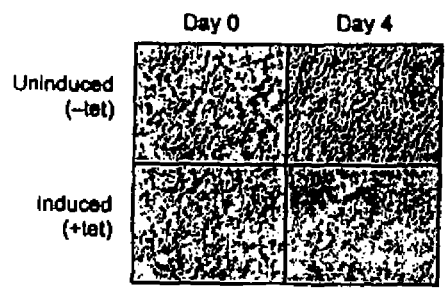
FIG. 2(B) are contrast images of representative areas of tissue culture plates containing cells from the HEK-293 cell line characterized above at time 0 or 4 days after treatment or not with tetracycline.
Figure 2C:
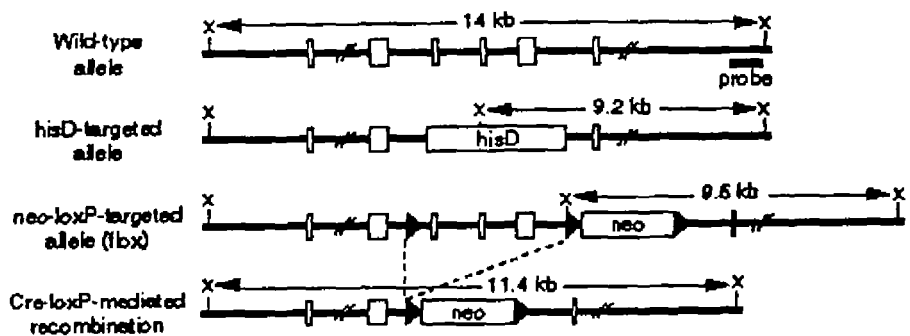
FIG. 2(C) is the structure of the wild-type and mutated LTRPC7 alleles are shown. Restriction enzyme sites (X, XbaI), the probe of Southern blot analysis (solid bar), exons (open rectangle), and loxP sites (solid triangle) are indicated. Three exons including a part of putative transmembrane region (corresponding to mouse LTRPC7 amino acid residues 997-1158 in FIG. 1) were replaced with hisD cassette in hisD-targeted allele and were flanked by two loxP sequences in neo-loxP-targeted allele. XbaI fragments detected by the probe are shown for wild-type and mutated alleles.
Figure 2D:
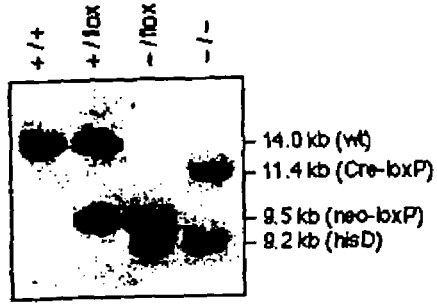
FIG. 2(D) is a Southern blot analysis of XbaI digested DNA prepared from wild-type and mutant DT-40 cells. For the inducible gene disruption by the Cre/loxP-mediated recombination, cells that were cultured in medium containing 200 nM tamoxifen for 48 hr were subjected to Southern blot analysis (lane 4).
Figure 2E:
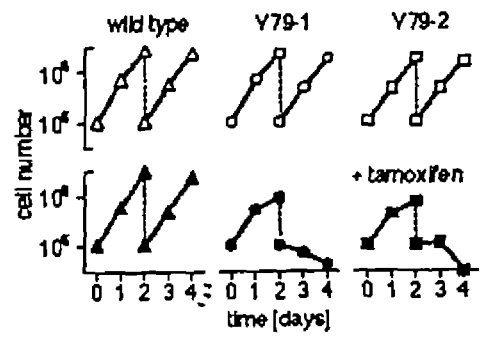
FIG. 2(E) shows the effect of LTRPC7 inactivation on cell proliferation. DT-40 wild type and mutant clones (V79-1 and V79-2) harboring hisD- and neo-loxP-targeted alleles (1×105 cells/ml) were cultured either in the absence (open circle) or presence (open triangle) of 200 nM tamoxifen. Cell numbers were adjusted to 1×105 cells/ml 2 days after cultivation. Viable cells were monitored daily by the trypan blue exclusion method.
Figure 3A:
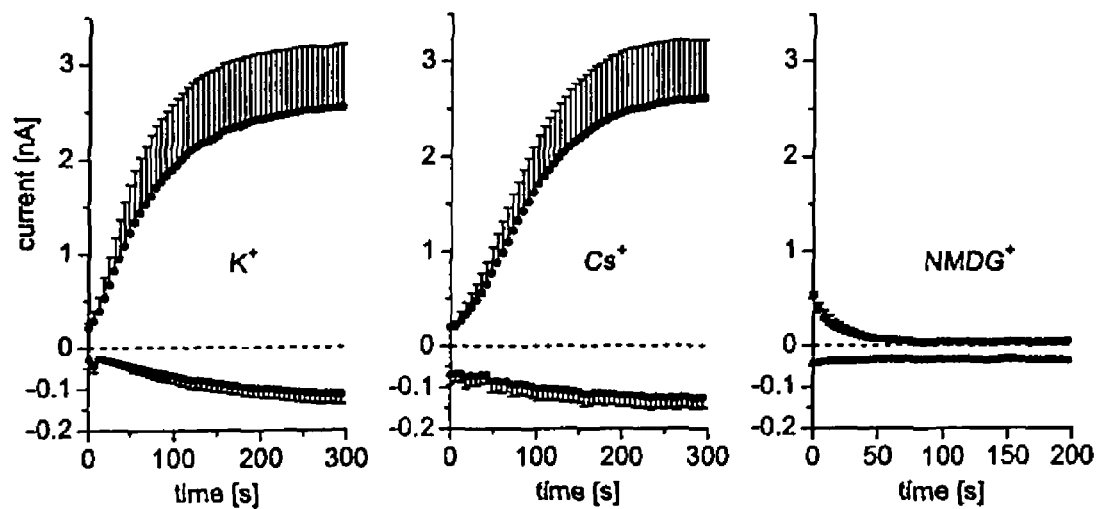
FIG. 3(A) shows the average inward and outward currents carried by recombinant LTRPC7 at −80 and +80 mV, respectively. Cells perfused with standard K-glutamate (left panel, n=5+/−sem) or Cs-glutamate internal solution (middle panel, n=7+/−sem) containing 0 mM ATP activated an ionic conductance that was characterized by an outwardly rectifying I/V relationship (cf. corresponding panels in FIG. 3(B)). This current was absent when replacing K or Cs with NMDG-chloride (right panel, n=3+/−sem).
Figure 3B:
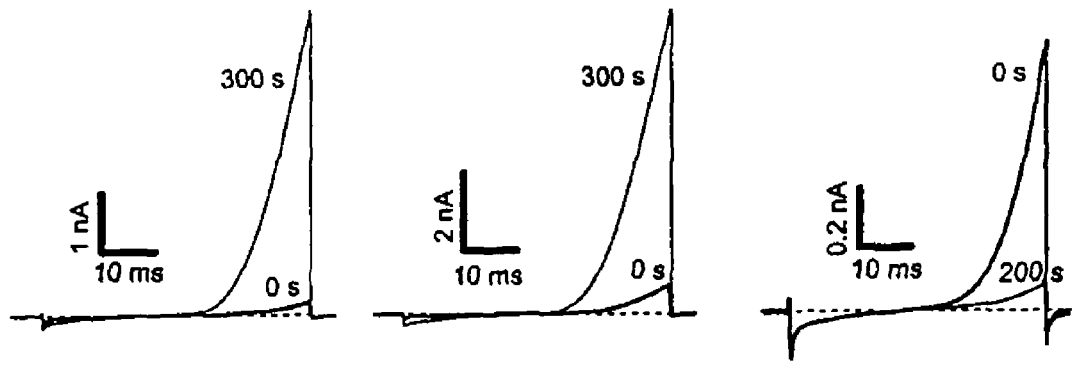
FIG. 3(B) shows representative, high-resolution current records in response to voltage ramps of 50 ms duration that ranged from −100 mV to +100 mV respectively. Current records were taken from cells that were subject to the experimental conditions described in FIG. 3(A), with K-based (left panel), Cs-based (middle panel), or NMDG-based (right panel) internal solutions. Note the decreased current amplitude at 200 s in cells perfused with NMDG-chloride internal solution.
Figure 4A:
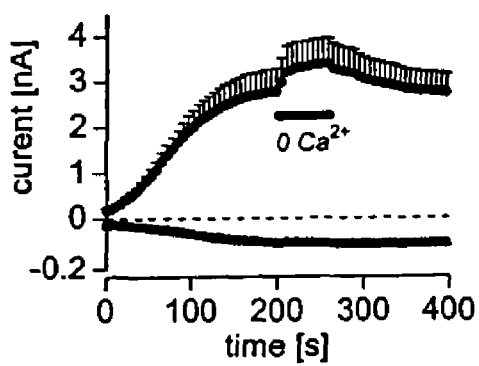
FIG. 4(A) shows the average inward and outward currents carried by recombinant LTRPC7 at −80 and +80 mV, respectively (n=5). Application of $Ca^{2+}$-free extracellular solution slightly increased outward currents. Application time is indicated by the black bar.
Figure 4B:
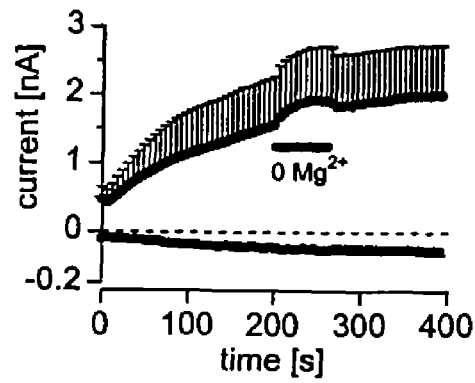
FIG. 4(B) shows the average inward and outward currents carried by recombinant LTRPC7 at −80 and +80 mV, respectively (n=5). Application of $Mg^{2+}$-free extracellular solution slightly increased outward currents. Application time is indicated by the black bar.
Figure 4C:
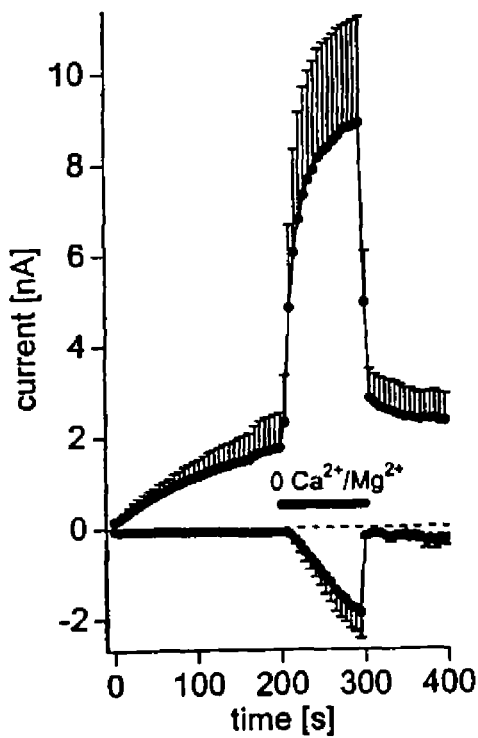
FIG. 4(C) shows the average inward and outward currents carried by recombinant LTRPC7 at −80 and +80 mV, respectively (n=5). Removal of both $Ca^{2+}$ induced a large increase of both inward and outward currents. Application time is indicated by the black bar.
Figure 4D:
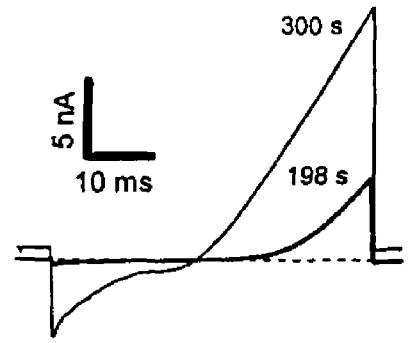
FIG. 4(D) depicts representative, high-resolution current records in response to voltage ramps of 50 ms duration that ranged from −100 mV to +100 mV. Superimposed traces were taken from cells that were subject to the experimental conditions described in FIG. 4(C), and represent currents elicited just before divalent-free application (198 s) and just before readmission of divalents (300 s). Note the linearization of outward and inward rectification of inward currents.
Figure 4E:
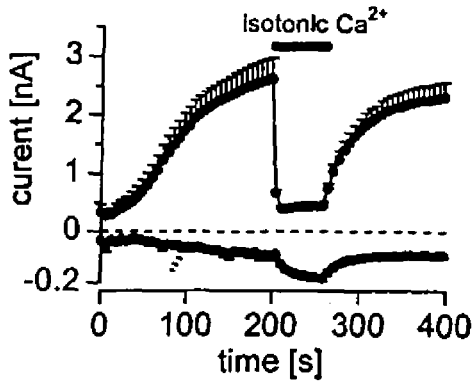
FIG. 4(E) shows the average inward and outward currents carried by recombinant LTRPC7 at −80 and +80 mV, respectively (n=5). Application of isotonic $CaCl_2$ (120 mM, 320 mOsm) enhanced inward currents and strongly inhibited outward currents. Application time is indicated by the black bar.

The invention relates, in part, to methods useful in identifying molecules, which bind LTRPC7, which modulate LTRPC7 ion channel activity, and/or which alter expression of LTRPC7 within cells. The LTRPC7 channels as described herein comprise LTRPC7 polypeptides, which are in turn encoded by LTRPC7 nucleic acids. The ion channels described herein are preferably formed in HEK 293 cells and comprise one or more novel LTRPC7 polypeptides, which exhibit one or more of the unique LTRPC7 properties described herein.

As described herein, the term "LTRPC7" (Long Transient Receptor Potential Channel) refers to a member of the novel family of ATP regulated calcium transmembrane channel polypeptides. The polypeptides are also defined by their amino acid sequence, the nucleic acids which encode them, and the novel properties of LTRPC7. Such novel properties include closure of the LTRPC7 channel in response to concentrations of intracellular ATP in the millimolar range, inhibition of the LTRPC7 channel in response to high intracellular levels of calcium and/or magnesium, and non-responsiveness of the LTRPC7 channel to a depletion or reduction in intracellular calcium stores. An additional novel property of the LTRPC7 channel is its permeability to divalent heavy metal ions such as $Mn^{2+}$, $Zn^{2+}$, $Ni^{2+}$, $Ba^{2+}$, $Sr^{2+}$, $Co^{2+}$, and $Cd^{2+}$. Intracellular concentrations of ATP in the 6-10 millimolar range cause the LTRPC7 channel to close, while intracellular concentrations of ATP in the 0-4 millimolar range cause the LTRPC7 channel to reopen.

The LTRPC7 polypeptides and channels are functionally distinct from the "SOC" (Store Operated Channels) and "CRAC" (Calcium Release Activated Channels) polypeptides and channels, disclosed in "Characterization of a Calcium Family," WO 00/40614, the disclosure of which is expressly incorporated herein by reference. The SOC and CRAC proteins channels "may be activated upon depletion of $Ca^{2+}$ from intracellular calcium stores" (see WO 00/40614 at page 2) and are further "subject to inhibition by high levels of intracellular calcium" (see WO 00/40614 at page 10). Although the LTRPC7 polypeptides of the invention form channels that are subject to inhibition by high intracellular levels of calcium, the LTRPC7 channel is not activated by the depletion or reduction in intracellular calcium stores and closes in response to intracellular ATP concentrations in the millimolar range. SOC and CRAC are not regulated in this manner.

The LTRPC7 polypeptide is a novel member of the LTRPC family. The specific sequence disclosed herein as SEQ ID NO:1 (FIG. 12) was derived from human spleen cells and the specific sequence disclosed herein as SEQ ID NO:4 (FIG. 15) was derived from mouse monocyte cells. However, LTRPC7 is believed to be broadly expressed in tissues from mammalian species and other multicellular eukaryotes, such as *C. elegans*.

Insight into LTRPC7 function is also likely to be of significance to the understanding of the physiology of severe metabolic stress conditions (e.g., long term hypoxia or hypoglycemia), through which ATP can be depleted to an extent capable of activating potentially damaging levels of LTRPC7-mediated $Ca^{2+}$ entry.

Our functional analysis of LTRPC7 suggest that it acts as a ubiquitous, constitutively active and largely divalent-selective ion channel that, by virtue of sensing ATP levels, regulates homeostatic $Ca^{2+}$ and $Mg^{2+}$ fluxes according to the metabolic state of the cell. At rest, LTRPC7 may serve to maintain adequate cytosolic $Ca^{2+}$ levels. The LTRPC7-mediated upregulation of $Ca^{2+}$ influx induced by a decrease in ATP levels may support enhanced $Ca^{2+}$ uptake into mitochondria to increase the rate of ATP production by activating the $Ca^{2+}$ sensitive metabolic reaction in the mitochondrial matrix. Under severe metabolic stress, e.g., during long-lasting hypoxia or hypoglycemia, excessive LTRPC7-mediated $Ca^{2+}$ entry may contribute to the events that ultimately lead to apoptotic or necrotic cell death.

LTRPC7 can be derived from natural sources or recombinantly modified to make LTRPC7 variants. The term "LTRPC7 sequence" specifically encompasses naturally-occurring truncated or secreted forms (e.g. an extracellular domain sequence), naturally-occurring variant forms (e.g., alternatively spliced forms) and naturally-occurring allelic variants. The native sequence of the LTRPC7 polypeptide from human spleen cells is a full-length or mature native sequence LTRPC7 polypeptide comprising amino acids from 1 through about 1865 of SEQ ID NO:1 (FIG. 12). The native sequence of the LTRPC7 polypeptide from mouse monocyte cells is a full-length or mature native sequence LTRPC7 polypeptide comprising amino acids of from 1 through about 1863 of SEQ ID NO:4 (FIG. 15).

The LTRPC7 polypeptide disclosed herein as SEQ ID NO:1 (FIG. 12) comprises an N-terminal intracellular domain comprising amino acid sequences 1-757; a transmembrane domain comprising sequences 757-1070; a coiled-coil domain comprising sequences 1143-1300; a kinase domain comprising sequences 1641-1822; and three extracellular domains comprising sequences 757-855; 942-956; and 1018-1070.

The LTRPC7 polypeptide disclosed herein as SEQ ID NO:4 (FIG. 15) comprises an N-terminal intracellular domain comprising amino acid sequences 1-691; a transmembrane domain comprising sequences 757-1095; a coiled-coil domain comprising sequences 1142-1300; a kinase domain comprising sequences 1641-1822; and three extracellular domains comprising sequences 774-854; 942-955; and 1018-1070.

The LTRPC7 polypeptide of the invention, or a fragment thereof, also includes polypeptides having at least about 80% amino acid sequence identity, more preferably at least about 85% amino acid sequence identity, even more preferably at least about 90% amino acid sequence identity, and most preferably at least about 95% sequence identity with the amino acid sequences of SEQ ID NO:1 or of SEQ ID NO:4. Such LTRPC7 polypeptides include, for instance, LTRPC7 polypeptides wherein one or more amino acid residues are substituted and/or deleted, at the N- or C-terminus, as well as within one or more internal domains, of the sequences of SEQ ID NO:1 or of SEQ ID NO:4. Those skilled in the art will appreciate that amino acid changes may alter post-translational processes of the LTRPC7 polypeptide variant, such as changing the number or position of glycosylation sites or altering the membrane anchoring characteristics. All LTRPC7 proteins, however, exhibit one or more of the novel properties of the LTRPC7 polypeptides as defined herein.

"Percent (%) amino acid sequence identity" with respect to the LTRPC7 polypeptide sequences identified herein is defined as the percentage of amino acid residues in a candidate sequence that are identical with the amino acid residues of SEQ ID NO:1 (FIG. 12) or of SEQ ID NO:4 (FIG. 15), after aligning the sequences and introducing gaps, if necessary, to achieve the maximum percent sequence identity, and not considering any conservative substitutions as part of the sequence identity. The % identity values used herein are generated by WU-BLAST-2 which was obtained from Altschul et al., Methods in Enzymology, 266:460-480 (1996); http://blast.wustl/edu/blast/README.html. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a further embodiment, the % identity values used herein are generated using a PILEUP algorithm. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

In yet another embodiment, LTRPC7 polypeptides from humans, mice or from other organisms may be identified and isolated using oligonucleotide probes or degenerate polymerase chain reaction (PCR) primer sequences with an appropriate genomic or cDNA library. As will be appreciated by those in the art, particularly useful probe and/or PCR primer sequences include the unique areas of the human LTRPC7 nucleic acid sequence and/or mouse LTRPC7 nucleic acid sequence comprising SEQ ID NO:2, SEQ ID NO:3, SEQ ID NO:5, or SEQ ID NO:6, which encode all or part of the human and/or mouse N-terminal intracellular domain, transmembrane domain, and/or coiled-coil domain of SEQ ID NO:1 and/or SEQ ID NO:4. As is generally known in the art, preferred PCR primers are from about 15 to about 35 nucleotides in length, with from about 20 to about 30 being preferred, and may contain inosine as needed. The conditions for the PCR reaction are well known in the art.

In a preferred embodiment, LTRPC7 is a "recombinant protein" which is made using recombinant techniques, i.e. through the expression of a recombinant LTRPC7 nucleic acid. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or of amino acid substitutions, additions and deletions, as discussed below.

In a further embodiment, LTRPC7 variants may be recombinantly engineered by replacing one amino acid with another amino acid having similar structural and/or chemical properties, such as the replacement of a leucine with a serine, i.e., conservative amino acid replacements.

In a further embodiment substitutions, deletions, additions or any combination thereof may be used to make LTRPC7 variants. Generally these changes are done on a few amino acids to minimize the alteration of the molecule. However, larger changes may be tolerated in certain circumstances. When small alterations in the characteristics of the LTRPC7 polypeptide are desired, substitutions are generally made in accordance with the following:

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

In a further embodiment, substantial changes in function or in immunological identity are made by selecting substitutions that are less conservative than those shown in Chart 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g., phenylalanine, is substituted for (or by) one not having a side chain, e.g., glycine. The LTRPC7 variants of this embodiment exhibit one or more properties of the LTRPC7 polypeptides originally defined herein.

In a further embodiment, the variants typically exhibit the same qualitative biological activity and will elicit the same immune response as the naturally-occurring analogue, although variants also are selected to modify the characteristics of the LTRPC7 polypeptides as needed. Alternatively, the variant may be designed such that the biological activity of the LTRPC7 polypeptides is altered. For example, glycosylation sites may be altered or removed. The proteins encoded by the nucleic acid variants exhibit at least one of the novel LTRPC7 polypeptide properties defined herein.

The proteins encoded by nucleic acid variants exhibit at least one of the novel LTRPC7 polypeptide properties defined herein.

As used herein, "LTRPC7 nucleic acids" or their grammatical equivalents, refer to nucleic acids, that encode LTRPC7 polypeptides exhibiting one or more of the novel LTRPC7 polypeptide properties previously described. The LTRPC7 nucleic acids exhibit sequence homology to SEQ ID NO:2 (FIG. 13) or SEQ ID NO:3 (FIG. 14), and/or to SEQ ID NO:5 (FIG. 16) or SEQ ID NO:6 (FIG. 17), where homology is determined by comparing sequences or by hybridization assays.

Figure 5A:
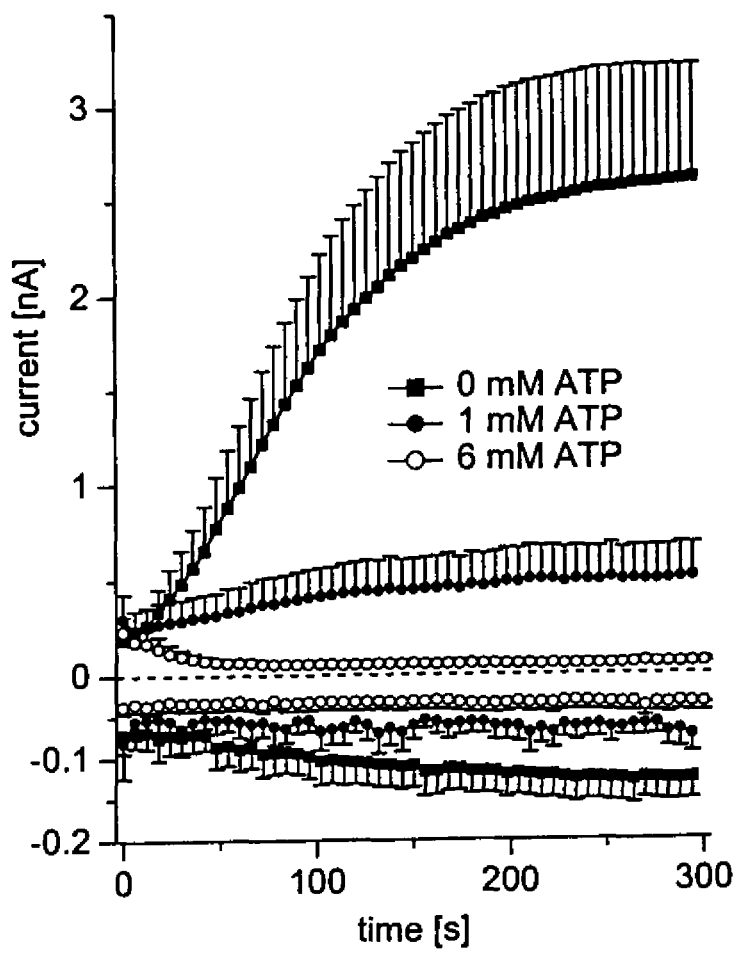
FIG. 5(A) shows the average inward and outward currents carried by recombinant LTRPC7 at −80 and +80 mV, respectively (n=5). Cells were perfused intracellularly with internal solutions containing various ATP concentrations (0 mM ATP n=7±sem; 1 mM ATP n=5±sem; 6 mM ATP n=5±sem).
Figure 5B:
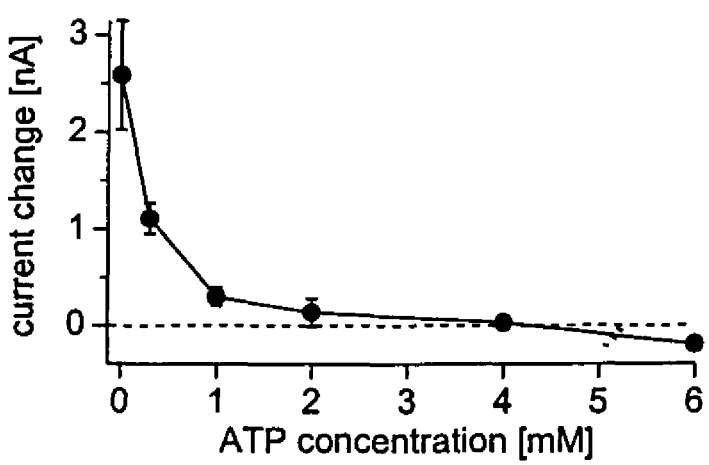
Figure 6:
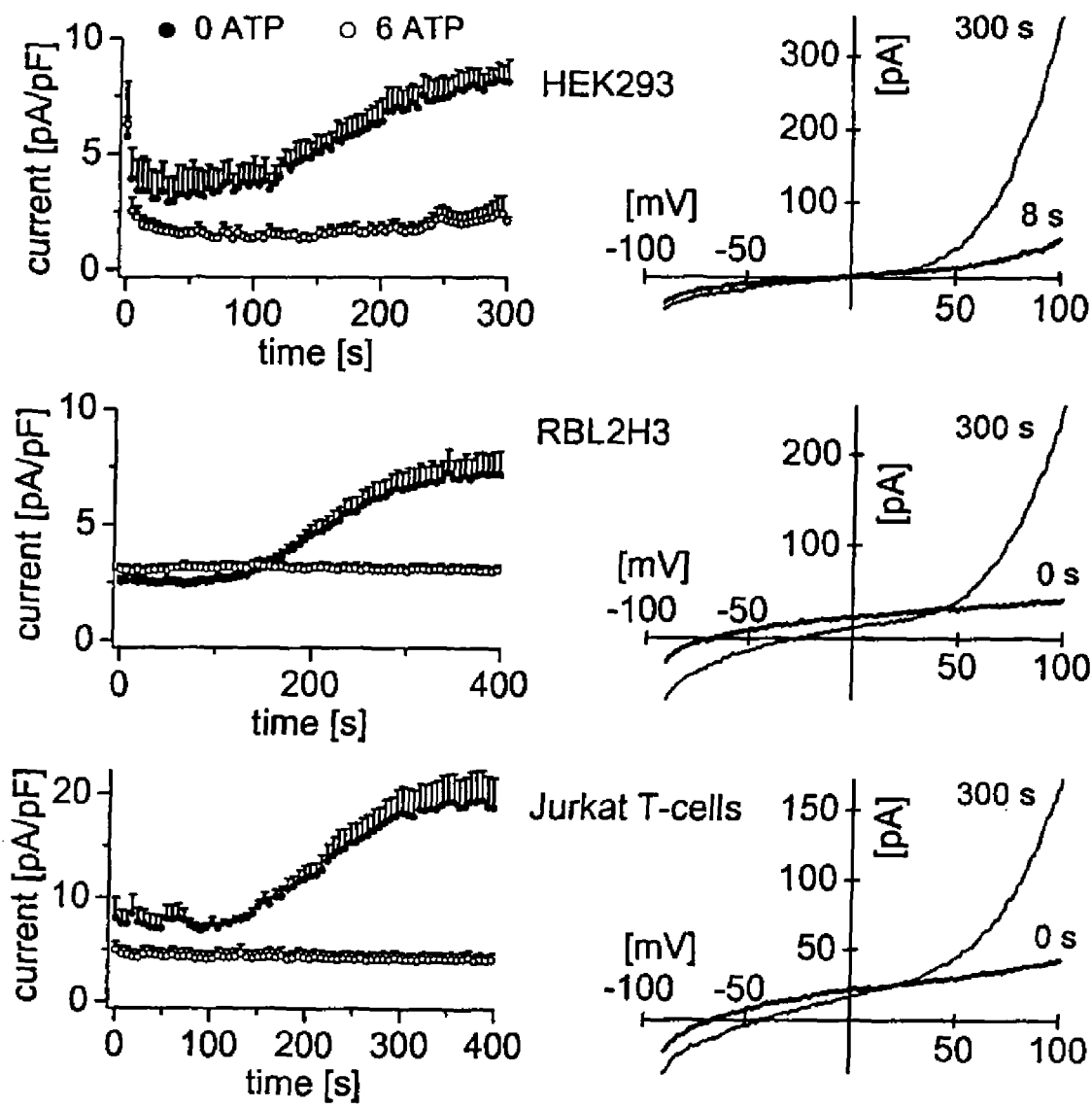
FIG. 6 demonstrates that ATP depletion-activated conductances are ubiquitous. Various cell lines were analyzed for the presence of ATP-dependent currents. Wild type HEK-293, RBL-2H3, and Jurkat T-lymphocytes were perfused with standard internal solutions supplemented with either 6 mM ATP (E; n=5±sem) or no ATP (J; n=5±sem). In the absence of ATP, all three cell types developed a small outwardly rectifying cationic conductance, which was absent when ATP was included in the pipette solution. Current amplitudes were normalized for capacitance to assess and compare current densities. The activation time course (left panels) and I/V signature of the currents (right panels) were very similar to the recombinant LTRPC7 conductance. Except for wild type HEK-293 cells, the superimposed high-resolution records in the right panels were acquired immediately after whole-cell establishment (0 s) and after 300 s. Since HEK-293 cells possess voltage-dependent $K^+$ currents that under our experimental conditions require a few seconds to inactivate, we chose a current record acquired 8 s into the experiment to represent basal current levels.
Figure 7A:
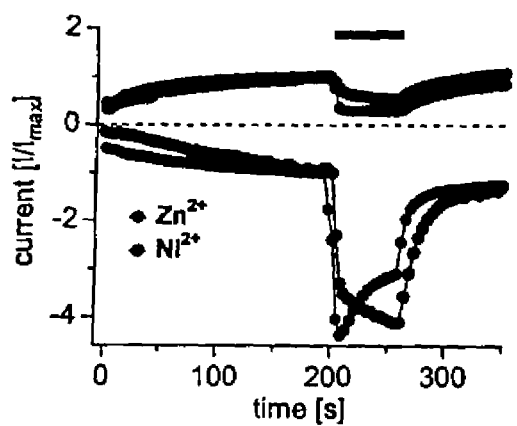
FIG. 7(A) demonstrates that exposure to 10 mM $Zn^{2+}$ (n=5) and 10 mM $Ni^{2+}$ (n=9) caused a large increase of the inward current, with a block of the outward current.
Figure 7B:
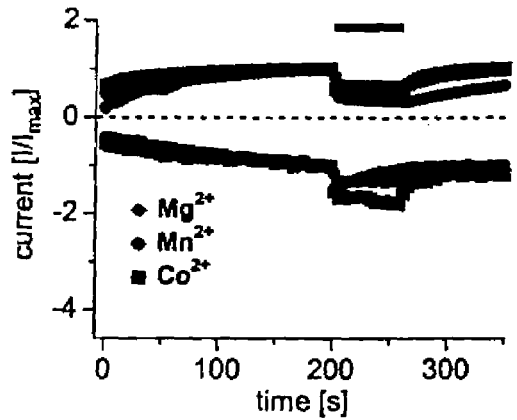
FIG. 7(B) shows that 10 mM $Co^{2+}$ (n=3), 10 mM $Mg^{2+}$ (n=5) and 10 mM $Mn^{2+}$ (n=5) caused a slight to moderate increase of the inward current, with a block of the outward current.
Figure 7C:
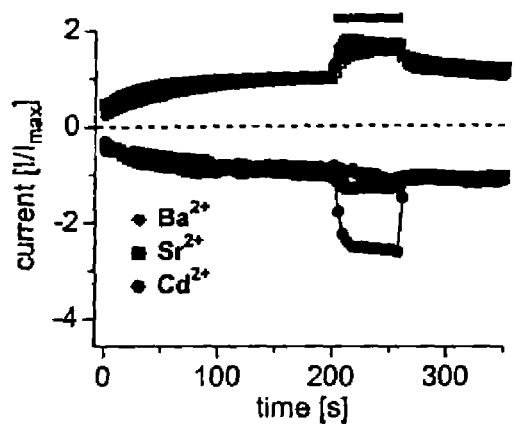
Figure 7D:
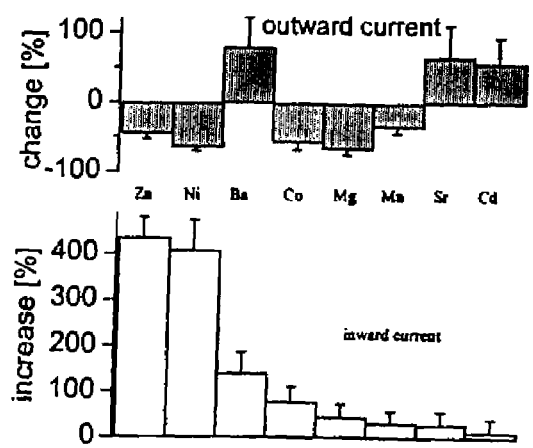
In FIG. 7(D), the lower panel shows the rank order of permeation through LTRPC7 based on percentage increase (±S.E.M.) of the inward current when carrying the test cation relative to the current magnitude at 10 mM $Ca^{2+}$. The top panel plots effects on the outward current as percent increase or inhibition (±S.E.M.) for each divalent cation.
Figure 8A:
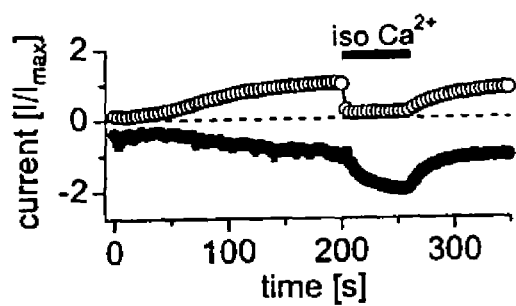
FIG. 8(A) demonstrates that exposure to isotonic $Ca^{2+}$ (n=4) induces increase of the inward and block of the outward current.
Figure 8B:
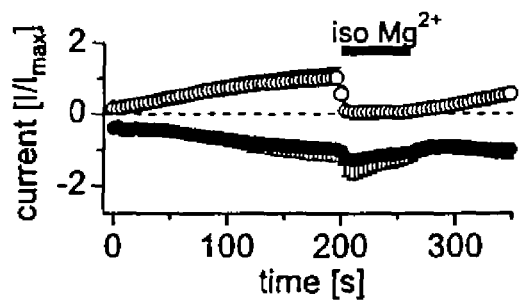
FIG. 8(B) demonstrates that isotonic $Mg^{2+}$ (n=5) induces a similar increase of the inward and block of the outward current, but recovery is delayed.
Figure 8C:
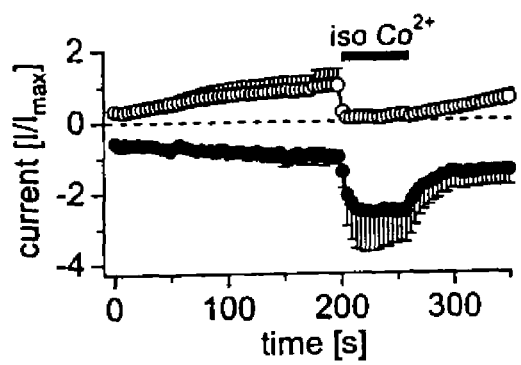
FIGS. 8(C) and 8(D) demonstrate that isotonic Co 2+(n=3) and isotonic Mn 2+(n=3) induce gradual increase of the inward current with strong block of the outward current.
Figure 8D:
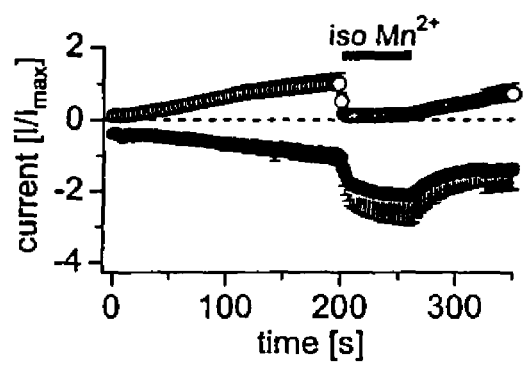

An LTRPC7 nucleic acid encoding an LTRPC7 polypeptide is homologous to the cDNA set forth in FIG. 13 (SEQ ID NO:2) and/or to the genomic DNA set forth in FIG. 14 (SEQ ID NO:3) or to the cDNA set forth in FIG. 5 (SEQ ID NO:16) and/or to the genomic DNA set forth in FIG. 17 (SEQ ID NO:6). Such LTRPC7 nucleic acids are preferably greater than about 75% homologous, more preferably greater than about 80%, more preferably greater than about 85% and most preferably greater than 90% homologous. In some embodiments the homology will be as high as about 93 to 95 or 98%. Homology in this context means sequence similarity or identity, with identity being preferred. A preferred comparison for homology purposes is to compare the sequence containing sequencing differences to the known LTRPC7 sequence. This homology will be determined using standard techniques known in the art, including, but not limited to, the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *PNAS USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387-395 (1984), preferably using the default settings, or by inspection.

In a preferred embodiment, the % identity values used herein are generated using a PILEUP algorithm. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351-360 (1987); the method is similar to that described by Higgins & Sharp *CABIOS* 5:151-153 (1989). Useful PILEUP parameters including a default gap weight of 3.00, a default gap length weight of 0.10, and weighted end gaps.

In preferred embodiment, a BLAST algorithm is used. BLAST is described in Altschul et al., *J. Mol. Biol.* 215:403-410, (1990) and Karlin et al., *PNAS USA* 90:5873-5787 (1993). A particularly useful BLAST program is the WU- BLAST-2, obtained from Altschul et al., *Methods in Enzymology*, 266:460-480 (1996); http://blast.wustl/edu/blast/README.html. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a preferred embodiment, "percent (%) nucleic acid sequence identity" is defined as the percentage of nucleotide residues in a candidate sequence that are identical with the nucleotide residue sequences of SEQ ID NO:2 (FIG. 13), SEQ ID NO:3 (FIG. 14), SEQ ID NO:5 (FIG. 16) and/or of SEQ ID NO:6 (FIG. 17). A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of SEQ ID NO:2 (FIG. 13), SEQ ID NO:3 (FIG. 14), SEQ ID NO:5 (FIG. 16) and/or SEQ ID NO:6 (FIG. 17), it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

As described above, the LTRPC7 nucleic acids can also be defined by homology as determined through hybridization studies. Hybridization is measured under low stringency conditions, more preferably under moderate stringency conditions, and most preferably, under high stringency conditions. The proteins encoded by such homologous nucleic acids exhibit at least one of the novel LTRPC7 polypeptide properties defined herein. Thus, for example, nucleic acids which hybridize under high stringency to a nucleic acid having the sequence set forth as SEQ ID NO:2 (FIG. 13), SEQ ID NO:3 (FIG. 14), SEQ ID NO:5 (FIG. 16) or SEQ ID NO:6 (FIG. 17) and their complements, are considered LTRPC7 nucleic acid sequences providing they encode a protein having an LTRPC7 property.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional examples of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL, denatured sheared salmon sperm DNA, followed by washing the filters in 1×SSC at about 37-50° C. The skilled artisan will recognize how to adjust the temperature, ionic strength, etc. as necessary to accommodate factors such as probe length and the like. Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

In another embodiment, less stringent hybridization conditions are used; for example, moderate or low stringency conditions may be used, as are known in the art. For additional details regarding stringency of hybridization reactions, see Ausubel et al., *Current Protocols in Molecular Biology*, Wiley Interscience Publishers, (1995).

The LTRPC7 nucleic acids, as defined herein, may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also include the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The LTRPC7 nucleic acids, as defined herein, are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Homologs and alleles of the LTRPC7 nucleic acid molecules are included in the definition. Genetically modified LTRPC7 nucleic acid molecules are further included in this definition.

The full-length native sequence (human) LTRPC7 gene (SEQ ID NO:3) and/or the full-length native sequence (mouse) LTRPC7 gene (SEQ ID NO:6), or portions thereof, may be used as hybridization probes for a cDNA library to isolate the full-length LTRPC7 gene from other multicellular eukaryotic species, or to isolate still other genes (for instance, those encoding naturally-occurring variants of the LTRPC7 polypeptide or the LTRPC7 polypeptide from other multicellular eukaryotic species) which have a desired sequence identity to a particular LTRPC7 nucleotide coding sequence. Optionally, the length of the probes will be about 20 through about 50 bases. The hybridization probes may be derived from the nucleotide sequences of SEQ ID NO:2, the nucleotide sequences of SEQ ID NO:3, the nucleotide sequences of SEQ ID NO:5, the nucleotide sequences of SEQ ID NO:6, or from genomic sequences including promoters, enhancer elements and introns of particular native nucleotide sequences of LTRPC7. By way of example, a screening method will comprise isolating the coding region of an LTRPC7 gene using the known DNA sequence to synthesize a selected probe of about 40 bases.

Hybridization probes may be labeled by a variety of labels, including radionucleotides such as $^{32}$P or $^{35}$S, or enzymatic labels such as alkaline phosphatase coupled to the probe via avidin/biotin coupling systems. Labeled probes having a sequence complementary to that of the LTRPC7 gene of the invention can be used to screen libraries of human cDNA, genomic DNA or mRNA to determine which members of such libraries the probe hybridizes to. Hybridization have been previously described below.

The probes may also be employed in PCR techniques to generate a pool of sequences for identification of closely related LTRPC7 nucleotide coding sequences. Nucleotide sequences encoding LTRPC7 polypeptides can also be used to construct hybridization probes for mapping the gene which encodes that LTRPC7 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries In another embodiment, DNA encoding the LTRPC7 polypeptide may be obtained from a cDNA library prepared from tissue believed to possess the LTRPC7 mRNA and to express it at a detectable level. Accordingly, human LTRPC7 DNA can be conveniently obtained from a cDNA library prepared from human tissue, or a cDNA spleen library prepared from human spleen tissue. The LTRPC7-encoding gene may also be obtained from a multicellular eukaryotic genomic library or by oligonucleotide synthesis.

Libraries can be screened with probes (such as antibodies to LTRPC7 DNA or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding LTRPC7 is to use PCR methodology [Sambrook et al., supra; Dieffenbach et al., *PCR Primer: A Laboratory Manual* (Cold Spring Harbor Laboratory Press, 1995)].

The examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra, and have been described previously.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, BLAST, BLAST2 and INHERIT which employ various algorithms to measure homology, as has been previously described.

Nucleic acid encoding LTRPC7 polypeptides, as defined herein, may be obtained by screening selected cDNA or genomic libraries using all or part of the nucleotide sequences of SEQ ID NO:2 (FIG. 13), SEQ ID NO:3 (FIG. 14), SEQ ID NO:5 (FIG. 16), or SEQ ID NO:6 (FIG. 17). Conventional primer extension procedures as described in Sambrook et al., supra, are used to detect precursors and processing intermediates of mRNA that may not have been reverse-transcribed into cDNA.

Nucleotide sequences (or their complement) encoding the LTRPC7 polypeptides have various applications in the art of molecular biology, including uses as hybridization probes, in chromosome and gene mapping, and in the generation of anti-sense RNA and DNA.

In another embodiment, the LTRPC7 nucleic acids, as defined herein, are useful in a variety of applications, including diagnostic applications, which will detect naturally occurring LTRPC7 nucleic acids, as well as screening applications; for example, biochips comprising nucleic acid probes to the LTRPC7 nucleic acids sequences can be generated. In the broadest sense, then, by "nucleic acid" or "oligonucleotide" or grammatical equivalents herein means at least two nucleotides covalently linked together.

In another embodiment, the LTRPC7 nucleic acid sequence of SEQ ID NO:2 (FIG. 13) or SEQ ID NO:5 (FIG. 16), as described above, is a fragment of a larger gene, i.e. it is a nucleic acid segment. "Genes" in this context include coding regions, non-coding regions, and mixtures of coding and non-coding regions. Accordingly, as will be appreciated by those in the art, using the sequences provided herein, additional sequences of LTRPC7 genes can be obtained, using techniques well known in the art for cloning either longer sequences or the full length sequences; see Maniatis et al., and Ausubel, et al., supra, hereby expressly incorporated by reference.

Once the LTRPC7 nucleic acid, as described above, is identified, it can be cloned and, if necessary, its constituent parts recombined to form the entire LTRPC7 gene. Once isolated from its natural source, e.g., contained within a plasmid or other vector or excised therefrom as a linear nucleic acid segment, the recombinant LTRPC7 nucleic acid can be further-used as a probe to identify and isolate other LTRPC7 nucleic acids, from other multicellular eukaryotic organisms, for example additional coding regions. It can also be used as a "precursor" nucleic acid to make modified or variant LTRPC7 nucleic acids.

In another embodiment, the LTRPC7 nucleic acid (e.g., cDNA or genomic DNA), as described above, encoding the LTRPC7 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

A host cell comprising such a vector is also provided. By way of example, the host cells may be mammalian host cell lines which include Chinese hamster ovary (CHO), COS cells, and HEK cells. More specific examples of host cells include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art. In the preferred embodiment, HEK-293 cells are used as host cells. A process for producing LTRPC7 polypeptides is further provided and comprises culturing host cells under conditions suitable for expression of the LTRPC7 polypeptide and recovering the LTRPC7 polypeptide from the cell culture.

In another embodiment, expression and cloning vectors are used which usually contain a promoter, either constitutive or inducible, that is operably linked to the LTRPC7-encoding nucleic acid sequence to direct mRNA synthesis. Promoters recognized by a variety of potential host cells are well known. The transcription of an LTRPC7 DNA encoding vector in mammalian host cells is preferably controlled by an inducible promoter, for example, by promoters obtained from heterologous mammalian promoters, e.g. the actin promoter or an immunoglobulin promoter, and from heat-shock promoters. Examples of inducible promoters which can be practiced in the invention include the hsp 70 promoter, used in either single or binary systems and induced by heat shock; the metallothionein promoter, induced by either copper or cadmium (Bonneton et al. 1996, *FEBS Lett.* 380(1-2): 33-38); the *Drosophila* opsin promoter, induced by *Drosophila* retinoids (Picking, et al., 1997, *Experimental Eye Research.* 65(5): 717-27); and the tetracycline-inducible full CMV promoter. Of all the promoters identified, the tetracycline-inducible full CMV promoter is the most preferred. Examples of constitutive promoters include the GAL4 enhancer trap lines in which expression is controlled by specific promoters and enhancers or by local position effects (http:/www.fruitfly.org; http://www.astorg.u-strasbg.fr:7081); and the transactivator-responsive promoter, derived from *E. coli*, which may be either constitutive or induced, depending on the type of promoter it is operably linked to.

Transcription of a DNA encoding the LTRPC7 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the LTRPC7 coding sequence, but is preferably located at a site 5' from the promoter.

The methods of the invention utilize LTRPC7 polypeptides or nucleic acids which encode LTRPC7 polypeptides for identifying candidate bioactive agents which bind to LTRPC7, which modulate the activity of LTRPC7 ion channels, or which alter the expression of LTRPC7 within cells The term "candidate bioactive agent" as used herein describes any molecule which binds to LTRPC7, modulates the activity of an LTRPC7 ion channel, and/or alters the expression of LTRPC7 within cells. A molecule, as described herein, can be an oligopeptide, small organic molecule, polysaccharide, or polynucleotide, etc. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons (D).

Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of multicellular eucaryotic proteins may be made for screening in the methods of the invention. Particularly preferred in this embodiment are libraries of multicellular eukaryotic proteins, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

In a preferred embodiment, anti-sense RNAs and DNAs can be used as therapeutic agents for blocking the expression of certain LTRPC7 genes in vivo. It has already been shown that short antisense oligonucleotides can be imported into cells where they act as inhibitors, despite their low intracellular concentrations caused by their restricted uptake by the cell membrane. (Zamecnik et al., (1986), *Proc. Natl. Acad. Sci. USA* 83:4143-4146). The anti-sense oligonucleotides can be modified to enhance their uptake, e.g. by substituting their negatively charged phosphodiester groups by uncharged groups. In a preferred embodiment, LTRPC7 anti-sense RNAs and DNAs can be used to prevent LTRPC7 gene transcription into mRNAs, to inhibit translation of LTRPC7 mRNAs into proteins, and to block activities of preexisting LTRPC7 proteins.

As used herein, a multivalent cation indicator is a molecule that is readily permeable to a cell membrane or otherwise amenable to transport into a cell e.g., via liposomes, etc., and upon entering a cell, exhibits a fluorescence that is either enhanced or quenched upon contact with a multivalent cation. Examples of multivalent cation indicators useful in the invention are set out in Haugland, R. P. *Handbook of Fluorescent Probes and Research Chemicals*. 6th ed. Molcular Probes, Inc Eugene, Oreg., pp. 504-550 (1996);

(http://www.probes.com/handbook/sections/2000.html), incorporated herein by reference in its entirety.

In a preferred embodiment for binding assays, either LTRPC7 or the candidate bioactive agent is labeled with, for example, a fluorescent, a chemiluminescent, a chemical, or a radioactive signal, to provide a means of detecting the binding of the candidate agent to LTRPC7. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound LTRPC7. As known in the art, unbound labeled streptavidin is removed prior to analysis. Alternatively, LTRPC7 can be immobilized or covalently attached to a surface and contacted with a labeled candidate bioactive agent. Alternatively, a library of candidate bioactive agents can be immobilized or covalently attached to a biochip and contacted with a labeled LTRPC7. Procedures which employ biochips are well known in the art.

In a preferred embodiment, the ion permeability of LTRPC7 is measured in intact cells, preferably HEK-293 cells, which are transformed with a vector comprising nucleic acid encoding LTRPC7 and an inducible promoter operably linked thereto. Endogenous levels of intracellular ions are measured prior to inducement and then compared to the levels of intracellular ions measured subsequent to inducement. Fluorescent molecules such as fura-2 can be used to detect intracellular ion levels. LTRPC7 permeability to heavy metal ions such as manganese can be measured in this assay.

In a preferred embodiment, the ion permeability of any type of ion channel can be measured in intact cells, preferably HEK-293 cells, which are transformed with a vector comprising nucleic acid encoding the ion channel and an inducible promoter operably linked thereto. Endogenous levels of intracellular ions are measured prior to inducement and then compared to the levels of intracellular ions measured subsequent to inducement. Fluorescent molecules such as fura-2 can be used to detect intracellular ion levels. Ion channel permeability to heavy metal ions such as manganese can be measured in this assay. This system can also be used to identify candidate bioactive agents which modulate the ion permeability of the recombinant ion channel such as described for LTRPC7.

In a preferred embodiment for screening for candidate bioactive agents which modulate expression levels of LTRPC7 within cells, candidate agents can be used which wholly suppress the expression of LTRPC7 within cells, thereby altering the cellular phenotype. In a further preferred embodiment, candidate agents can be used which enhance the expression of LTRPC7 within cells, thereby altering the cellular phenotype. Examples of these candidate agents include antisense cDNAs and DNAs, regulatory binding proteins and/or nucleic acids, as well as any of the other candidate bioactive agents herein described which modulate transcription or translation of nucleic acids encoding LTRPC7.

In one embodiment, the invention provides antibodies which specifically bind to unique epitopes on the human LTRPC7 polypeptide, e.g. unique epitopes of the protein comprising amino acids 1 through about 1865 of SEQ ID NO:1 (FIG. 12).

In another embodiment, the invention provides antibodies which specifically bind to unique epitopes on the mouse LTRPC7 polypeptide, e.g. unique epitopes of the protein comprising amino acids 1 through about 1863 of SEQ ID NO:4 (FIG. 15).

In another embodiment, the invention provides an antibody which specifically binds to epitopes from the human LTRPC7 extracellular domain comprising nucleotides 757-855 or 942-956 or 1018-1070 of SEQ ID NO:1 (FIG. 12).

In another embodiment, the invention provides an antibody which specifically binds to epitopes from the mouse LTRPC7 extracellular domain comprising nucleotides 774-854 or 942-955 or 1018-1070 of SEQ ID NO:4 (FIG. 15).

The anti-LTRPC7 polypeptide antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the LTRPC7 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The anti-LTRPC7 polypeptide antibodies may further comprise monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the LTRPC7 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against an LTRPC polypeptide. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The anti-LTRPC7 polypeptide antibodies may further comprise monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

The anti-LTRPC7 polypeptide antibodies may further comprise humanized antibodies or human antibodies. Humanized forms of non-human (e.g., murine) antibodies are chimeric immunoglobulins, immunoglobulin chains or fragments thereof (such as Fv, Fab, Fab$^1$, F(ab$^1$)$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by the introducing of human immunoglobulin loci into transgenic animals, e.g. mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

The anti-LTRPC7 polypeptide antibodies may further comprise heteroconjugate antibodies. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a further embodiment, the anti-LTRPC7 polypeptide antibodies may have various utilities. For example, anti-LTRPC7 polypeptide antibodies may be used in diagnostic assays for LTRPC7 polypeptides, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, Monoclonal

*Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Further, LTRPC7 antibodies may be used in the methods of the invention to screen for their ability to modulate the permeability of LTRPC7 channels to multivalent cations.

EXAMPLES

Commercially available reagents referred to in the examples were used according to manufacturer's instructions unless otherwise indicated.

Example 1

Isolation of cDNAs and Sequence Analysis

Once a partial sequence for human LTRPC7 was identified out of lymphocyte EST libraries, the corresponding EST clone was purchased and sequenced (accession number AA419407 was obtained). Partial sequences from the 5' or 3' ends of AA419407 were used to screen leukocyte, spleen, and kidney libraries using the GeneTrapper II method (Life Technologies) in order to extend the original sequences towards the 5' and 3' ends of the respective mRNA's. Resulting clones were sequenced in both directions using standard fluorescent dideoxy sequencing techniques and partial contigs were assembled using Assembylign (Oxford Molecular, London, UK). For LTRPC7, the available coding sequence was assembled primarily from the sequences of four overlapping clones designated AS8, GT2, B5, and D2, with some sequence confirmation obtained from end sequences of many shorter clones. We also cloned the murine LTRPC7 transcript using a similar approach, and assembled a full sequence contig from two overlapping clones designated MA7 and MA5. The predicted murine LTRPC7 protein exhibited ~95% amino acid identity with the human version. The full murine and human LTRPC7 cDNA sequences and predicted proteins will be deposited in Genbank prior to publication. Predicted proteins and hydrophobicity analyses were obtained using the Macvector program (Oxford Biotechnology), prediction of transmembrane spanning regions was performed using the TMpred program at EMBnetENRfu[12], coiled coil analysis was performed using the ISREC coils serverENRfu[13], and BLAST alignments were obtained using the NCBI advanced BLAST server.

Example 2

Northern Blotting

Multiple tissue Northern blots for human tissues and cell lines were obtained from Clontech (Palo Alto, Calif.), and all hybridizations were performed according to the manufacturer's protocols. LTRPC7 Northern blots were performed using a dUTP labeled RNA probe generated from a 500 bp fragment corresponding to the most 5' end of the available LTRPC7 coding sequence from clone AS8. The probe was generated using a T7-directed RNA probe synthesis kit from Ambion (Austin, Tex.).

Example 3

RT-PCR Expression Analysis

RT-PCR analysis was performed from the indicated human tissue cDNA libraries according to the manufacturers protocols (Life Technologies, Gaithersburg, Md.). For LTRPC7, oligo's used were GTCACTTGGAAACTGGAACC [SEQ ID NO: 7] and CGGTAGATGGCCTTCTACTG [SEQ ID NO: 8] to produce a 278 bp band. PCR was performed using standard techniques and 30 cycles of 94 degrees for 30 seconds, 55 degrees for 30 seconds, and 72 degrees for 60 seconds. Approximate intensity of the ethidium bromide staining of correct sized bands was estimated by eye to be from 1–2+. Note that the LTRPC7 primers used in these reactions were generated from initial EST sequences, and contain a single base pair mismatch at the 5' end of the primer based on the corresponding region of LTRPC7 sequence obtained from subsequent clones.

Example 4

Eukaryotic Expression Constructs, Transfection

For the purpose of expressing LTRPC7 in eukaryotic cells, we used PCR to produce an epitope tagged expression construct from our two overlapping murine LTRPC7 clones. The LTRPC7 coding sequence was modified by removing the initiating methionine and replacing it with a sequence encoding a Kozak sequence, the FLAG tag and the additional sequence GCGGCCGCAT_[SEQ ID NO:9], and by placing a SpeI site just after the stop codon. These modifications result in an expressed protein which started with the following amino acid sequence: MGDYKDDDDKRPH [SEQ ID NO:10] followed by the murine LTRPC7 coding sequence starting at the second amino acid. This construct was expressed from the pAPuro vector which allows constitutive LTRPC7 expression from a beta-actin promotor, and from the pcDNA4/TO vector which provides tetracycline-controlled expression from a CMV promotor. The FLAG-LTRPC7/pAPuro vector was used to attempt to express LTRPC7 in several cell lines; however only very low expression was observed in transient expression experiments and no expression was ever observed in stable clones. The FLAG-LTRPC7/pCDNA4/TO construct was transfected by electroporation into HEK-293 cells expressing the tet repressor protein, and clones were selected in zeocin. Several resistant clones were selected for analysis of tetracycline-induced FLAG-LTRPC7 expression. As might be expected from our inability to express LTRPC7 using pApuro-mediated constitutive expression, all clones had low/undetectable basal expression and all clones found to express the FLAG-LTRPC7 protein subsequently exhibited growth arrest and significant toxic effects after several days of tetracycline/doxycycline induction. The clone with the highest inducible expression was chosen for subsequent electrophysiological analyses.

Example 5

Immunoprecipitations and SDS/PAGE-Western Blotting

Anti-FLAG immunoprecipitations were performed from lysates of $10^7$ HEK-293 cells. Immunoprecipitated proteins were washed three times with lysis buffer, separated by SDS/PAGE using 6% polyacrylamide gels, transferred to a PVDF membrane, and analyzed by anti-FLAG immunoblotting. All procedures used standard methods as previously describedENRfu[14].

Example 6

Generation of DT-40 Cells in which LTRPC7 is Inducibly Deficient

Chicken LTRPC7 genomic fragments were obtained by screening λFIXII chicken genomic library using a 0.5-kb mouse LTRPC7 cDNA fragment including putative transmembrane region as a probe under a low stringent condition. The conventional targeting vectors (pLTRPC7-hisD and pLTRPC7-bsr, which allow inactivation of LTRPC7) were constructed by replacing the genomic fragment-containing exons that correspond to a part of putative transmembrane region with hisD or bsr cassette. These cassettes were flanked by 3.5 and 5.7 kb of chicken LTRPC7 genomic sequence on the 5' and 3' sides, respectively. To generate the inducible targeting vector, pLTRPC7-neo/loxP, the putative transmembrane region of LTRPC7 was inserted between two loxP sites for the vector pKSTKNEOLOXP, which has HSV thymidine kinase and loxP flanked pGK-neo. Then, the 3.5-kb fragment 5' upstream and the 2.6-kb fragment 3' downstream of the loxP flanked region were inserted.

As briefly described in the main text, in our initial attempt to generate DT-40 cells genetically deficient in the ltrpc7 gene, the targeting constructs, pLTRPC7-bsr and pLTRPC7-hisD, were sequentially introduced into DT-40 cells. Although the first allele targeting by using pLTRPC7-bsr resulted in success with high frequency (71%), clones harboring two targeted alleles were not obtained after several rounds of transfection with pLTRPC7-hisD. Since transfection with pLTRPC7-hisD also worked for the first allele targeting, these results suggested that inactivation of the ltrpc7 gene might lead to lethality in DT-40 cells.

Based on these results, the Cre-loxP system was utilized for disruption of the ltrpc7 gene. The expression plasmid pANMerCreMer-hyg encoding tamoxifen-regulated chimeric Cre enzymeENRfu[15] was linearized and introduced into wild-type DT-40. Transfectants were selected in the presence of hygromycine B (2 mg/ml) and resistant clones were screened for inducible-Cre expression by Western blotting analysis. Then, pLTRPC7-neo/loxP was transfected into the clone expressing inducible-Cre, and was selected with both hygromycine B (2 mg/ml) and G418 (2 µg/ml). After confirming successful targeting by Southern blot analysis, cells were cultured in the presence of 200 nM tamoxifen to examine the potentiality of Cre-mediated recombination. Then, pTRPC7-hisD was transfected into the capable clones, and was selected with hygromycine B (2 mg/ml), G418 (2 mg/ml) and histidinol (0.5 mg/ml).

Example 7

Electrophysiology

For patch-clamp experiments, cells grown on glass coverslips were transferred to the recording chamber and kept in a standard modified Ringer's solution of the following composition (in mM): NaCl 145, KCl 2.8, CsCl 10, $CaCl_2$ 1, $MgCl_2$ 2, glucose 10, Hepes.NaOH 10, pH 7.2. In some experiments, nominally $Ca^{2+}$ and/or $Mg^{2+}$-free extracellular solutions or isotonic $Ca^{2+}$ solutions (120 mM $CaCl_2$) were applied by pressure ejection from wide-tipped pipettes. Intracellular pipette-filling solutions contained (in mM): Cs-glutamate 145, NaCl 8, $MgCl_2$ 1, Cs-BAPTA 10, pH 7.2 adjusted with CsOH. In some experiments, Cs-glutamate was replaced equimolarly by K-glutamate or N-methyl-D-glucamine-chloride. Patch-clamp experiments were performed in the tight-seal whole-cell configuration at 21-25° C. High-resolution current recordings were acquired by a computer-based patch-clamp amplifier system (EPC-9, HEKA, Lambrecht, Germany). Sylgard-coated patch pipettes had resistances between 2-4 M after filling with the standard intracellular solution. Immediately following establishment of the whole-cell configuration, voltage ramps of 50 ms duration spanning the voltage range of −100 to +100 mV were delivered from a holding potential of 0 mV at a rate of 0.5 Hz over a period of 200 to 400 seconds. All voltages were corrected for a liquid junction potential of 10 mV between external and internal solutions when internal solutions contained glutamate. Currents were filtered at 2.3 kHz and digitized at 100 µs intervals. Capacitive currents and series resistance were determined and corrected before each voltage ramp using the automatic capacitance compensation of the EPC-9. The low-resolution temporal development of currents at a given potential was extracted from individual ramp current records by measuring the current amplitudes at voltages of −80 mV or +80 mV.

Example 8

Equimolar Substitution of 10 mM $Ca^{2+}$ by other Divalent Metal Ions

LTRPC7 represents an ion channel that is selective for divalent cations at negative membrane potentials and its activity is regulated by intracellular levels of Mg.nucleotides (Nadler et al., 2001). Although the channel readily permeates monovalent ions upon removal of all divalent ions, inward currents carried by LTRPC7 under physiological conditions are largely carried by the dominant extracellular ion species $Ca^{2+}$ and $Mg^{2+}$. Ion currents carried by LTRPC7 have therefore been designated MagNuM (for Magnesium.Nucleotide-regulated Metal ion currents). In order to assess the permeation properties of LTRPC7 for other divalent ions, we measured ionic currents in substitution experiments, where 10 mM $Ca^{2+}$ was replaced with 10 mM of other divalent cations (FIG. 7). In these experiments, HEK-293 cells expressing LTRPC7 were kept in a bath solution containing 10 mM $Ca^{2+}$, without $Mg^{2+}$, and development of MagNuM was monitored by whole-cell patch-clamp as described previously (Nadler et al., 2001). When the current had reached maximal amplitude, cells were transiently exposed to an extracellular solution containing 10 mM of the test cation applied via a puffer pipette for a period of 60 s.

As illustrated in FIG. 7, the equimolar substitution experiments of 10 mM divalent transition metal ions resulted in characteristic changes of LTRPC7-mediated inward and outward currents. To better compare the responses and compensate for variations in expression levels, we normalized both outward and inward currents such that the current magnitudes just before substituting $Ca^{2+}$ were set to 1 and the changes in inward current are therefore relative to the current magnitude of 10 mM $Ca^{2+}$. In general, all tested divalent metal ions were at least as efficient and some even considerably more so than $Ca^{2+}$ in permeating LTRPC7 at negative membrane potentials. When considering both inward and outward current behavior, one can broadly classify the effects of divalent metal ions into three groups: The first group, $Zn^{2+}$ and $Ni^{2+}$, caused a large increase of the inward current, combined with a block of outward currents (FIG. 7A). For both $Zn^{2+}$ and $Ni^{2+}$, the increase in inward current was greater than threefold compared to $Ca^{2+}$ (FIG. 7D), whereas the inhibition of outward currents was less pronounced for $Zn^{2+}$ than for $Ni^{2+}$. We also observed significant $Ba^{2+}$ inward currents (FIGS. C and 7D), which would have placed this ion in the first group, but since $Ba^{2+}$ did not suppress outward currents, we instead chose to place this ion into the third group, which holds other divalents that are similarly ineffective in suppressing outward currents. The second group, $Co^{2+}$, $Mg^{2+}$, and $Mn^{2+}$, is characterized by more modest (less than double) increases of inward currents, but again accompanied by a block of outward currents (FIGS. 7B and 7D). The strongest block of outward currents was caused by $Mg^{2+}$, which we attribute in part to increases in $[Mg^{2+}]i$ which we have previously shown is a strong independent suppressor of MagNuM currents (Nadler et al., 2001). This effect may also underlie the progressive decay of $Mg^{2+}$ inward current observed after the initial increase. In contrast to the first two groups, the third group, $Ba^{2+}$, $Sr^{2+}$, and $Cd^{2+}$, is distinguished by increases of the outward current accompanying slight to moderate increases of the inward current (FIGS. 7C and 7D). From this we can conclude that the current changes observed above are most consistent with LTRPC7 being as or more permeable to each of the divalent cations tested above than either $Ca^{2+}$ or $Mg^{2+}$.

Interpretation of the inward current changes cannot be unequivocal, as the above experiments cannot rule out possible ion-ion interactions that would allow the co-transport of e.g. $Na^+$ ions along with divalent ions. The outward currents at positive potentials represent currents of monovalent ions at potentials where divalent ions do not experience sufficient driving force to enter the cell and therefore no longer impede monovalent outward fluxes (Hille, 1992). Their behavior is a complex function of several factors including (1) The Nernst equilibrium potential of divalent ions, which determines the degree of permeation block imposed by divalent ions at positive membrane potentials, and (2) effects of the relevant divalent ion at the intracellular side of the channel after it has gained access to the cytosol. The latter effects are particularly relevant for $Mg^{2+}$, which plays an important role as a cofactor in the gating of LTRPC7 and therefore can inactivate MagNuM if allowed to accumulate intracellularly. A similar inhibition is also seen with $Ca^{2+}$, which is the second major physiological divalent cation to permeate LTRPC7, although under our experimental conditions, the inhibitory action of $[Ca^{2+}]i$ maybe more limited due to the inclusion of 10 mM BAPTA. Since neither $Mg^{2+}$ nor the other divalent ions are significantly buffered by this chelator, we assume that cytosolic levels of these divalents can increase significantly and thereby induce the block of monovalent ions in the outward direction. Thus, the efficacy of any divalent ion to block outward currents would be the net result of the degree of permeation and its regulatory effects at the inner mouth of the channel pore. Despite the complexities involved in interpreting the behavior of outward currents, we can conclude that the current changes observed above are most consistent with LTRPC7 being as or more permeable to each of the divalent cations tested above than either $Ca^{2+}$ or $Mg^{2+}$.

Example 9

Permeation of Essential Divalent Trace Metal Ions in Isotonic Solutions

The use of isotonic solutions to probe divalent cation entry through LTRPC7 avoids complications in permeation properties arising from ion-ion interactions, and therefore allows unequivocal interpretation of inward currents—maintained or increased inward currents can only be consistent with permeation of the available extracellular cation. Isotonic solutions of 120 mM of each divalent ion yielded appropriate osmolarities within 10 mOsm from the standard bath and pipette solutions. In this series of experiments, the cells were bathed in the standard external solution containing 1 mM $Ca^{2+}$ and 2 mM $Mg^{2+}$. At 200 s, when MagNuM had reached its full amplitude, isotonic solutions of each transition metal were applied for 60 s via a puffer pipette.

The development of inward and outward currents before, during and after application of selected isotonic divalent cation solutions are shown in FIG. 8. These experiments illustrate that isotonic solutions of divalent ions considered as essential trace metals for cellular physiology in general induced an increase in inward currents through LTRPC7, while at the same time there was strong suppression of outward currents. In almost all cases, inward currents return to pre-isotonic levels after exposure to isotonic metal solutions.

Example 10

Permeation of Toxic Divalent Metal Ions in Isotonic Solutions

Figure 9A:
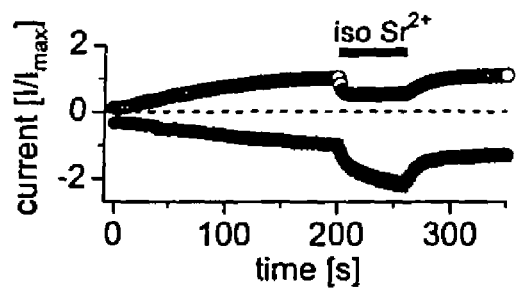
In FIGS. 9(A) and 9(B), isotonic $Ba^{2+}$ (n=3) and isotonic $Sr^{2+}$ (n=4) induce moderate increases of the inward and relatively minor inhibitions of the outward current.
Figure 9B:
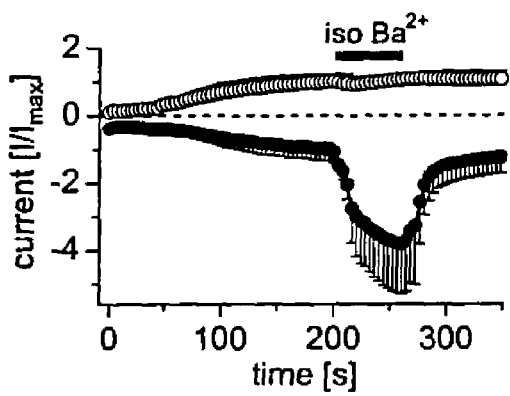
Figure 9C:
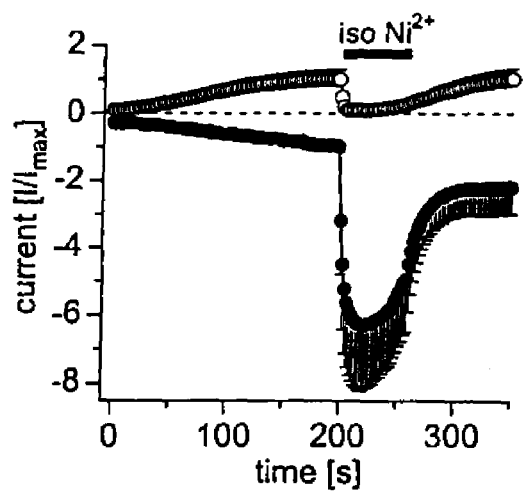
In FIG. 9(C) isotonic $Ni^{2+}$ (n=4) induces a large increase of the inward and strong block of the outward current.

In addition to physiologically relevant trace metal ions, we extended the above assays to toxic metal ions such as $Ba^{2+}$, $Sr^{2+}$ and $Ni^{2+}$ (FIG. 9). These metal ions also supported significant inward currents through LTRPC7 to different degrees. The best permeating ion species in this series was $Ni^{2+}$. The permeation sequence of all divalent ions tested in isotonic solutions is based on peak inward currents. $Ni^{2+}$ is the most permeant metal, followed by $Ba^{2+}$ and $Sr^{2+}$. These divalent ions are more effectively transported than $Ca^{2+}$ and $Mg^{2+}$. Overall, this permeation sequence is highly consistent with what was observed in the 10 mM divalent cation substitution experiments of FIG. 7.

Figure 10A:
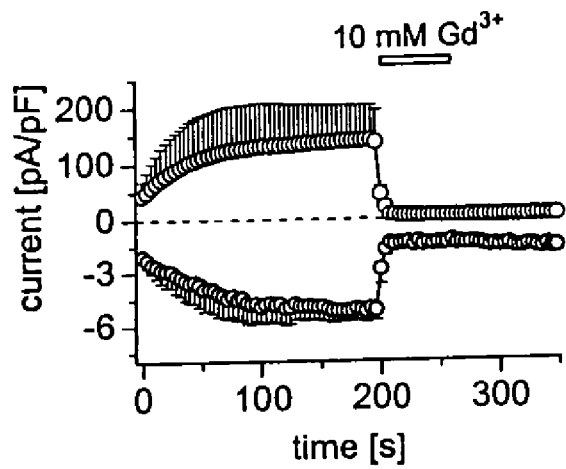
In FIGS. 10(A) and 10(B) $Gd^{3+}$ or $La^{3+}$ were applied at 10 mM (n=5 each). $Gd^{3+}$ appears to be a more potent blocker of MagNuM.
Figure 10B:
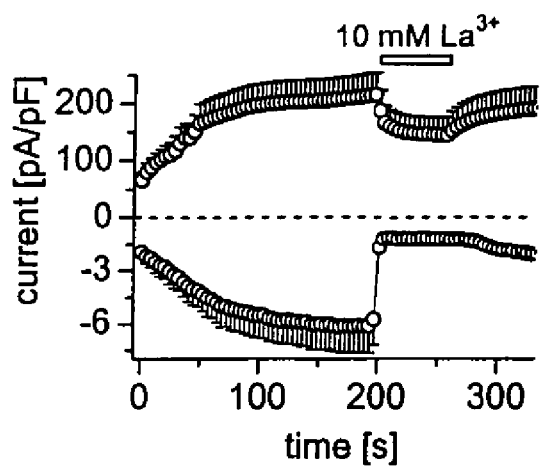

We next tested a series of toxic trivalent metal ions (FIG. 10), which we suspected to not permeate through LTRPC7. Indeed both $La^{3+}$ and $Gd^{3+}$ at 10 mM inhibited inward currents with no sign of significant permeation (FIGS. 10A and 10B). $Gd^{3+}$ appeared to be the more potent inhibitor, since outward currents were also completely suppressed. However, it remains to be determined whether this is due to some limited $Gd^{3+}$ entry causing a secondary block of outward currents from the cytosolic side. By contrast, the same concentration of $La^{3+}$, while potently and persistently inhibiting inward currents was far less effective in suppressing outward currents. We also tested concentrations of the ions that normally completely suppress voltage- or store-operated $Ca^{2+}$ channels and found that 10 µM of either $Gd^{3+}$ or $La^{3+}$ were ineffective in suppressing inward or outward currents carried by LTRPC7 (data not shown).

Example 11

$Ca^{2+}$ and $Mn^{2+}$ Entry Through LTRPC7 and Block by Mg.ATP

Based on the above permeation data, we conclude that LTRPC7 must be viewed as a potential entry pathway for a wide variety of trace and toxic metal ions. However, the above experiments were performed under conditions of complete intracellular calcium buffering, and therefore do not well reflect how LTRPC7 would function under physiological conditions. In addition, they do not include direct measurements of intracellular ion concentrations. We therefore performed two sets of experiments to address this issue. In the first, we assayed $Ca^{2+}$ permeation of LTRPC7 under conditions in which intracellular $Ca^{2+}$ is left unbuffered and LTRPC7 is activated or suppressed by manipulation of patch pipette [ATP]i. To this end, HEK-293 cells expressing LTRPC7 were kept in a bath solution with 2 mM each of $Ca^{2+}$ and $Mg^{2+}$ and were perfused with a Cs-glutamate-based internal solution containing 200 µM fura-2. Simultaneous development of MagNuM was monitored under whole-cell patch-clamp and delivering, from a holding potential of 0 mV, repetitive voltage ramps that spanned −100 to +100 mV over 50 ms at a rate of 0.5 Hz. When Mg.ATP was absent in the pipette, MagNuM rapidly activated, as witnessed by the increase in both inward and outward currents (FIG. 11A) as well as its characteristic current-voltage relationship (FIG. 11B). In parallel, fluorescence measurements revealed a steady increase of $[Ca^{2+}]i$ (FIG. 11C) that was due to $Ca^{2+}$ influx, since $[Ca^{2+}]i$ transiently increased during periodic 5-seconds hyperpolarizations to −80 mV (n=6). By contrast, in cells where the internal solution contained 3 mM Mg.ATP, there was little change in LTRPC7 activity and $[Ca^{2+}]i$ remained similarly steady under these conditions. The progressive decrease in amplitude of hyperpolarization-driven changes in $[Ca^{2+}]i$ observed under these conditions is likely due to increased $Ca^{2+}$ buffering as fura-2 equilibrates with the cytosol at its final concentration of 200 µM. Control cells not over-expressing LTRPC7 perfused with ATP-free solutions behaved very much like those perfused with 3 mM ATP (dotted trace in FIG. 7C). Thus, it appears that at physiological concentrations of extracellular $Ca^{2+}$ and $Mg^{2+}$, activation of MagNuM allows significant $Ca^{2+}$ entry in cells over-expressing LTRPC7.

In the second approach, we assayed LTRPC7 activity in intact cells using $Mn^{2+}$ quench of fura-2 fluorescence (FIG. 11D). In this experiment, HEK-293 cells over-expressing LTRPC7 were loaded with fura-2-AM and bathed in standard external solution with 1 mM $Ca^{2+}$ and 2 mM $Mg^{2+}$. $Ca^{2+}$-independent fluorescence was monitored at 360 nm (the isosbestic wavelength of fura-2) and after 120 s, an external solution containing 1 mM $Mn^{2+}$, 1 mM $Ca^{2+}$, and 0 $Mg^{2+}$ was applied for 180 s. To determine baseline quench levels, this protocol was applied to HEK-293 cells that were transfected with the same tetracycline-inducible recombinant LTRPC7 construct, but remained uninduced. As clearly shown in FIG. 11D, the application of 1 mM $Mn^{2+}$ caused a pronounced quench of the 360 nm signal in HEK-293 cells induced to express LTRPC7 (n=5), whereas $Mn^{2+}$-induced quench of the 360 nm signal in uninduced cells (n=5) was noticeable but much less dramatic. Linear regression over the initial 60 s of $Mn^{2+}$ exposure yielded a 10-fold higher rate of $Mn^{2+}$-induced quench of fura-2 fluorescence in induced cells (28%/o/min) as compared to uninduced cells (2.9%/min). These results suggest that basal, LTRPC7 activity in intact cells constitutes an important entry pathway for $Mn^{2+}$, and that it would function similarly for other permeant metal ions as well, particularly since $Mn^{2+}$ ranks fairly low in the sequence of permeating divalents (see FIG. 9).

What is claimed is:

1. A method for screening for modulators of LTRPC7 ("Long Transient Receptor Potential Channel"), said method comprising:

a) contacting a cell comprising LTRPC7 polypeptide with a candidate bioactive agent; and b) determining whether said agent modulates the multivalent cationic permeability of a multivalent cation other than $Ca^{2+}$ through LTRPC7 by measuring a change in the intracellular level of said multivalent cation as compared to the multivalent cation permeability in the absence of said candidate agent, wherein said LTRPC7 has an amino acid sequence having at least 95% sequence identity to the sequence of SEQ ID NO:1 and wherein said LTRPC7 is permeable to a multivalent cation in the presence of intracellular ATP concentrations in the 0-4 millimolar range.

2. The method of claim 1 wherein said modulation opens said LTRPC7 channel.

3. The method of claim 1 wherein said modulation closes said LTRPC7.

4. The method of claim 1 where said multivalent cation is selected from the group consisting of $Zn^{2+}$, $Ni^{2+}$, $Ba^{2+}$, $Sr^{2+}$, $Co^{2+}$, $Cd^{2+}$, and $Mg^{2+}$.

5. The method of claim 1 wherein said LTRPC7 has the amino acid sequence of SEQ ID NO:1.

6. A method for screening for modulators of the multivalent cation permeability of LTRPC7 ("Long Transient Receptor Potential Channel"), said method comprising:

a) providing a recombinant cell comprising (i) a recombinant nucleic acid comprising a nucleic acid encoding human LTRPC7 and an inducible promoter operably linked thereto which is capable of expressing said human LTRPC7, and (ii) a multivalent cation indicator;

b) inducing said recombinant cell to express said LTRPC7;

c) contacting said recombinant cell with a multivalent cation and a candidate bioactive agent;

d) determining the intracellular level of said multivalent cation with said indicator; and e) comparing said intracellular level of said multivalent cation in said recombinant cell with the multivalent cation permeability of a recombinant cell expressing LTRPC7 in the absence of said candidate bioactive agent, wherein said LTPRC7 has an amino acid sequence having at least 95% sequence identity to the sequence of SEQ ID NO:1 and wherein said LTRPC7 is permeable to a multivalent cation in the presence of intracellular ATP concentrations in the 0-4 millimolar range.

7. The method of claim 6 wherein said contacting is of said candidate agent followed by said multivalent cation.

8. The method of claim 6 wherein said multivalent cation is selected from the group consisting of $Zn^{2+}$, $Ni^{2+}$, $Ba^{2+}$, $Sr^{2+}$, $Co^{2+}$, $Cd^{2+}$, and $Mg^{2+}$.

9. The method of claim 6 wherein the modulation increases said multivalent cation permeability of said LTRPC7.

10. The method of claim 6 wherein the modulation decreases said multivalent cation permeability of said LTRPC7.

11. The method of claim 6 wherein said indicator comprises a fluorescent molecule.

12. The method of claim 11 wherein said fluorescent molecule comprises fura-2.

13. The method of claim 6 wherein said LTRPC7 has the amino acid sequence of SEQ ID NO:1.

14. A method for measuring multivalent cation permeability of LTRPC7 ("Long Transient Receptor Potential Channel"), said method comprising:
   a) providing a recombinant cell comprising (i) a recombinant nucleic acid which expresses LTRPC7 polypeptide, and (ii) a multivalent cation indicator;
   b) contacting said recombinant cell with a candidate bioative agent and a multivalent cation other than $Ca^{2+}$ which selectively interacts with said indicator to generate a signal; and
   c) measuring said signal to determine the multivalent cation permeability of said recombinant cell as compared to the multivalent cation permeability in the absence of said candidate bioactive agent,
wherein said LTPRC7 has an amino acid sequence having at least 95% sequence identity to the sequence of SEQ ID NO:1 and wherein said LTRPC7 is permeable to a multivalent cation in the presence of intracellular ATP concentrations in the 0-4 millimolar range.

15. The method of claim 14 wherein said indicator comprises a fluorescent molecule.

16. The method of claim 15 wherein said fluorescent molecule comprises fura-2.

17. The method of claim 14 where said multivalent cation is selected from the group consisting of $Zn^{2+}$, $Ni^{2+}$, $Ba^{2+}$, $Sr^{2+}$, $Co^{2+}$, $Cd^{2+}$, and $Mg^{2+}$.

18. The method of claim 14 wherein said modulation increases said multivalent cation permeability of said LTRPC7.

19. The method of claim 14 wherein said modulation decreases said multivalent cation permeability of said LTRPC7.

20. The method of claim 14 wherein said measuring further comprises comparing said multivalent cation permeability to the multivalent cation permeability in a cell which does not express recombinant LTRPC7.

21. The method of claim 14 wherein said LTRPC7 has the amino acid sequence of SEQ ID NO:1.

22. A method for screening modulators of a LTRPC7 ("Long Transient Receptor Potential Channel"), said method comprising:
   a) providing a cell comprising a LTRPC7 polypeptide and a multivalent cation indicator;
   b) contacting said cell with a multivalent cation other than $Ca^{2+}$ and a candidate bioactive agent;
   c) determining the multivalent cation permeability by measuring the intracellular multivalent cation level with said indicator; and
   d) comparing said intracellular multivalent cation level of said cell with (i) the intracellular multivalent cation level of said multivalent cation (i) in a cell which does not express recombinant LTRPC7 or (ii) in a cell in the absence of said candidate agent,
wherein said LTRPC7 polypeptide has an amino acid sequence having at least 95% sequence identity to the sequence of SEQ ID NO:1 and wherein said LTRPC7 is permeable to a multivalent cation in the presence of intracellular ATP concentrations in the 0-4 millimolar range.

23. The method of claim 22 wherein said modulation decreases said multivalent cation permeability of said LTRPC7.

24. The method of claim 22 wherein said modulation increases said multivalent cation permeability of said LTRPC7.

25. The method of claim 22 wherein said contacting is first by said candidate agent followed by said multivalent cation.

26. The method of claim 22 wherein said multivalent cation indicator is fura-2 and said multivalent cation is $Mn^{2+}$.

27. The method of claim 22 wherein said LTRPC7 has the amino acid sequence of SEQ ID NO:1.

28. The method of claims 1, 6, 14, or 22 wherein said candidate agent comprises a small molecule, protein, polypeptide or nucleic acid.

* * * * *

SEQUENCE LISTING

```
<160> NUMBER OF SEQ ID NOS: 10

<210> SEQ ID NO 1
<211> LENGTH: 1865
<212> TYPE: PRT
<213> ORGANISM: Homo sapiens

<400> SEQUENCE: 1

Met Ser Gln Lys Ser Trp Ile Glu Ser Thr Leu Thr Lys Arg Glu Cys
1               5                   10                  15

Val Tyr Ile Ile Pro Ser Ser Lys Asp Pro His Arg Cys Leu Pro Gly
            20                  25                  30

Cys Gln Ile Cys Gln Gln Leu Val Arg Cys Phe Cys Gly Arg Leu Val
        35                  40                  45

Lys Gln His Ala Cys Phe Thr Ala Ser Leu Ala Met Lys Tyr Ser Asp
    50                  55                  60

Val Lys Leu Gly Asp His Phe Asn Gln Ala Ile Glu Glu Trp Ser Val
65                  70                  75                  80

Glu Lys His Thr Glu Gln Ser Pro Thr Asp Ala Tyr Gly Val Ile Asn
                85                  90                  95

Phe Gln Gly Gly Ser His Ser Tyr Arg Ala Lys Tyr Val Arg Leu Ser
            100                 105                 110

Tyr Asp Thr Lys Pro Glu Val Ile Leu Gln Leu Leu Leu Lys Glu Trp
        115                 120                 125

Gln Met Glu Leu Pro Lys Leu Val Ile Ser Val His Gly Gly Met Gln
    130                 135                 140

Lys Phe Glu Leu His Pro Arg Ile Lys Gln Leu Leu Gly Lys Gly Leu
145                 150                 155                 160

Ile Lys Ala Ala Val Thr Thr Gly Ala Trp Ile Leu Thr Gly Gly Val
```

-continued

```
            165                 170                 175
Asn Thr Gly Val Ala Lys His Val Gly Asp Ala Leu Lys Glu His Ala
                180                 185                 190
Ser Arg Ser Ser Arg Lys Ile Cys Thr Ile Gly Ile Ala Pro Trp Gly
            195                 200                 205
Val Ile Glu Asn Arg Asn Asp Leu Val Gly Arg Asp Val Ala Pro
        210                 215                 220
Tyr Gln Thr Leu Leu Asn Pro Leu Ser Lys Leu Asn Val Leu Asn Asn
225                 230                 235                 240
Leu His Ser His Phe Ile Leu Val Asp Asp Gly Thr Val Gly Lys Tyr
                245                 250                 255
Gly Ala Glu Val Arg Leu Arg Arg Glu Leu Glu Lys Thr Ile Asn Gln
                260                 265                 270
Gln Arg Ile His Ala Arg Ile Gly Gln Gly Val Pro Val Val Ala Leu
            275                 280                 285
Ile Phe Glu Gly Gly Pro Asn Val Ile Leu Thr Val Leu Glu Tyr Leu
        290                 295                 300
Gln Glu Ser Pro Pro Val Pro Val Val Cys Glu Gly Thr Gly Arg
305                 310                 315                 320
Ala Ala Asp Leu Leu Ala Tyr Ile His Lys Gln Thr Glu Glu Gly Gly
                325                 330                 335
Asn Leu Pro Asp Ala Ala Glu Pro Asp Ile Ile Ser Thr Ile Lys Lys
                340                 345                 350
Thr Phe Asn Phe Gly Gln Asn Glu Ala Leu His Leu Phe Gln Thr Leu
                355                 360                 365
Met Glu Cys Met Lys Arg Lys Glu Leu Ile Thr Val Phe His Ile Gly
            370                 375                 380
Ser Asp Glu His Gln Asp Ile Asp Val Ala Ile Leu Thr Ala Leu Leu
385                 390                 395                 400
Lys Gly Thr Asn Ala Ser Ala Phe Asp Gln Leu Ile Leu Thr Leu Ala
                405                 410                 415
Trp Asp Arg Val Asp Ile Ala Lys Asn His Val Phe Val Tyr Gly Gln
            420                 425                 430
Gln Trp Leu Val Gly Ser Leu Glu Gln Ala Met Leu Asp Ala Leu Val
        435                 440                 445
Met Asp Arg Val Ala Phe Val Lys Leu Leu Ile Glu Asn Gly Val Ser
        450                 455                 460
Met His Lys Phe Leu Thr Ile Pro Arg Leu Glu Glu Leu Tyr Asn Thr
465                 470                 475                 480
Lys Gln Gly Pro Thr Asn Pro Met Leu Phe His Leu Val Arg Asp Val
                485                 490                 495
Lys Gln Gly Asn Leu Pro Pro Gly Tyr Lys Ile Thr Leu Ile Asp Ile
                500                 505                 510
Gly Leu Val Ile Glu Tyr Leu Met Gly Gly Thr Tyr Arg Cys Thr Tyr
            515                 520                 525
Thr Arg Lys Arg Phe Arg Leu Ile Tyr Asn Ser Leu Gly Gly Asn Asn
        530                 535                 540
Arg Arg Ser Gly Arg Asn Thr Ser Ser Thr Pro Gln Leu Arg Lys
545                 550                 555                 560
Ser His Glu Ser Phe Gly Asn Arg Ala Asp Lys Lys Glu Lys Met Arg
                565                 570                 575
His Asn His Phe Ile Lys Thr Ala Gln Pro Tyr Arg Pro Lys Ile Asp
            580                 585                 590
```

-continued

```
Thr Val Met Glu Glu Gly Lys Lys Arg Thr Lys Asp Glu Ile Val
    595                 600                 605

Asp Ile Asp Asp Pro Glu Thr Lys Arg Phe Pro Tyr Pro Leu Asn Glu
610                 615                 620

Leu Leu Ile Trp Ala Cys Leu Met Lys Arg Gln Val Met Ala Arg Phe
625                 630                 635                 640

Leu Trp Gln His Gly Glu Glu Ser Met Ala Lys Ala Leu Val Ala Cys
                645                 650                 655

Lys Ile Tyr Arg Ser Met Ala Tyr Glu Ala Lys Gln Ser Asp Leu Val
                660                 665                 670

Asp Asp Thr Ser Glu Glu Leu Lys Gln Tyr Ser Asn Asp Phe Gly Gln
            675                 680                 685

Leu Ala Val Glu Leu Leu Glu Gln Ser Phe Arg Gln Asp Glu Thr Met
            690                 695                 700

Ala Met Lys Leu Leu Thr Tyr Glu Leu Lys Asn Trp Ser Asn Ser Thr
705                 710                 715                 720

Cys Leu Lys Leu Ala Val Ser Ser Arg Leu Arg Pro Phe Val Ala His
                725                 730                 735

Thr Cys Thr Gln Met Leu Leu Ser Asp Met Trp Met Gly Arg Leu Asn
            740                 745                 750

Met Arg Lys Asn Ser Trp Tyr Lys Val Ile Leu Ser Ile Leu Val Pro
    755                 760                 765

Pro Ala Ile Leu Leu Leu Glu Tyr Lys Thr Lys Ala Glu Met Ser His
770                 775                 780

Ile Pro Gln Ser Gln Asp Ala His Gln Met Thr Met Asp Asp Ser Glu
785                 790                 795                 800

Asn Asn Phe Gln Asn Ile Thr Glu Glu Ile Pro Met Glu Val Phe Lys
                805                 810                 815

Glu Val Arg Ile Leu Asp Ser Asn Glu Gly Lys Asn Glu Met Glu Ile
                820                 825                 830

Gln Met Lys Ser Lys Lys Leu Pro Ile Thr Arg Lys Phe Tyr Ala Phe
            835                 840                 845

Tyr His Ala Pro Ile Val Lys Phe Trp Phe Asn Thr Leu Ala Tyr Leu
850                 855                 860

Gly Phe Leu Met Leu Tyr Thr Phe Val Val Leu Val Gln Met Glu Gln
865                 870                 875                 880

Leu Pro Ser Val Gln Glu Trp Ile Val Ile Ala Tyr Ile Phe Thr Tyr
                885                 890                 895

Ala Ile Glu Lys Val Arg Glu Ile Phe Met Ser Glu Ala Gly Lys Val
                900                 905                 910

Asn Gln Lys Ile Lys Val Trp Phe Ser Asp Tyr Phe Asn Ile Ser Asp
            915                 920                 925

Thr Ile Ala Ile Ile Ser Phe Phe Ile Gly Phe Gly Leu Arg Phe Gly
    930                 935                 940

Ala Lys Trp Asn Phe Ala Asn Ala Tyr Asp Asn His Val Phe Val Ala
945                 950                 955                 960

Gly Arg Leu Ile Tyr Cys Leu Asn Ile Ile Phe Trp Tyr Val Arg Leu
                965                 970                 975

Leu Asp Phe Leu Ala Val Asn Gln Gln Ala Gly Pro Tyr Val Met Met
            980                 985                 990

Ile Gly Lys Met Val Ala Asn Met  Phe Tyr Ile Val Val  Ile Met Ala
        995                 1000                 1005

Leu Val  Leu Leu Ser Phe Gly  Val Pro Arg Lys Ala  Ile Leu Tyr
    1010                1015                1020
```

Pro His Glu Ala Pro Ser Trp Thr Leu Ala Lys Asp Ile Val Phe
1025                1030                1035

His Pro Tyr Trp Met Ile Phe Gly Glu Val Tyr Ala Tyr Glu Ile
1040                1045                1050

Asp Val Cys Ala Asn Asp Ser Val Ile Pro Gln Ile Cys Gly Pro
1055                1060                1065

Gly Thr Trp Leu Thr Pro Phe Leu Gln Ala Val Tyr Leu Phe Val
1070                1075                1080

Gln Tyr Ile Ile Met Val Asn Leu Leu Ile Ala Phe Phe Asn Asn
1085                1090                1095

Val Tyr Leu Gln Val Lys Ala Ile Ser Asn Ile Val Trp Lys Tyr
1100                1105                1110

Gln Arg Tyr His Phe Ile Met Ala Tyr His Glu Lys Pro Val Leu
1115                1120                1125

Pro Pro Pro Leu Ile Ile Leu Ser His Ile Val Ser Leu Phe Cys
1130                1135                1140

Cys Ile Cys Lys Arg Arg Lys Lys Asp Lys Thr Ser Asp Gly Pro
1145                1150                1155

Lys Leu Phe Leu Thr Glu Glu Asp Gln Lys Lys Leu His Asp Phe
1160                1165                1170

Glu Glu Gln Cys Val Glu Met Tyr Phe Asn Glu Lys Asp Asp Lys
1175                1180                1185

Phe His Ser Gly Ser Glu Glu Arg Ile Arg Val Thr Phe Glu Arg
1190                1195                1200

Val Glu Gln Met Cys Ile Gln Ile Lys Glu Val Gly Asp Arg Val
1205                1210                1215

Asn Tyr Ile Lys Arg Ser Leu Gln Ser Leu Asp Ser Gln Ile Gly
1220                1225                1230

His Leu Gln Asp Leu Ser Ala Leu Thr Val Asp Thr Leu Lys Thr
1235                1240                1245

Leu Thr Ala Gln Lys Ala Ser Glu Ala Ser Lys Val His Asn Glu
1250                1255                1260

Ile Thr Arg Glu Leu Ser Ile Ser Lys His Leu Ala Gln Asn Leu
1265                1270                1275

Ile Asp Asp Gly Pro Val Arg Pro Ser Val Trp Lys Lys His Gly
1280                1285                1290

Val Val Asn Thr Leu Ser Ser Leu Pro Gln Gly Asp Leu Glu
1295                1300                1305

Ser Asn Asn Pro Phe His Cys Asn Ile Leu Met Lys Asp Asp Lys
1310                1315                1320

Asp Pro Gln Cys Asn Ile Phe Gly Gln Asp Leu Pro Ala Val Pro
1325                1330                1335

Gln Arg Lys Glu Phe Asn Phe Pro Glu Ala Gly Ser Ser Ser Gly
1340                1345                1350

Ala Leu Phe Pro Ser Ala Val Ser Pro Pro Glu Leu Arg Gln Arg
1355                1360                1365

Leu His Gly Val Glu Leu Leu Lys Ile Phe Asn Lys Asn Gln Lys
1370                1375                1380

Leu Gly Ser Ser Ser Thr Ser Ile Pro His Leu Ser Ser Pro Pro
1385                1390                1395

Thr Lys Phe Phe Val Ser Thr Pro Ser Gln Pro Ser Cys Lys Ser
1400                1405                1410

His Leu Glu Thr Gly Thr Lys Asp Gln Glu Thr Val Cys Ser Lys

|  | 1415 |  |  |  | 1420 |  |  |  |  | 1425 |  |
|---|---|---|---|---|---|---|---|---|---|---|---|
| Ala | Thr | Glu | Gly | Asp | Asn | Thr | Glu | Phe | Gly | Ala | Phe | Val | Gly | His |
| 1430 | | | | | 1435 | | | | | 1440 | | | | |
| Arg | Asp | Ser | Met | Asp | Leu | Gln | Arg | Phe | Lys | Glu | Thr | Ser | Asn | Lys |
| 1445 | | | | | 1450 | | | | | 1455 | | | | |
| Ile | Lys | Ile | Leu | Ser | Asn | Asn | Asn | Thr | Ser | Glu | Asn | Thr | Leu | Lys |
| 1460 | | | | | 1465 | | | | | 1470 | | | | |
| Arg | Val | Ser | Ser | Leu | Ala | Gly | Phe | Thr | Asp | Cys | His | Arg | Thr | Ser |
| 1475 | | | | | 1480 | | | | | 1485 | | | | |
| Ile | Pro | Val | His | Ser | Lys | Gln | Ala | Glu | Lys | Ile | Ser | Arg | Arg | Pro |
| 1490 | | | | | 1495 | | | | | 1500 | | | | |
| Ser | Thr | Glu | Asp | Thr | His | Glu | Val | Asp | Ser | Lys | Ala | Ala | Leu | Ile |
| 1505 | | | | | 1510 | | | | | 1515 | | | | |
| Pro | Asp | Trp | Leu | Gln | Asp | Arg | Pro | Ser | Asn | Arg | Glu | Met | Pro | Ser |
| 1520 | | | | | 1525 | | | | | 1530 | | | | |
| Glu | Glu | Gly | Thr | Leu | Asn | Gly | Leu | Thr | Ser | Pro | Phe | Lys | Pro | Ala |
| 1535 | | | | | 1540 | | | | | 1545 | | | | |
| Met | Asp | Thr | Asn | Tyr | Tyr | Tyr | Ser | Ala | Val | Glu | Arg | Asn | Asn | Leu |
| 1550 | | | | | 1555 | | | | | 1560 | | | | |
| Met | Arg | Leu | Ser | Gln | Ser | Ile | Pro | Phe | Thr | Pro | Val | Pro | Pro | Arg |
| 1565 | | | | | 1570 | | | | | 1575 | | | | |
| Gly | Glu | Pro | Val | Thr | Val | Tyr | Arg | Leu | Glu | Glu | Ser | Ser | Pro | Asn |
| 1580 | | | | | 1585 | | | | | 1590 | | | | |
| Ile | Leu | Asn | Asn | Ser | Met | Ser | Ser | Trp | Ser | Gln | Leu | Gly | Leu | Cys |
| 1595 | | | | | 1600 | | | | | 1605 | | | | |
| Ala | Lys | Ile | Glu | Phe | Leu | Ser | Lys | Glu | Glu | Met | Gly | Gly | Gly | Leu |
| 1610 | | | | | 1615 | | | | | 1620 | | | | |
| Arg | Arg | Ala | Val | Lys | Val | Gln | Cys | Thr | Trp | Ser | Glu | His | Asp | Ile |
| 1625 | | | | | 1630 | | | | | 1635 | | | | |
| Leu | Lys | Ser | Gly | His | Leu | Tyr | Ile | Ile | Lys | Ser | Phe | Leu | Pro | Glu |
| 1640 | | | | | 1645 | | | | | 1650 | | | | |
| Val | Val | Asn | Thr | Trp | Ser | Ser | Ile | Tyr | Lys | Glu | Asp | Thr | Val | Leu |
| 1655 | | | | | 1660 | | | | | 1665 | | | | |
| His | Leu | Cys | Leu | Arg | Glu | Ile | Gln | Gln | Gln | Arg | Ala | Ala | Gln | Lys |
| 1670 | | | | | 1675 | | | | | 1680 | | | | |
| Leu | Thr | Phe | Ala | Phe | Asn | Gln | Met | Lys | Pro | Lys | Ser | Ile | Pro | Tyr |
| 1685 | | | | | 1690 | | | | | 1695 | | | | |
| Ser | Pro | Arg | Phe | Leu | Glu | Val | Phe | Leu | Leu | Tyr | Cys | His | Ser | Ala |
| 1700 | | | | | 1705 | | | | | 1710 | | | | |
| Gly | Gln | Trp | Phe | Ala | Val | Glu | Glu | Cys | Met | Thr | Gly | Glu | Phe | Arg |
| 1715 | | | | | 1720 | | | | | 1725 | | | | |
| Lys | Tyr | Asn | Asn | Asn | Asn | Gly | Asp | Glu | Ile | Ile | Pro | Thr | Asn | Thr |
| 1730 | | | | | 1735 | | | | | 1740 | | | | |
| Leu | Glu | Glu | Ile | Met | Leu | Ala | Phe | Ser | His | Trp | Thr | Tyr | Glu | Tyr |
| 1745 | | | | | 1750 | | | | | 1755 | | | | |
| Thr | Arg | Gly | Glu | Leu | Leu | Val | Leu | Asp | Leu | Gln | Gly | Val | Gly | Glu |
| 1760 | | | | | 1765 | | | | | 1770 | | | | |
| Asn | Leu | Thr | Asp | Pro | Ser | Val | Ile | Lys | Ala | Glu | Glu | Lys | Arg | Ser |
| 1775 | | | | | 1780 | | | | | 1785 | | | | |
| Cys | Asp | Met | Val | Phe | Gly | Pro | Ala | Asn | Leu | Gly | Glu | Asp | Ala | Ile |
| 1790 | | | | | 1795 | | | | | 1800 | | | | |
| Lys | Asn | Phe | Arg | Ala | Lys | His | His | Cys | Asn | Ser | Cys | Cys | Arg | Lys |
| 1805 | | | | | 1810 | | | | | 1815 | | | | |

| Leu | Lys | Leu | Pro | Asp | Leu | Lys | Arg | Asn | Asp | Tyr | Thr | Pro | Asp | Lys |
|-----|-----|-----|-----|-----|-----|-----|-----|-----|-----|-----|-----|-----|-----|-----|
| 1820 |   |   |   | 1825 |   |   |   |   | 1830 |   |   |   |   |   |

| Ile | Ile | Phe | Pro | Gln | Asp | Glu | Pro | Ser | Asp | Leu | Asn | Leu | Gln | Pro |
|-----|-----|-----|-----|-----|-----|-----|-----|-----|-----|-----|-----|-----|-----|-----|
| 1835 |   |   |   |   | 1840 |   |   |   |   | 1845 |   |   |   |   |

| Gly | Asn | Ser | Thr | Lys | Glu | Ser | Glu | Ser | Thr | Asn | Ser | Val | Arg | Leu |
|-----|-----|-----|-----|-----|-----|-----|-----|-----|-----|-----|-----|-----|-----|-----|
| 1850 |   |   |   |   | 1855 |   |   |   |   | 1860 |   |   |   |   |

Met Leu
    1865

<210> SEQ ID NO 2
<211> LENGTH: 5598
<212> TYPE: DNA
<213> ORGANISM: Homo sapiens

<400> SEQUENCE: 2

```
atgtcccaga atcctggat agaaagcact ttgaccaaga gggaatgtgt atatattata      60
ccaagttcca aggaccctca cagatgcctt ccaggatgtc aaatttgtca gcaactcgtc     120
aggtgttttt gtggtcgctt ggtcaagcaa catgcttgtt ttactgcaag tcttgccatg     180
aaatactcag atgtgaaatt gggtgaccat tttaatcagg aatagaaga atggtctgtg     240
gaaaagcata cagaacagag cccaacggat gcttatggag tcataaattt tcaagggggt     300
tctcattcct acagagctaa gtatgtgagg ctatcatatg acaccaaacc tgaagtcatt     360
ctgcaacttc tgcttaaaga atggcaaatg gagttaccca acttgttat ctctgtacat      420
gggggcatgc agaaatttga gcttcaccca cgaatcaagc agttgcttgg aaaaggtctt     480
attaaagctg cagttacaac tggagcctgg attttaactg gaggagtaaa cacaggtgtg     540
gcaaaacatg ttggagatgc cctcaaagaa catgcttcca gatcatctcg aaagatttgc     600
actatcggaa tagctccatg gggagtgatt gaaaacagaa tgatcttgt tgggagagat      660
gtggttgctc cttatcaaac cttattgaac cccctgagca aattgaatgt tttgaataat     720
ctgcattccc atttcatatt ggtggatgat ggcactgttg aaagtatgg ggcggaagtc      780
agactgagaa gagaacttga aaaaactatt aatcagcaaa gaattcatgc taggattggc     840
cagggtgtcc ctgtggtggc acttatattt gagggtgggc caaatgttat cctcacagtt     900
cttgaatacc ttcaggaaag ccccctgtt ccagtagttg tgtgtgaagg aacaggcaga     960
gctgcagatc tgctagcgta tattcataaa caaacagaag aaggagggaa tcttcctgat    1020
gcagcagagc ccgatattat ttccactatc aaaaaaacat ttaactttgg ccagaatgaa    1080
gcacttcatt tatttcaaac actgatggag tgcatgaaaa gaaggagct tatcactgtt    1140
ttccatattg ggtcagatga acatcaagat atagatgtag caatacttac tgcactgcta    1200
aaaggtacta tgcatctgc atttgaccag cttatcctta cattggcatg ggatagagtt     1260
gacattgcca aaaatcatgt atttgtttat ggacagcagt ggctggttgg atccttggaa    1320
caagctatgc ttgatgctct tgtaatggat agagttgcat ttgtaaaact tcttattgaa    1380
aatggagtaa gcatgcataa attccttacc attccgagac tggaagaact ttacaacact    1440
aaacaaggtc caactaatcc aatgctgttt catcttgttc gagacgtcaa acagggaaat    1500
cttcctccag gatataagat cactctgatt gataaggac ttgttattga atatctcatg     1560
ggaggaaacct acagatgcac ctatactagg aaacgttttc gattaatata taatagtctt    1620
ggtggaaata tcggaggtc tggccgaaat acctccagca gcactcctca gttgcgaaag    1680
agtcatgaat cttttggcaa tagggcgat aaaaagaaa aaatgaggca taaccatttc     1740
attaagacag cacagcccta ccgaccaaag attgatacag ttatggaaga aggaaagaag    1800
```

```
aaaagaacca aagatgaaat tgtagacatt gatgatccag aaaccaagcg ctttccttat    1860
ccacttaatg aacttttaat ttgggcttgc cttatgaaga ggcaggtcat ggcccgtttt    1920
ttatggcaac atggtgaaga atcaatggct aaagcattag ttgcctgtaa gatctatcgt    1980
tcaatggcat atgaagcaaa gcagagtgac ctggtagatg atacttcaga agaactaaaa    2040
cagtattcca atgattttgg tcagttggcc gttgaattat tagaacagtc cttcagacaa    2100
gatgaaacca tggctatgaa attgctcact tatgaactga agaactggag taattcaacc    2160
tgccttaagt tagcagtttc ttcaagactt agaccttttg tagctcacac ctgtacacaa    2220
atgttgttat ctgatatgtg gatgggaagg ctgaatatga ggaaaaattc ctggtacaag    2280
gtcatactaa gcattttagt tccacctgcc atattgctgt tagagtataa aactaaggct    2340
gaaatgtccc atatcccaca atctcaagat gctcatcaga tgacaatgga tgacagcgaa    2400
aacaactttc agaacataac agaagagatc cccatggaag tgtttaaaga agtacggatt    2460
ttggatagta atgaaggaaa gaatgagatg gagatacaaa tgaaatcaaa aaagcttcca    2520
attacgcgaa agttttatgc cttttatcat gcaccaattg taaaattctg gtttaacacg    2580
ttggcatatt taggatttct gatgctttat acatttgtgg ttcttgtaca aatggaacag    2640
ttaccttcag ttcaagaatg gattgttatt gcttatattt ttacttatgc cattgagaaa    2700
gtccgtgaga tctttatgtc tgaagctggg aaagtaaacc agaagattaa agtatggttt    2760
agtgattact tcaacatcag tgatacaatt gccataattt ctttcttcat tggatttgga    2820
ctaagatttg gagcaaaatg gaactttgca aatgcatatg ataatcatgt ttttgtggct    2880
ggaagattaa tttactgtct taacataata ttttggtatg tgcgtttgct agattttcta    2940
gctgtaaatc aacaggcagg accttatgta atgatgattg gaaaaatggt ggccaatatg    3000
ttctacattg tagtgattat ggctcttgta ttacttagtt ttggtgttcc cagaaaggca    3060
atactttatc ctcatgaagc accatcttgg actcttgcta agatatagt ttttcaccca    3120 tactggatga tttttggtga agtttatgca tacgaaattg atgtgtgtgc aaatgattct    3180
gttatccctc aaatctgtgg tcctgggacg tggttgactc catttcttca agcagtctac    3240
ctctttgtac agtatatcat tatggttaat cttcttattg cattttttcaa caatgtgtat    3300 ttacaagtga aggcaatttc caatattgta tggaagtacc agcgttatca ttttattatg    3360
gcttatcatg agaaaccagt tctgcctcct ccacttatca ttcttagcca tatagttct    3420 ctgttttgct gcatatgtaa gagaagaaag aaagataaga cttccgatgg accaaaactt    3480
ttcttaacag aagaagatca aaagaaactt catgattttg aagagcagtg tgttgaaatg    3540
tatttcaatg aaaaagatga caaatttcat tctgggagtg aagagagaat tcgtgtcact    3600
tttgaaagag tggaacagat gtgcattcag attaagaag ttggagatcg tgtcaactac    3660
ataaaaagat cattacaatc attagattct caaattggcc atttgcaaga tctttcagcc    3720
ctgacggtag atacattaaa aacactcact gcccagaaag cgtcggaagc tagcaaagtt    3780
cataatgaaa tcacacgaga actgagcatt tccaaacact ggctcaaaaa ccttattgat    3840
gatggtcctg taagaccttc tgtatggaaa aagcatggtt tgtaaatac acttagctcc    3900 tctcttcctc aaggtgatct tgaaagtaat aatcctttc attgtaatat tttaatgaaa    3960
gatgacaaag atccccagtg taatatattt ggtcaagact tacctgcagt accccagaga    4020
aaagaattta attttccaga ggctggttcc tcttctggtg ccttattccc aagtgctgtt    4080 tccccctccag aactgcgaca gagactacat ggggtagaac tcttaaaaat atttaataaa    4140
aatcaaaaat taggcagttc atctactagc ataccacatc tgtcatcccc accaaccaaa    4200
```

```
tttttttgtta gtacaccatc tcagccaagt tgcaaaagcc acttggaaac tggaaccaaa      4260
gatcaagaaa ctgtttgctc taaagctaca gaaggagata atacagaatt tggagcattt      4320
gtaggacaca gagatagcat ggatttacag aggtttaaag aaacatcaaa caagataaaa      4380
atactatcca ataacaatac ttctgaaaac actttgaaac gagtgagttc tcttgctgga      4440
tttactgact gtcacagaac ttccattcct gttcattcaa acaagcaga aaaaatcagt       4500
agaaggccat ctaccgaaga cactcatgaa gtagattcca agcagctttt aataccggat      4560
tggttacaag atagaccatc aaacagagaa atgccatctg aagaaggaac attaaatggt      4620
ctcacttctc catttaagcc agctatggat acaaattact attattcagc tgtggaaaga      4680
aataacttga tgaggttatc acagagcatt ccatttacac ctgtgcctcc aagaggggag      4740
cctgtcacag tgtatcgttt ggaagagagt tcacccaaca tactaaataa cagcatgtct      4800
tcttggtcac aactaggcct ctgtgccaaa atagagttt taagcaaaga ggagatggga      4860
ggaggtttac gaagagctgt caaagtacag tgtacctggt cagaacatga tatcctcaaa      4920
tcagggcatc tttatattat caaatctttt cttccagagg tggttaatac atggtcaagt      4980
atttataaag aagatacagt tctgcatctc tgtctgagag aaattcaaca acagagagca      5040
gcacaaaagc ttacgtttgc ctttaatcaa atgaaaccca atccatacc atattctcca       5100
aggttccttg aagtttttcct gctgtattgc cattcagcag acagtggtt tgctgtggaa       5160
gaatgtatga ctggagaatt tagaaaatac aacaataata atggagatga gattattcca      5220
actaatactc tggaagagat catgctagcc tttagccact ggacttacga atatacaaga      5280
ggggagttac tggtacttga tttgcaaggt gttggtgaaa atttgactga cccatctgtg      5340
ataaaagcag aagaaaagag atcctgtgat atggttttttg gcccagcaaa tctaggagaa      5400
gatgcaatta aaaacttcag agcaaaacat cactgtaatt cttgctgtag aaagcttaaa      5460
cttccagatc tgaagaggaa tgattatacg cctgataaaa ttatatttcc tcaggatgag      5520
ccttcagatt tgaatcttca gcctggaaat tccaccaaag aatcagaatc aactaattct      5580
gttcgtctga tgttataa                                                    5598
```

<210> SEQ ID NO 3
<211> LENGTH: 7259
<212> TYPE: DNA
<213> ORGANISM: Homo sapiens
<220> FEATURE:
<221> NAME/KEY: misc_feature
<222> LOCATION: (48)..(48)
<223> OTHER INFORMATION: "n" at position 48 can be any base.
<220> FEATURE:
<221> NAME/KEY: misc_feature
<222> LOCATION: (6856)..(6894)
<223> OTHER INFORMATION: "n" at positions 6856, 6874 and 6894 can be any base.
<220> FEATURE:
<221> NAME/KEY: misc_feature
<222> LOCATION: (7230)..(7248)
<223> OTHER INFORMATION: "n" at positions 7230, 7231 and 7248 can be any base.

<400> SEQUENCE: 3

```
ccacgcgtcc gcagccccgt cgccggcgga ggcgggcgcg ggcgcgtncc ctgtggccag       60
tcacccggag gagttggtcg cacaattatg aaagactcgg cttctgctgc tagcgccgga      120
gctgagttag ttctgagaag gtttccctgg gcgttccttg tccggcggcc tctgctgccg      180
cctccggaga cgcttcccga tagatggcta caggccgcgg aggaggagga ggtggagttg      240
ctgcccttcc ggagtccgcc ccgtgaggag aatgtcccag aaatcctgga tagaaagcac      300
```

```
tttgaccaag agggaatgtg tatatattat accaagttcc aaggaccctc acagatgcct    360
tccaggatgt caaatttgtc agcaactcgt caggtgtttt tgtggtcgct tggtcaagca    420
acatgcttgt tttactgcaa gtcttgccat gaaatactca gatgtgaaat tgggtgacca    480
ttttaatcag gcaatagaag aatggtctgt ggaaaagcat acagaacaga gcccaacgga    540
tgcttatgga gtcataaatt ttcaaggggg ttctcattcc tacagagcta agtatgtgag    600
gctatcatat gacaccaaac ctgaagtcat tctgcaactt ctgcttaaag aatggcaaat    660
ggagttaccc aaacttgtta tctctgtaca tgggggcatg cagaaatttg agcttcaccc    720
acgaatcaag cagttgcttg aaaaggtct tattaaagct gcagttacaa ctggagcctg    780
gattttaact ggaggagtaa acacaggtgt ggcaaaacat gttggagatg ccctcaaaga    840
acatgcttcc agatcatctc gaaagatttg cactatcgga atagctccat ggggagtgat    900
tgaaaacaga aatgatcttg ttgggagaga tgtggttgct ccttatcaaa ccttattgaa    960 cccctgagc aaattgaatg ttttgaataa tctgcattcc catttcatat tggtggatga    1020
tggcactgtt ggaaagtatg gggcggaagt cagactgaga agagaacttg aaaaaactat    1080
taatcagcaa agaattcatg ctaggattgg ccagggtgtc cctgtggtgg cacttatatt    1140
tgagggtggg ccaaatgtta tcctcacagt tcttgaatac cttcaggaaa gcccccctgt    1200
tccagtagtt gtgtgtgaag gaacaggcag agctgcagat ctgctagcgt atattcataa    1260
acaaacagaa gaaggaggga atcttcctga tgcagcagag cccgatatta tttccactat    1320
caaaaaaaca tttaactttg gccagaatga agcacttcat ttatttcaaa cactgatgga    1380
gtgcatgaaa agaaaggagc ttatcactgt tttccatatt gggtcagatg aacatcaaga    1440
tatagatgta gcaatactta ctgcactgct aaaaggtact aatgcatctg catttgacca    1500
gcttatcctt acattggcat gggatagagt tgacattgcc aaaaatcatg tatttgttta    1560
tggacagcag tggctggttg atccttgga caagctatg cttgatgctc ttgtaatgga    1620
tagagttgca tttgtaaaac ttcttattga aaatggagta agcatgcata aattccttac    1680
cattccgaga ctggaagaac tttacaacac taaacaaggt ccaactaatc caatgctgtt    1740
tcatcttgtt cgagacgtca acagggaaa tcttcctcca ggatataaga tcactctgat    1800
tgatatagga cttgttattg aatatctcat gggaggaacc tacagatgca cctatactag    1860
gaaacgtttt cgattaatat ataatagtct tggtggaaat aatcggaggt ctggccgaaa    1920
tacctccagc agcactcctc agttgcgaaa gagtcatgaa tcttttggca atagggcaga    1980
taaaaaggaa aaaatgaggc ataaccattt cattaagaca gcacagccct accgaccaaa    2040
gattgataca gttatggaag aaggaaagaa gaaagaacc aaagatgaaa ttgtagacat    2100
tgatgatcca gaaaccaagc gctttcctta tccacttaat gaactttaa tttgggcttg    2160 ccttatgaag aggcaggtca tggcccgttt tttatggcaa catggtgaag aatcaatggc    2220
taaagcatta gttgcctgta agatctatcg ttcaatggca tatgaagcaa gcagagtga    2280 cctggtagat gatacttcag aagaactaaa acagtattcc aatgattttg gtcagttggc    2340
cgttgaatta ttagaacagt ccttcagaca agatgaaacc atggctatga aattgctcac    2400
ttatgaactg aagaactgga gtaattcaac ctgccttaag ttagcagttt cttcaagact    2460
tagacctttt gtagctcaca cctgtacaca aatgttgtta tctgatatgt ggatgggaag    2520
gctgaatatg aggaaaaatt cctggtacaa ggtcatacta agcattttag ttccacctgc    2580
catattgctg ttagagtata aaactaaggc tgaaatgtcc catatcccac aatctcaaga    2640
tgctcatcag atgacaatgg atgacagcga aacaacttc cagaacataa cagaagagat    2700
```

```
ccccatggaa gtgtttaaag aagtacggat tttggatagt aatgaaggaa agaatgagat    2760
ggagatacaa atgaaatcaa aaaagcttcc aattacgcga aagttttatg ccttttatca    2820
tgcaccaatt gtaaaattct ggtttaacac gttggcatat ttaggatttc tgatgcttta    2880
tacatttgtg gttcttgtac aaatggaaca gttaccttca gttcaagaat ggattgttat    2940
tgcttatatt tttacttatg ccattgagaa agtccgtgag atctttatgt ctgaagctgg    3000
gaaagtaaac cagaagatta agtatggtt tagtgattac ttcaacatca gtgatacaat    3060
tgccataatt tctttcttca ttggatttgg actaagattt ggagcaaaat ggactttgc    3120 aaatgcatat gataatcatg tttttgtggc tggaagatta atttactgtc ttaacataat    3180
attttggtat gtgcgtttgc tagattttct agctgtaaat caacaggcag gaccttatgt    3240
aatgatgatt ggaaaaatgg tggccaatat gttctacatt gtagtgatta tggctcttgt    3300
attacttagt tttggtgttc ccagaaaggc aatactttat cctcatgaag caccatcttg    3360
gactcttgct aaagatatag ttttcaccc atactggatg attttttggtg aagttttatgc    3420 atacgaaatt gatgtgtgtg caaatgattc tgttatccct caaatctgtg gtcctgggac    3480
gtggttgact ccattcttc aagcagtcta cctctttgta cagtatatca ttatggttaa    3540
tcttcttatt gcattttca acaatgtgta tttacaagtg aaggcaattt ccaatattgt    3600
atggaagtac cagcgttatc attttattat ggcttatcat gagaaaccag ttctgcctcc    3660
tccacttatc attcttagcc atatagtttc tctgttttgc tgcatatgta agagaagaaa    3720
gaaagataag acttccgatg gaccaaaact tttcttaaca gaagaagatc aaaagaaact    3780
tcatgatttt gaagagcagt gtgttgaaat gtatttcaat gaaaaagatg acaaatttca    3840
ttctgggagt gaagagagaa ttcgtgtcac ttttgaaaga gtggaacaga tgtgcattca    3900
gattaaagaa gttggagatc gtgtcaacta cataaaaaga tcattacaat cattagattc    3960
tcaaattggc catttgcaag atctttcagc cctgacggta gatacattaa aaacactcac    4020
tgcccagaaa gcgtcggaag ctagcaaagt tcataatgaa atcacacgag aactgagcat    4080
ttccaaacac ttggctcaaa accttattga tgatggtcct gtaagacctt ctgtatggaa    4140
aaagcatggt gttgtaaata cacttagctc ctctcttcct caaggtgatc ttgaaagtaa    4200 taatccttt cattgtaata ttttaatgaa agatgacaaa gatccccagt gtaatatatt    4260
tggtcaagac ttacctgcag taccccagag aaaagaattt aattttccag aggctggttc    4320
ctcttctggt gccttattcc caagtgctgt ttcccctcca gaactgcgac agagactaca    4380
tggggtagaa ctcttaaaaa tatttaataa aaatcaaaaa ttaggcagtt catctactag    4440
cataccacat ctgtcatccc caccaaccaa atttttgtt agtacaccat ctcagccaag    4500
ttgcaaaagc cacttggaaa ctggaaccaa agatcaagaa actgtttgct ctaaagctac    4560
agaaggagat aatacagaat ttggagcatt tgtaggacac agagatagca tggatttaca    4620
gaggtttaaa gaaacatcaa acaagataaa aatactatcc aataacaata cttctgaaaa    4680
cactttgaaa cgagtgagtt ctcttgctgg atttactgac tgtcacagaa cttccattcc    4740
tgttcattca aaacaagcag aaaaaatcag tagaaggcca tctaccgaag acactcatga    4800
agtagattcc aaagcagctt taataccgga ttggttacaa gatagaccat caaacagaga    4860
aatgccatct gaagaaggaa cattaaatgg tctcacttct ccatttaagc cagctatgga    4920
tacaaattac tattattcag ctgtggaaag aaataacttg atgaggttat cacagagcat    4980
tccatttaca cctgtgcctc caagagggga gcctgtcaca gtgtatcgtt tggaagagag    5040
ttcacccaac atactaaata acagcatgtc ttcttggtca caactaggcc tctgtgccaa    5100
```

-continued

```
aatagagttt ttaagcaaag aggagatggg aggaggttta cgaagagctg tcaaagtaca   5160
gtgtacctgg tcagaacatg atatcctcaa atcagggcat cttatatta tcaaatcttt   5220 tcttccagag gtggttaata catggtcaag tatttataaa aagatacag ttctgcatct   5280 ctgtctgaga gaaattcaac aacagagagc agcacaaaag cttacgtttg cctttaatca   5340
aatgaaaccc aaatccatac catattctcc aaggttcctt gaagttttcc tgctgtattg   5400
ccattcagca ggacagtggt ttgctgtgga agaatgtatg actggagaat ttagaaaata   5460
caacaataat aatggagatg agattattcc aactaatact ctggaagaga tcatgctagc   5520
ctttagccac tggacttacg aatatacaag aggggagtta ctggtacttg atttgcaagg   5580
tgttggtgaa aatttgactg acccatctgt gataaaagca aagaaaaga gatcctgtga   5640 tatggttttt ggcccagcaa atctaggaga agatgcaatt aaaaacttca gagcaaaaca   5700
tcactgtaat tcttgctgta gaaagcttaa acttccagat ctgaagagga atgattatac   5760
gcctgataaa attatatttc ctcaggatga gccttcagat ttgaatcttc agcctggaaa   5820
ttccaccaaa gaatcagaat caactaattc tgttcgtctg atgttataat attaatatta   5880
ctgaatcatt ggttttgcct gcacctcaca gaaatgttac tgtgtcactt ttccctcggg   5940
aggaaattgt ttggtaatat agaaaggtgt atgcaagttg aatttgctga ctccagcaca   6000
gttaaaaggt caatattctt ttgacctgat taatcagtca gaaagtccct ataggataga   6060
gctggcagct gagaaatttt aaaggtaatt gataattagt atttgtaact ttttaaaggg   6120
ctctttgtat agcagaggat ctcatttgac tttgttttga tgagggtgat gccctctctt   6180
atgtggtaca ataccattaa ccaaaggtag gtgtccatgc agattttatt ggcagctgtt   6240
ttattgccat tcaactaggg aaatgaagaa atcacgcagc cttttggtta aatggcagtc   6300 aaaatttttcc tcagtgtatt tagtgtgttc agtgatgata tcactggttc ccaactagat   6360
gcttgttggc cacgggaagg gaaatgactt gttctaattc taggttcaca gaggtatgag   6420
aagcctgaac tgaagaccat tttcaagagg gacggtattt atgaatcagg gttaggctcc   6480
atatttaaag atagagccag ttttttttttt aaatagaacc caaattgtgt aaaaatgtta   6540
attgggtttt ttaaacattg ttttatcaag tcactgttaa gtagaagaaa gccatggtaa   6600
actgatacat aacctaaatt ataaaagcag aaacctaact cactcgtcaa gggaagttac   6660
cttttgagga aagttaaagt actttttttcc ctatctgtat ctatagcaac aacccagaac   6720
ttacaaactt ctccaaagat tttattgatt gttatatcaa atcagaatgt aaacatgaac   6780
tcttgcatat atttaaaatt gtgttggaac atttgaacat gaatgctgtt tgggtactta   6840
agaaattrat tcagtnggat tatcattatg tganactggc agattgcagt gcanccttat   6900
gccaataaaa tgtaatttaa cagccccaga tattgttgaa tattcaacaa taacaagaaa   6960
agcttttcat ctaagtttta tgctttaatt tttttctttt tttttctttt ttcttttgtt   7020
tccttggtac taattttaat ttttatttgg aagggagcag tataaagctt atttgtatt    7080 agtagtgtat ctcatagata cagacaaggc aagagatgat aagctgttta aatagtgttt   7140
aatattgatt gggggtgggg agaaagaaaa agtgtattac ttaaagatac tatatacgtt   7200
ttgtatatca ttaaatcttt aaaagaaatn naataaattt attgtttnca aaaaaaaaa   7259
```

<210> SEQ ID NO 4
<211> LENGTH: 1863
<212> TYPE: PRT
<213> ORGANISM: Mus musculus

<400> SEQUENCE: 4

-continued

```
Met Ser Gln Lys Ser Trp Ile Glu Ser Thr Leu Thr Lys Arg Glu Cys
1               5                   10                  15

Val Tyr Ile Ile Pro Ser Ser Lys Asp Pro His Arg Cys Leu Pro Gly
            20                  25                  30

Cys Gln Ile Cys Gln Gln Leu Val Arg Cys Phe Cys Gly Arg Leu Val
            35                  40                  45

Lys Gln His Ala Cys Phe Thr Ala Ser Leu Ala Met Lys Tyr Ser Asp
50                  55                  60

Val Lys Leu Gly Glu His Phe Asn Gln Ala Ile Glu Glu Trp Ser Val
65                  70                  75                  80

Glu Lys His Thr Glu Gln Ser Pro Thr Asp Ala Tyr Gly Val Ile Asn
                85                  90                  95

Phe Gln Gly Gly Ser His Ser Tyr Arg Ala Lys Tyr Val Arg Leu Ser
            100                 105                 110

Tyr Asp Thr Lys Pro Glu Ile Ile Leu Gln Leu Leu Leu Lys Glu Trp
        115                 120                 125

Gln Met Glu Leu Pro Lys Leu Val Ile Ser Val His Gly Gly Met Gln
        130                 135                 140

Lys Phe Glu Leu His Pro Arg Ile Lys Gln Leu Leu Gly Lys Gly Leu
145                 150                 155                 160

Ile Lys Ala Ala Val Thr Thr Gly Ala Trp Ile Leu Thr Gly Gly Val
                165                 170                 175

Asn Thr Gly Val Ala Lys His Val Gly Asp Ala Leu Lys Glu His Ala
                180                 185                 190

Ser Arg Ser Ser Arg Lys Ile Cys Thr Ile Gly Ile Ala Pro Trp Gly
        195                 200                 205

Val Ile Glu Asn Arg Asn Asp Leu Val Gly Arg Asp Val Val Ala Pro
210                 215                 220

Tyr Gln Thr Leu Leu Asn Pro Leu Ser Lys Leu Asn Val Leu Asn Asn
225                 230                 235                 240

Leu His Ser His Phe Ile Leu Val Asp Asp Gly Thr Val Gly Lys Tyr
                245                 250                 255

Gly Ala Glu Val Arg Leu Arg Arg Glu Leu Glu Lys Thr Ile Asn Gln
            260                 265                 270

Gln Arg Ile His Ala Arg Ile Gly Gln Gly Val Pro Val Val Ala Leu
        275                 280                 285

Ile Phe Glu Gly Gly Pro Asn Val Ile Leu Thr Val Leu Glu Tyr Leu
        290                 295                 300

Gln Glu Ser Pro Pro Val Pro Val Val Cys Glu Gly Thr Gly Arg Ala
305                 310                 315                 320

Ala Ala Asp Leu Leu Ala Tyr Ile His Lys Gln Thr Glu Glu Gly Gly
                325                 330                 335

Asn Leu Pro Asp Ala Ala Glu Pro Asp Ile Ile Ser Thr Ile Lys Lys
            340                 345                 350

Thr Phe Asn Phe Gly Gln Ser Glu Ala Val His Leu Phe Gln Thr Met
        355                 360                 365

Met Glu Cys Met Lys Lys Lys Glu Leu Ile Thr Val Phe His Ile Gly
        370                 375                 380

Ser Glu Asp His Gln Asp Ile Asp Val Ala Ile Leu Thr Ala Leu Leu
385                 390                 395                 400

Lys Gly Thr Asn Ala Ser Ala Phe Asp Gln Leu Ile Leu Thr Leu Ala
            405                 410                 415

Trp Asp Arg Val Asp Ile Ala Lys Asn His Val Phe Val Tyr Gly Gln
            420                 425                 430
```

```
Gln Trp Leu Val Gly Ser Leu Glu Gln Ala Met Leu Asp Ala Leu Val
            435                 440                 445

Met Asp Arg Val Ser Phe Val Lys Leu Leu Ile Glu Asn Gly Val Ser
450                 455                 460

Met His Lys Phe Leu Thr Ile Pro Arg Leu Glu Leu Tyr Asn Thr
465                 470                 475                 480

Lys Gln Gly Pro Thr Asn Pro Met Leu Phe His Leu Ile Arg Asp Val
                485                 490                 495

Lys Gln Gly Asn Leu Pro Pro Gly Tyr Lys Ile Thr Leu Ile Asp Ile
                500                 505                 510

Gly Leu Val Ile Glu Tyr Leu Met Gly Gly Thr Tyr Arg Cys Thr Tyr
                515                 520                 525

Thr Arg Lys Arg Phe Arg Leu Ile Tyr Asn Ser Leu Gly Gly Asn Asn
530                 535                 540

Arg Arg Ser Gly Arg Asn Thr Ser Ser Ser Thr Pro Gln Leu Arg Lys
545                 550                 555                 560

Ser His Glu Thr Phe Gly Asn Arg Ala Asp Lys Lys Glu Lys Met Arg
                565                 570                 575

His Asn His Phe Ile Lys Thr Ala Gln Pro Tyr Arg Pro Lys Met Asp
                580                 585                 590

Ala Ser Met Glu Glu Gly Lys Lys Lys Arg Thr Lys Asp Glu Ile Val
                595                 600                 605

Asp Ile Asp Asp Pro Glu Thr Lys Arg Phe Pro Tyr Pro Leu Asn Glu
610                 615                 620

Leu Leu Ile Trp Ala Cys Leu Met Lys Arg Gln Val Met Ala Arg Phe
625                 630                 635                 640

Leu Trp Gln His Gly Glu Glu Ser Met Ala Lys Ala Leu Val Ala Cys
                645                 650                 655

Lys Ile Tyr Arg Ser Met Ala Tyr Glu Ala Lys Gln Ser Asp Leu Val
                660                 665                 670

Asp Asp Thr Ser Glu Glu Leu Lys Gln Tyr Ser Asn Asp Phe Gly Gln
                675                 680                 685

Leu Ala Val Glu Leu Leu Glu Gln Ser Phe Arg Gln Asp Glu Thr Met
                690                 695                 700

Ala Met Lys Leu Leu Thr Tyr Glu Leu Lys Asn Trp Ser Asn Ser Thr
705                 710                 715                 720

Cys Leu Lys Leu Ala Val Ser Ser Arg Leu Arg Pro Phe Val Ala His
                725                 730                 735

Thr Cys Thr Gln Met Leu Leu Ser Asp Met Trp Met Gly Arg Leu Asn
                740                 745                 750

Met Arg Lys Asn Ser Trp Tyr Lys Val Ile Leu Ser Ile Leu Val Pro
                755                 760                 765

Pro Ala Ile Leu Met Leu Glu Tyr Lys Thr Lys Ala Glu Met Ser His
770                 775                 780

Ile Pro Gln Ser Gln Asp Ala His Gln Met Thr Met Glu Asp Ser Glu
785                 790                 795                 800

Asn Asn Phe His Asn Ile Thr Glu Glu Ile Pro Met Glu Val Phe Lys
                805                 810                 815

Glu Val Lys Ile Leu Asp Ser Ser Asp Gly Lys Asn Glu Met Glu Ile
                820                 825                 830

His Ile Lys Ser Lys Lys Leu Pro Ile Thr Arg Lys Phe Tyr Ala Phe
                835                 840                 845

Tyr His Ala Pro Ile Val Lys Phe Trp Phe Asn Thr Leu Ala Tyr Leu
```

-continued

```
            850                 855                 860
Gly Phe Leu Met Leu Tyr Thr Phe Val Leu Val Lys Met Glu Gln
865                 870                 875                 880

Leu Pro Ser Val Gln Glu Trp Ile Val Ile Ala Tyr Ile Phe Thr Tyr
                885                 890                 895

Ala Ile Glu Lys Val Arg Glu Val Phe Met Ser Glu Ala Gly Lys Ile
                900                 905                 910

Ser Gln Lys Ile Lys Val Trp Phe Ser Asp Tyr Phe Asn Val Ser Asp
                915                 920                 925

Thr Ile Ala Ile Ile Ser Phe Phe Val Gly Phe Gly Leu Arg Phe Gly
930                 935                 940

Ala Lys Trp Asn Tyr Ile Asn Ala Tyr Asp Asn His Val Phe Val Ala
945                 950                 955                 960

Gly Arg Leu Ile Tyr Cys Leu Asn Ile Ile Phe Trp Tyr Val Arg Leu
                965                 970                 975

Leu Asp Phe Leu Ala Val Asn Gln Gln Ala Gly Pro Tyr Val Met Met
                980                 985                 990

Ile Gly Lys Met Val Ala Asn Met  Phe Tyr Ile Val Val  Ile Met Ala
                995                 1000                1005

Leu Val  Leu Leu Ser Phe Gly  Val Pro Arg Lys Ala  Ile Leu Tyr
1010                1015                1020

Pro His  Glu Glu Pro Ser Trp  Ser Leu Ala Lys Asp  Ile Val Phe
1025                1030                1035

His Pro  Tyr Trp Met Ile Phe  Gly Glu Val Tyr Ala  Tyr Glu Ile
1040                1045                1050

Asp Val  Cys Ala Asn Asp Ser  Thr Leu Pro Thr Ile  Cys Gly Pro
1055                1060                1065

Gly Thr  Trp Leu Thr Pro Phe  Leu Gln Ala Val Tyr  Leu Phe Val
1070                1075                1080

Gln Tyr  Ile Ile Met Val Asn  Leu Leu Ile Ala Phe  Phe Asn Asn
1085                1090                1095

Val Tyr  Leu Gln Val Lys Ala  Ile Ser Asn Ile Val  Trp Lys Tyr
1100                1105                1110

Gln Arg  Tyr His Phe Ile Met  Ala Tyr His Glu Lys  Pro Val Leu
1115                1120                1125

Pro Pro  Pro Leu Ile Ile Leu  Ser His Ile Val Ser  Leu Phe Cys
1130                1135                1140

Cys Val  Cys Lys Arg Arg Lys  Lys Asp Lys Thr Ser  Asp Gly Pro
1145                1150                1155

Lys Leu  Phe Leu Thr Glu Glu  Asp Gln Lys Lys Leu  His Asp Phe
1160                1165                1170

Glu Glu  Gln Cys Val Glu Met  Tyr Phe Asp Glu Lys  Asp Asp Lys
1175                1180                1185

Phe Asn  Ser Gly Ser Glu Glu  Arg Ile Arg Val Thr  Phe Glu Arg
1190                1195                1200

Val Glu  Gln Met Ser Ile Gln  Ile Lys Glu Val Gly  Asp Arg Val
1205                1210                1215

Asn Tyr  Ile Lys Arg Ser Leu  Gln Ser Leu Asp Ser  Gln Ile Gly
1220                1225                1230

His Leu  Gln Asp Leu Ser Ala  Leu Thr Val Asp Thr  Leu Lys Thr
1235                1240                1245

Leu Thr  Ala Gln Lys Ala Ser  Glu Ala Ser Lys Val  His Asn Glu
1250                1255                1260
```

-continued

```
Ile Thr Arg Glu Leu Ser Ile Ser Lys His Leu Ala Gln Asn Leu
1265                1270                1275

Ile Asp Asp Val Pro Val Arg Pro Leu Trp Lys Lys Pro Ser Ala
1280                1285                1290

Val Asn Thr Leu Ser Ser Ser Leu Pro Gln Gly Asp Arg Glu Ser
    1295                1300                1305

Asn Asn Pro Phe Leu Cys Asn Ile Phe Met Lys Asp Glu Lys Asp
    1310                1315                1320

Pro Gln Tyr Asn Leu Phe Gly Gln Asp Leu Pro Val Ile Pro Gln
    1325                1330                1335

Arg Lys Glu Phe Asn Ile Pro Glu Ala Gly Ser Ser Cys Gly Ala
    1340                1345                1350

Leu Phe Pro Ser Ala Val Ser Pro Pro Glu Leu Arg Gln Arg Arg
    1355                1360                1365

His Gly Val Glu Met Leu Lys Ile Phe Asn Lys Asn Gln Lys Leu
    1370                1375                1380

Gly Ser Ser Pro Asn Ser Ser Pro His Met Ser Pro Pro Thr
    1385                1390                1395

Lys Phe Ser Val Ser Thr Pro Ser Gln Pro Ser Cys Lys Ser His
    1400                1405                1410

Leu Glu Ser Thr Thr Lys Asp Gln Glu Pro Ile Phe Tyr Lys Ala
    1415                1420                1425

Ala Glu Gly Asp Asn Ile Glu Phe Gly Ala Phe Val Gly His Arg
    1430                1435                1440

Asp Ser Met Asp Leu Gln Arg Phe Lys Glu Thr Ser Asn Lys Ile
    1445                1450                1455

Arg Glu Leu Leu Ser Asn Asp Thr Pro Glu Asn Thr Leu Lys His
    1460                1465                1470

Val Gly Ala Ala Gly Tyr Ser Glu Cys Cys Lys Thr Ser Thr Ser
    1475                1480                1485

Leu His Ser Val Gln Ala Glu Ser Cys Ser Arg Arg Ala Ser Thr
    1490                1495                1500

Glu Asp Ser Pro Glu Val Asp Ser Lys Ala Ala Leu Leu Pro Asp
    1505                1510                1515

Trp Leu Arg Asp Arg Pro Ser Asn Arg Glu Met Pro Ser Glu Gly
    1520                1525                1530

Gly Thr Leu Asn Gly Leu Ala Ser Pro Phe Lys Pro Val Leu Asp
    1535                1540                1545

Thr Asn Tyr Tyr Tyr Ser Ala Val Glu Arg Asn Asn Leu Met Arg
    1550                1555                1560

Leu Ser Gln Ser Ile Pro Phe Val Pro Val Pro Pro Arg Gly Glu
    1565                1570                1575

Pro Val Thr Val Tyr Arg Leu Glu Glu Ser Ser Pro Ser Ile Leu
    1580                1585                1590

Asn Asn Ser Met Ser Ser Trp Ser Gln Leu Gly Leu Cys Ala Lys
    1595                1600                1605

Ile Glu Phe Leu Ser Lys Glu Glu Met Gly Gly Gly Leu Arg Arg
    1610                1615                1620

Ala Val Lys Val Leu Cys Thr Trp Ser Glu His Asp Ile Leu Lys
    1625                1630                1635

Ser Gly His Leu Tyr Ile Ile Lys Ser Phe Leu Pro Glu Val Ile
    1640                1645                1650

Asn Thr Trp Ser Ser Ile Tyr Lys Glu Asp Thr Val Leu His Leu
    1655                1660                1665
```

```
Cys Leu Arg Glu Ile Gln Gln Gln Arg Ala Ala Gln Lys Leu Thr
    1670            1675                1680
Phe Ala Phe Asn Gln Met Lys Pro Lys Ser Ile Pro Tyr Ser Pro
    1685            1690                1695
Arg Phe Leu Glu Val Phe Leu Tyr Cys His Ser Ala Gly Gln
    1700            1705                1710
Trp Phe Ala Val Glu Glu Cys Met Thr Gly Glu Phe Arg Lys Tyr
    1715            1720                1725
Asn Asn Asn Asn Gly Asp Glu Ile Ile Pro Thr Asn Thr Leu Glu
    1730            1735                1740
Glu Ile Met Leu Ala Phe Ser His Trp Thr Tyr Glu Tyr Thr Arg
    1745            1750                1755
Gly Glu Leu Leu Val Leu Asp Leu Gln Gly Val Gly Glu Asn Leu
    1760            1765                1770
Thr Asp Pro Ser Val Ile Lys Ala Glu Glu Lys Arg Ser Cys Asp
    1775            1780                1785
Met Val Phe Gly Pro Ala Asn Leu Gly Glu Asp Ala Ile Lys Asn
    1790            1795                1800
Phe Arg Ala Lys His His Cys Asn Ser Cys Cys Arg Lys Leu Lys
    1805            1810                1815
Leu Pro Asp Leu Lys Arg Asn Asp Tyr Thr Pro Asp Lys Ile Ile
    1820            1825                1830
Phe Pro Gln Asp Glu Ser Ser Asp Leu Asn Leu Gln Ser Gly Asn
    1835            1840                1845
Ser Thr Lys Glu Ser Glu Ala Thr Asn Ser Val Arg Leu Met Leu
    1850            1855                1860

<210> SEQ ID NO 5
<211> LENGTH: 5592
<212> TYPE: DNA
<213> ORGANISM: Mus musculus

<400> SEQUENCE: 5
atgtcccaga atcctggat  agagagcact ttgaccaaga gggagtgtgt atatattata    60
ccaagctcca aagaccctca cagatgtctt ccaggatgtc agatttgtca gcaacttgtc   120
agatgtttct gtggtcgttt ggtcaagcaa catgcatgct ttactgcaag tcttgccatg   180
aaatactcag atgtgaaatt gggtgaacac tttaaccagg caatagaaga atggtctgtg   240
gaaaagcaca cggagcagag cccaacagat gcttatggag tcatcaattt tcaagggggt   300
tctcattcct acagagctaa gtatgtgaga ctatcatatg ataccaaacc tgaaatcatt   360
ctgcaacttc tgcttaaaga atggcaaatg gagttaccca acttgttat ttctgtacat   420
ggaggcatgc agaagtttga acttcatcca gaatcaagc agttgcttgg aaagggtctt   480
attaaagctg cagttacaac cggagcttgg atttaactg gaggagtcaa tacaggtgtg   540
gcaaaacatg ttggtgatgc cctcaaagaa catgcttcca gatcatctcg aaaaatttgc   600
actattggaa tagctccatg gggagtgata gaaaacagaa atgatcttgt tgggagagat   660
gtggttgctc cttatcaaac cctattgaat ccttgagca aattgaatgt tctgaataat   720
ctacactccc atttcatctt ggtggatgat ggcactgttg aaagtatgg ggcagaagtc   780
agactgagaa gagaacttga aaaaaccatt aatcagcaaa gaattcatgc tagaattggg   840
caaggagttc ctgtggtggc tttgatattt gaaggcgggc caaatgtcat ccttacagta   900
ctggagtacc ttcaggaaag cccccccagtt ccagttgttg tgtgtgaagg acaggcagga   960
```

```
gctgcagatt tactagccta tatccacaaa cagacagagg aaggaggaaa tcttcctgat    1020
gcagcagagc ctgatattat atcaactatc aagaaaacat ttaactttgg ccagagtgaa    1080
gcagttcatt tatttcaaac aatgatggag tgtatgaaaa aaaaagagct tatcactgtt    1140
tttcacattg gatcagagga tcatcaagat atagatgtgg ccatactcac tgcactgctg    1200
aaaggtacta atgcatctgc atttgaccag cttatcctta cactggcatg ggacagagtt    1260
gatattgcca aaaatcatgt atttgtttat ggacaacagt ggctggttgg atccttggaa    1320
caggctatgc ttgatgctct tgtaatggac agagtttcat ttgtaaaact tcttattgaa    1380
aacggagtaa gcatgcataa attccttacc attcccagac tggaagaact ttataacact    1440
aaacaaggtc caaccaatcc aatgttgttc catctcattc gggatgtcaa gcagggtaat    1500
ctccccccgg ggtacaagat cactttaatt gatataggac ttgtgattga gtatctcatg    1560
ggaggaacct acagatgcac atacacacga aaacgttttc gattgatata taatagtctt    1620
ggtggaaata accggaggtc aggtcgaaat acctccagca gcacccctca gttgcgaaag    1680
agtcatgaaa cttttggcaa tagagctgat aaaaaggaaa aaatgagaca caatcatttc    1740
attaaaacag cccaacccta cagaccaaag atggatgcat ctatggaaga aggaaagaag    1800
aaaagaacca agatgaaat tgtagatata gatgatccag agaccaagcg ctttccttat    1860
cctcttaatg aattattaat ttgggcttgc cttatgaaga ggcaggtcat ggcccgcttt    1920
ttatggcagc atggtgaaga atcaatggct aaagcattag ttgcctgtaa aatctatcgt    1980
tcaatggctt atgaggcaaa gcagagtgac ctggtagatg atacttcaga ggaactgaag    2040
cagtattcca atgattttgg ccaactggca gttgaattac tggaacagtc cttcagacag    2100
gatgaaacga tggctatgaa attactcact tatgaactca aaaactggag taattcaacc    2160
tgcctcaagt tagcagtttc ttcaagactt agaccttttg tagctcacac ttgtacacag    2220
atgttgttat ctgatatgtg gatgggacgg ctgaatatga gaaaaaattc ctggtataag    2280
gtcatattaa gcattttagt tccacctgcc atattaatgc tagagtataa aaccaaggct    2340
gaaatgtccc atatcccaca atctcaagat gctcatcaaa tgacgatgga ggatagtgaa    2400
aacaattttc acaacataac agaagagata cccatggaag tatttaaaga agtaaagatt    2460
ttggacagca gtgatggaaa gaatgaaatg gagatacata ttaaatcaaa aaagcttcca    2520
atcacacgaa aattttatgc cttttatcat gcaccaattg taaagttctg gtttaacaca    2580
ttggcatatt taggatttct gatgctttat acatttgtag ttcttgtaaa aatggaacag    2640
ttaccttcag ttcaagaatg gattgttatc gcttatattt ttaccatgc tattgaaaaa    2700 gtccgtgagg tcttcatgtc tgaagctggg aaaatcagcc agaagattaa agtatggttt    2760
agtgactact tcaatgtcag tgacacaatt gccatcattt cttctttgt tggatttgga    2820 ctaagatttg gagcaaaatg gaactatatt aatgcatatg ataatcatgt ttttgtggct    2880
ggaagattaa tttactgtct taatataata ttttggtatg tgcgtttgct agactttcta    2940
gccgtaaatc aacaggcagg accttatgta atgatgattg gaaaaatggt ggccaatatg    3000
ttctacattg tagtgataat ggctcttgta ttgcttagtt ttggtgttcc cagaaaagca    3060
atactttatc cacatgaaga accatcttgg tctcttgcta agatatagt ttttcatcca    3120 tactggatga ttttggtga agtttatgca tatgaaattg atgtgtgtgc aaatgactcc    3180
actctcccga caatctgtgg tcctggaact tggttgactc catttcttca agcagtctac    3240
ctctttgtac agtatatcat tatggttaat ctccttatcg cattttttcaa taatgtatat    3300 ttacaagtga aggcaatttc caatattgta tggaagtatc agcggtatca ttttattatg    3360
```

```
gcttatcatg aaaaaccagt cctgcctcct cctcttatca tcctcagcca tatagtttca    3420
ctgttttgct gtgtatgcaa aagaagaaag aaagataaga cttccgatgg gccaaaactt    3480
ttcttaacag aagaagatca aagaaactc catgattttg aagagcagtg tgttgagatg     3540
tactttgatg agaaagatga caaattcaat tctgggagtg aagagagaat ccgggtcact    3600
tttgaaagag tggagcagat gagcattcag attaagaag ttggagatcg tgtcaactac     3660
ataaaaagat cattacagtc tttagattct caaattggtc atctgcaaga tctctcagcc    3720
ctaacagtag atacattgaa aacacttaca gcccagaaag cttcagaagc tagtaaagtg    3780
cacaatgaga tcacgcgaga attgagtatt tccaaacact tggctcagaa tcttattgat    3840
gatgttcctg taagaccttt gtggaagaaa cctagtgctg taaacacact gagttcctct    3900
cttcctcaag gtgatcggga agtaataat ccttttcttt gtaatatttt tatgaaagat      3960
gaaaaagacc cccaatataa tctgtttgga caagatttgc ccgtgatacc ccagagaaaa    4020
gaattcaaca ttccagaggc tggttcctcc tgtggtgcct tattcccaag tgctgtttct    4080
cccccagaat tacgacagag acgacatggg gtagaaatgt taaaaatatt taataaaaat    4140
caaaaattag gcagttcacc taatagttca ccacatatgt cctcccccacc aaccaaattt    4200
tctgtgagta ccccatccca gccaagttgc aaaagtcact tggaatccac aaccaaagat    4260
caagaaccca ttttctataa agctgcagaa ggggataaca tagaatttgg agcatttgtg    4320
ggacacagag atagtatgga cttacagagg tttaagaaa catcaaacaa aataagagaa     4380
ctgttatcta atgatactcc tgaaaacact ctgaaacatg tgggtgctgc tggatatagt    4440
gaatgttgta agacttctac ttctcttcac tcggtgcaag cagaaagctg tagtagaaga    4500
gcgtcgacgg aagactctcc agaagtcgat tctaaagcag cttttgttacc ggattggtta   4560
cgagatagac catcaaacag agaaatgcca tctgaaggag gaacattaaa tggtcttgct    4620
tctccattta gcccgttttt ggatacaaat tactattatt cagctgtgga agaaataac     4680
ctgatgaggt tgtcacagag tattcccttc gttcctgtac ctccacgagg cgagcctgtc    4740
acagtgtacc gtctggagga gagttctccc agtatactga ataacagcat gtcttcatgg    4800
tctcagctag gcctctgtgc caaaattgag ttttaagta aagaggaaat gggaggtggt     4860
ttacgaagag cagtcaaagt gctgtgtacc tggtcagagc acgatatcct gaagtcaggg    4920
catctctata tcattaagtc atttcttcct gaggtgataa acacatggtc aagcattat     4980
aaagaagata cggttctaca tctctgtctc agagaaatac aacaacagag agcagcacaa    5040
aagctcacat ttgcctttaa tcagatgaaa cccaaatcca taccatattc tccaaggttc    5100
cttgaagttt tcctgttgta ctgccattca gcagggcagt ggtttgctgt agaagagtgc    5160
atgactggtg aatttagaaa atacaacaac aataatggtg atgaaatcat tcctacaaat    5220
actctagaag agatcatgct agcctttagc cactggacct atgaatatac cagaggggag    5280
ttactggtac ttgacttaca aggagtggga gaaaacttga ctgacccatc tgtaataaaa    5340
gctgaagaaa aaagatcctg tgacatggtt tttggccctg ccaatctagg agaagatgca    5400
ataaaaact tcagagccaa acatcactgt aattcttgct gtcgaaagct taaacttcca    5460
gatttgaaga ggaatgacta cacgcctgat aaaattatat ttcctcagga tgagtcatca    5520
gatttgaatc ttcaatctgg aaattccacc aaagaatcag aagcaacaaa ttctgttcgt    5580
ctgatgttat ag                                                        5592

<210> SEQ ID NO 6
<211> LENGTH: 7123
<212> TYPE: DNA
```

<213> ORGANISM: Mus musculus

<400> SEQUENCE: 6

```
gccccgtctc cggcggaggc gggcgcgggc gcgtccctgt ggccagtcac ccggcggagc      60
tggtcgcaca attatgaaag actcgacttc tgctgctagc gctggagctg agttagttct     120
gagaaggttt cccggggctg tccttgttcg gtggcccgtg ccaccgcctc cggagacgct     180
ttccgataga tggctgcagg ccgcggaggt ggaggaggag ccgctgccct tccggagtcc     240
gccccgtgag gagaatgtcc cagaaatcct ggatagagag cactttgacc aagagggagt     300
gtgtatatat tataccaagc tccaaagacc ctcacagatg tcttccagga tgtcagattt     360
gtcagcaact tgtcagatgt ttctgtggtc gtttggtcaa gcaacatgca tgctttactg     420
caagtcttgc catgaaatac tcagatgtga aattgggtga acactttaac caggcaatag     480
aagaatggtc tgtggaaaag cacacggagc agagcccaac agatgcttat ggagtcatca     540
attttcaagg gggttctcat tcctacagag ctaagtatgt gagactatca tatgatacca     600
aacctgaaat cattctgcaa cttctgctta agaatggca aatggagtta cccaaacttg      660
ttatttctgt acatggaggc atgcagaagt ttgaacttca tccaagaatc aagcagttgc     720
ttggaaaggg tcttattaaa gctgcagtta caaccggagc ttggatttta actggaggag     780
tcaatacagg tgtggcaaaa catgttggtg atgccctcaa agaacatgct tccagatcat     840
ctcgaaaaat ttgcactatt ggaatagctc catgggagt gatagaaaac agaaatgatc      900
ttgttgggag agatgtggtt gctccttatc aaacccatt gaatcccttg agcaaattga      960
atgttctgaa taatctacac tcccatttca tcttggtgga tgatggcact gttggaaagt    1020
atggggcaga agtcagactg agaagagaac ttgaaaaaac cattaatcag caaagaattc    1080
atgctagaat tgggcaagga gttcctgtgg tggctttgat atttgaaggc gggccaaatg    1140
tcatccttac agtactggag taccttcagg aaagcccccc agttccagtt gttgtgtgtg    1200
aagggacagg cagagctgca gatttactag cctatatcca caaacagaca gaggaaggag    1260
gaaatcttcc tgatgcagca gagcctgata ttatatcaac tatcaagaaa catttaact    1320
ttggccagag tgaagcagtt catttatttc aaacaatgat ggagtgtatg aaaaaaaaag    1380
agcttatcac tgttttcac attggatcag aggatcatca agatatagat gtggccatac    1440
tcactgcact gctgaaaggt actaatgcat ctgcatttga ccagcttatc cttacactgg    1500
catgggacag agttgatatt gccaaaaatc atgtatttgt ttatggacaa cagtggctgg    1560
ttggatcctt ggaacaggct atgcttgatg ctcttgtaat ggacagagtt tcatttgtaa    1620
aacttcttat tgaaaacgga gtaagcatgc ataaattcct taccattccc agactggaag    1680
aactttataa cactaaacaa ggtccaacca atccaatgtt gttccatctc attcgggatg    1740
tcaagcaggg taatctcccc ccggggtaca agatcacttt aattgatata ggacttgtga    1800
ttgagtatct catgggagga acctacagat gcacatacac acgaaaacgt ttcgattga     1860
tatataatag tcttggtgga aataaccgga ggtcaggtcg aaatacctcc agcagcaccc    1920
ctcagttgcg aaaagagtcat gaaacttttg gcaatagagc tgataaaaag gaaaaaatga    1980
gacacaatca tttcattaaa acagcccaac cctacagacc aaagatggat gcatctatgg    2040
aagaaggaaa gaagaaaaga accaaagatg aaattgtaga tatagatgat ccagagacca    2100
agcgcttttcc ttatcctctt aatgaattat taatttgggc ttgccttatg aagaggcagg    2160
tcatggcccg cttttatgg cagcatggtg aagaatcaat ggctaaagca ttagttgcct     2220
gtaaaatcta tcgttcaatg gcttatgagg caaagcagag tgacctggta gatgatactt    2280
```

```
cagaggaact gaagcagtat tccaatgatt ttggccaact ggcagttgaa ttactggaac    2340
agtccttcag acaggatgaa acgatggcta tgaaattact cacttatgaa ctcaaaaact    2400
ggagtaattc aacctgcctc aagttagcag tttcttcaag acttagacct tttgtagctc    2460
acacttgtac acagatgttg ttatctgata tgtggatggg acggctgaat atgagaaaaa    2520
attcctggta taaggtcata ttaagcattt tagttccacc tgccatatta atgctagagt    2580
ataaaaccaa ggctgaaatg tcccatatcc cacaatctca agatgctcat caaatgacga    2640
tggaggatag tgaaaacaat tttcacaaca taacagaaga gatacccatg gaagtattta    2700
aagaagtaaa gattttggac agcagtgatg gaaagaatga aatggagata catattaaat    2760
caaaaaagct tccaatcaca cgaaaatttt atgcctttta tcatgcacca attgtaaagt    2820
tctggtttaa cacattggca tatttaggat ttctgatgct ttatacattt gtagttcttg    2880
taaaaatgga acagttacct tcagttcaag aatggattgt tatcgcttat attttaccct    2940
atgctattga aaaagtccgt gaggtcttca tgtctgaagc tgggaaaatc agccagaaga    3000
ttaaagtatg gtttagtgac tacttcaatg tcagtgacac aattgccatc atttctttct    3060
ttgttggatt tggactaaga tttgagcaa atggaacta tattaatgca tatgataatc    3120 atgttttgt ggctggaaga ttaatttact gtcttaatat aatattttgg tatgtgcgtt    3180
tgctagactt tctagccgta aatcaacagg caggacctta tgtaatgatg attggaaaaa    3240
tggtggccaa tatgttctac attgtagtga taatggctct tgtattgctt agttttggtg    3300
ttcccagaaa agcaatactt tatccacatg aagaaccatc ttggtctctt gctaaagata    3360 tagttttca tccatactgg atgattttg gtgaagttta tgcatatgaa attgatgtgt    3420
gtgcaaatga ctccactctc ccgacaatct gtggtcctgg aacttggttg actccatttc    3480
ttcaagcagt ctacctcttt gtacagtata tcattatggt taatctcctt atcgcatttt    3540
tcaataatgt atatttacaa gtgaaggcaa tttccaatat tgtatggaag tatcagcggt    3600
atcattttat tatggcttat catgaaaaac cagtcctgcc tcctcctctt atcatcctca    3660
gccatatagt ttcactgttt tgctgtgtat gcaaaagaag aaagaaagat aagacttccg    3720
atgggccaaa acttttctta acagaagaag atcaaaagaa actccatgat tttgaagagc    3780
agtgtgttga gatgtacttt gatgagaaag atgacaaatt caattctggg agtgaagaga    3840
gaatccgggt cactttgaa agagtggagc agatgagcat tcagattaaa gaagttggag    3900
atcgtgtcaa ctacataaaa agatcattac agtctttaga ttctcaaatt ggtcatctgc    3960
aagatctctc agccctaaca gtagatacat tgaaaacact tacagcccag aaagcttcag    4020
aagctagtaa agtgcacaat gagatcacac gagaattgag tatttccaaa cacttggctc    4080
agaatcttat tgatgatgtt cctgtaagac ctttgtggaa gaaacctagt gctgtaaaca    4140
cactgagttc ctctcttcct caaggtgatc gggaaagtaa taatccttttt ctttgtaata    4200 tttttatgaa agatgaaaaa gacccccaat ataatctgtt tggacaagat ttgcccgtga    4260
taccccagag aaaagaattc aacattccag aggctggttc ctcctgtggt gccttattcc    4320
caagtgctgt ttctccccca gaattacgac agagacgaca tggggtagaa atgttaaaaa    4380
tatttaataa aaatcaaaaa ttaggcagtt cacctaatag ttcaccacat atgtcctccc    4440
caccaaccaa atttctgtg agtacccccat cccagccaag ttgcaaaagt cacttggaat    4500
ccacaaccaa agatcaagaa cccatttttct ataaagctgc agaaggggat aacatagaat    4560
ttggagcatt tgtgggacac agagatagta tggacttaca gaggtttaaa gaaacatcaa    4620
acaaaataag agaactgtta tctaatgata ctcctgaaaa cactctgaaa catgtgggtg    4680
```

```
ctgctggata tagtgaatgt tgtaagactt ctacttctct tcactcggtg caagcagaaa    4740
gctgtagtag aagagcgtcg acggaagact ctccagaagt cgattctaaa gcagctttgt    4800
taccggattg gttacgagat agaccatcaa acagagaaat gccatctgaa ggaggaacat    4860
taaatggtct tgcttctcca tttaagcccg ttttggatac aaattactat tattcagctg    4920
tggaaagaaa taacctgatg aggttgtcac agagtattcc cttcgttcct gtacctccac    4980
gaggcgagcc tgtcacagtg taccgtctgg aggagagttc tcccagtata ctgaataaca    5040
gcatgtcttc atggtctcag ctaggcctct gtgccaaaat tgagttttta agtaaagagg    5100
aaatgggagg tggtttacga agagcagtca aagtgctgtg tacctggtca gagcacgata    5160
tcctgaagtc agggcatctc tatatcatta agtcatttct tcctgaggtg ataaacacat    5220
ggtcaagcat ttataaagaa gatacggttc tacatctctg tctcagagaa atacaacaac    5280
agagagcagc acaaaagctc acatttgcct ttaatcagat gaaacccaaa tccataccat    5340
attctccaag gttccttgaa gttttcctgt tgtactgcca ttcagcaggg cagtggtttg    5400
ctgtagaaga gtgcatgact ggtgaattta gaaaatacaa caacaataat ggtgatgaaa    5460
tcattcctac aaatactcta gaagagatca tgctagcctt tagccactgg acctatgaat    5520
ataccagagg ggagttactg gtacttgact tacaaggagt gggagaaaac ttgactgacc    5580
catctgtaat aaaagctgaa gaaaaaagat cctgtgacat ggttttggc cctgccaatc    5640 taggagaaga tgcaataaaa aacttcagag ccaaacatca ctgtaattct tgctgtcgaa    5700
agcttaaact tccagatttg aagaggaatg actacacgcc tgataaaatt atatttcctc    5760
aggatgagtc atcagatttg aatcttcaat ctggaaattc caccaaagaa tcagaagcaa    5820
caaattctgt tcgtctgatg ttatagtgct gagtcattgg ttttgccta cacttcacaa    5880 aagtgtaact gtcagttttc ctttcggggg aattgatgat ataggaagat gtgtgcaaaa    5940
tgagcttgct ggccccacac atagtctaga ggtaatgttc tcattgaaaa acgcctggag    6000
gctgcagatg acagctggaa agtgctagct ggcagagagt cagtgctctc ggctggtgaa    6060
gggcgggaac cttgctgctg agagtggtgg ttctctcacc tggtgcagga ccattaacca    6120
aagtcaagtc ttcagatttg attggctgct cagtcacagc cattcagcta aggaaactaa    6180
attgcgcagc tttttaaatg gctgaagtct tcctcagttt gtgctctatg ataatgatgt    6240
tagctctcaa ctaggtgttt gtggccacgg gagaactact ccttacaatt ttgcttcaca    6300
ggcatgttac aaagcctgca ctgaaaaccg tttgtcttcc ctctctccct ccctcttttc    6360
cctgtagtat tgaggatcaa acccagggcc tcatgaagac cattttctaa gagacatttt    6420
atttaagaat caactataga gtctatgttt atggatacag ccagtttttg ttaaacaaaa    6480
cctgaattgt gcaaaagggt ttttaacat ttatcaatgt taagtaaaag aaagccatga    6540
taaataagaa ttaactcact gttcaatggg tgtttcctgt gaggaaggtt acagttgtaa    6600
cagcctgcag ttgcatacat ctccaaagat ttacagactt agtgtatcaa atcagagtgt    6660
catgtgagct ctcacattga aaattctata ggaatgtgtc aatgtgaatt ctatttctgg    6720
tacttaagaa atcagttgtt ggattatcct tatacagtat agggagatca caatacaact    6780
ttatgccaat aaaatctaac ttaattgccc agatattttt gcatatttag caacaagaaa    6840
agcttatcat ttgactcaag ttttatgctt tctctttctt ttcatttcct aggtactaat    6900
tttaattttt atttggaagg agcagtgtaa agcttacttg tattcaatag tgtatctcat    6960
agatacagac aaggccgcag agataagctg taaatagtg tttaatgttg atgtggagag    7020
aaaggtgtat tacttaaaaa tactatacca tatacgtttt gtatatcatt aaatctttaa    7080
```

```
aagaaattaa atttattctt gtttamaraa aaaaaaaaaa aaa                    7123

<210> SEQ ID NO 7
<211> LENGTH: 20
<212> TYPE: DNA
<213> ORGANISM: Artificial sequence
<220> FEATURE:
<223> OTHER INFORMATION: PCR primer

<400> SEQUENCE: 7
gtcacttgga aactggaacc                                              20

<210> SEQ ID NO 8
<211> LENGTH: 20
<212> TYPE: DNA
<213> ORGANISM: Artificial sequence
<220> FEATURE:
<223> OTHER INFORMATION: PCR primer

<400> SEQUENCE: 8
cggtagatgg ccttctactg                                              20

<210> SEQ ID NO 9
<211> LENGTH: 10
<212> TYPE: DNA
<213> ORGANISM: Artificial sequence
<220> FEATURE:
<223> OTHER INFORMATION: PCR primer

<400> SEQUENCE: 9
gcggccgcat                                                         10

<210> SEQ ID NO 10
<211> LENGTH: 13
<212> TYPE: PRT
<213> ORGANISM: Artificial sequence
<220> FEATURE:
<223> OTHER INFORMATION: synthetic

<400> SEQUENCE: 10

Met Gly Asp Tyr Lys Asp Asp Asp Asp Lys Arg Pro His
1               5                   10
```